(12) United States Patent
Fiedler et al.

(10) Patent No.: US 10,173,015 B2
(45) Date of Patent: Jan. 8, 2019

(54) SYSTEMS, APPARATUSES AND METHODS TO ENCOURAGE INJECTION SITE ROTATION AND PREVENT LIPODYSTROPHY FROM REPEATED INJECTIONS TO A BODY AREA

(71) Applicant: Becton, Dickinson and Company, Franklin Lakes, NJ (US)

(72) Inventors: Alan W. Fiedler, Wayne, NJ (US); Robert E. West, Basking Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 16 days.

(21) Appl. No.: 15/100,032

(22) PCT Filed: Dec. 3, 2014

(86) PCT No.: PCT/US2014/068469
§ 371 (c)(1),
(2) Date: May 27, 2016

(87) PCT Pub. No.: WO2015/085019
PCT Pub. Date: Jun. 11, 2015

(65) Prior Publication Data
US 2017/0028141 A1    Feb. 2, 2017

Related U.S. Application Data

(60) Provisional application No. 61/911,850, filed on Dec. 4, 2013.

(51) Int. Cl.
*A61M 5/42* (2006.01)
*G06F 19/00* (2018.01)
(Continued)

(52) U.S. Cl.
CPC ............ *A61M 5/427* (2013.01); *A61M 5/003* (2013.01); *A61M 5/31* (2013.01); *G06F 19/00* (2013.01);
(Continued)

(58) Field of Classification Search
CPC ........ A61M 5/427; A61M 5/31; A61M 5/003; A61M 5/3204; A61M 2205/583;
(Continued)

(56) References Cited

U.S. PATENT DOCUMENTS 4,349,338 A * 9/1982 Heppler ................. A61G 12/00
                                                        206/364
4,951,596 A * 8/1990 Wallace, Jr. ............... G09F 3/16
                                                        116/308
(Continued)

FOREIGN PATENT DOCUMENTS

AU        2011100534 A4    6/2011
DE   10 2008 016 987 A1   10/2009
(Continued)

OTHER PUBLICATIONS

International Search Report dated Apr. 15, 2015, issued in PCT Application No. PCT/US2014/068469.
(Continued)

*Primary Examiner* — Lauren P Farrar
(74) *Attorney, Agent, or Firm* — Dickinson Wright PLLC

(57) ABSTRACT

Systems and methods encourage users to rotate injection sites and avoid lipodystrophy. Sleeves and/or lost-tooth gear dials and/or microswitches in or on injection pens or their caps, on vials, and on other portable devices manually adjust an indicator before or after an injection to show a current or next injection site in accordance with a site rotation plan. Injected medicine packaging and related printed indicia encourage site rotation. Optical devices employing optical (Continued)

mouse or projection technology help locate and/or distribute injection sites within a body area. A mobile phone app tracks injections and locations to select next injection site, and can use imaging to locate a target injection site and optionally diagnose lipodystrophic conditions and record them. Tactile and print media educational tools are presented to help users palpate and identify lipos in body areas having injection sites.

11 Claims, 44 Drawing Sheets

(51) Int. Cl.
    *A61M 5/00*     (2006.01)
    *A61M 5/31*     (2006.01)
    *G09B 19/00*     (2006.01)
    *G09B 23/28*     (2006.01)
    *A61M 5/32*     (2006.01)
    *A61M 5/50*     (2006.01)

(52) U.S. Cl.
    CPC ....... *G06F 19/3468* (2013.01); *G09B 19/003* (2013.01); *G09B 23/285* (2013.01); *A61M 5/002* (2013.01); *A61M 5/3204* (2013.01); *A61M 5/50* (2013.01); *A61M 2005/3125* (2013.01); *A61M 2005/3126* (2013.01); *A61M 2205/505* (2013.01); *A61M 2205/52* (2013.01); *A61M 2205/581* (2013.01); *A61M 2205/582* (2013.01); *A61M 2205/583* (2013.01)

(58) Field of Classification Search
    CPC .... A61M 2005/3126; A61M 2205/582; A61M 2005/3125; A61M 5/50; A61M 2205/505; A61M 5/002; A61M 2205/52; A61M 2205/581; G06F 19/3468; G09B 19/003; G09B 23/285
    See application file for complete search history.

(56) References Cited

U.S. PATENT DOCUMENTS

| | | |
|---|---|---|
| 6,319,467 B1 | 11/2001 | McLernon, III |
| 2001/0053894 A1 | 12/2001 | Steenfeldt-Jensen et al. |
| 2002/0129758 A1* | 9/2002 | Hanley ............... G09F 3/02 116/308 |
| 2005/0085776 A1 | 4/2005 | Hommann et al. |
| 2005/0090782 A1* | 4/2005 | Marshall .......... A61M 5/31525 604/211 |
| 2007/0012322 A1 | 1/2007 | Ragg |
| 2008/0139900 A1 | 6/2008 | Randlov et al. |
| 2009/0281493 A1 | 11/2009 | Karanzas |
| 2009/0311311 A1 | 12/2009 | Shantha et al. |
| 2010/0198153 A1 | 8/2010 | Yang |
| 2012/0037291 A1 | 2/2012 | Goolishian |

FOREIGN PATENT DOCUMENTS

| | | |
|---|---|---|
| EP | 0 688 572 A1 | 12/1995 |
| EP | 0 897 728 A1 | 2/1999 |
| FR | 2 980 977 | 4/2013 |
| JP | 2002-58739 | 2/2002 |
| JP | 2005-514120 | 5/2005 |
| JP | 2011-224182 A | 11/2011 |
| WO | WO 2003/057285 A2 | 7/2003 |

OTHER PUBLICATIONS

European Communication providing Extended European Search Report dated Jul. 14, 2017 which issued in corresponding Patent Application No. 14868110.9.

Japanese Office Action dated May 22, 2018, which issued in the corresponding Japanese Patent Application 2016-536618, including English translation.

\* cited by examiner

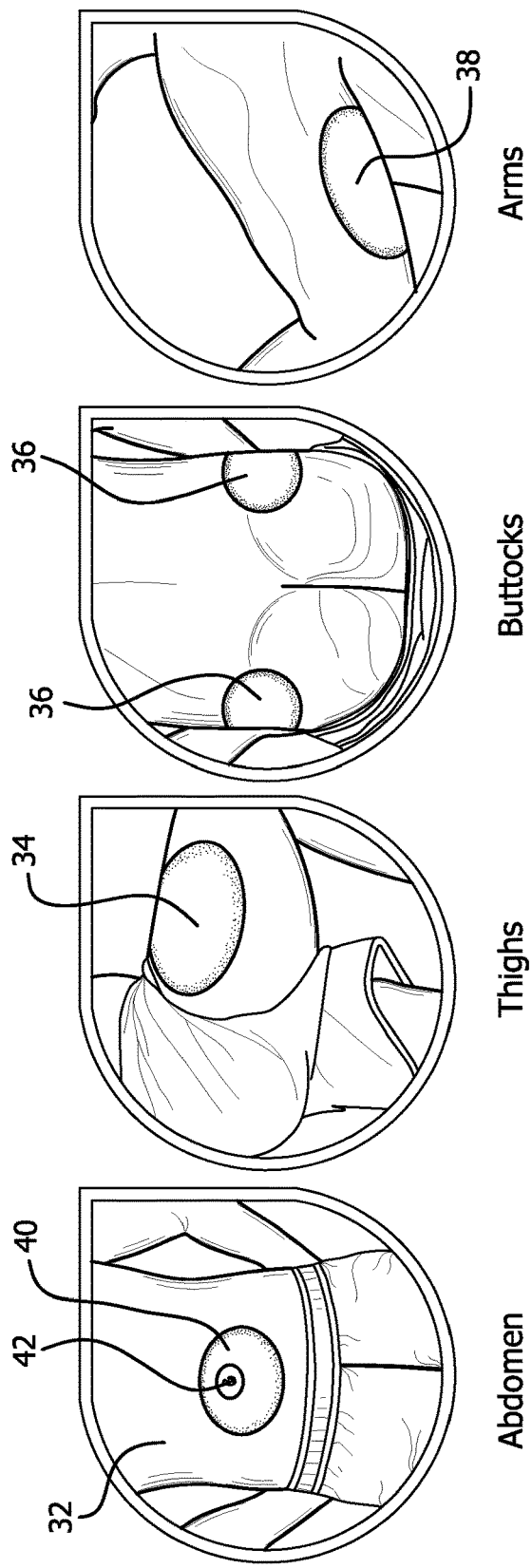

What is lipohypertrophy? (lipo-hy-per-tro-fi)

Lipohypertrophy, sometimes referred to as 'lipo', is a thickened area of tissue, or lump, that can develop under the skin where insulin injections are given over and over.

Why are lipos a problem?
The main concern is that if you inject into a lipo, insulin may not be absorbed the way it should.

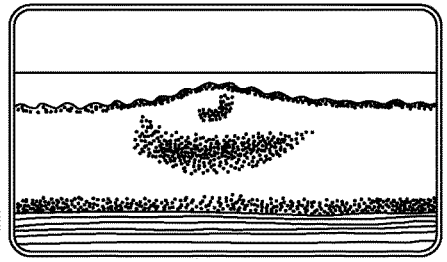

This may result in:
- ups and downs in blood sugar control
- the need for more insulin Simple changes to your injection technique will help.

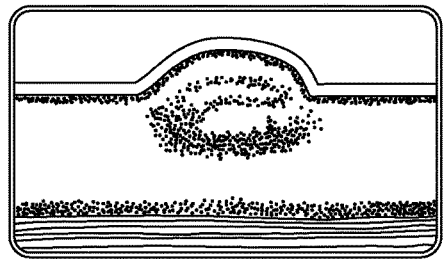

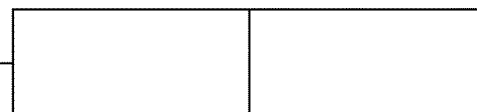

DETECT  ROTATE  CHANGE  CONTROL

THINK LIPOHYPERTROPHY

FIG. 40F

SYSTEMS, APPARATUSES AND METHODS TO ENCOURAGE INJECTION SITE ROTATION AND PREVENT LIPODYSTROPHY FROM REPEATED INJECTIONS TO A BODY AREA

CROSS-REFERENCE TO RELATED APPLICATIONS

Related subject matter is disclosed and claimed in commonly owned U.S. Pat. Nos. 7,597,853 and 7,645,264, the entire contents of which are incorporated herein by reference.

BACKGROUND OF THE INVENTION

Field of the Invention:

The present invention relates to methods and apparatuses that help patients adhere to an injection site rotation plan to minimize lipodystrophy and related adverse effects such as reduced or erratic medicament absorption and associated difficulties with managing a health condition employing the medicament as part of a care plan.

Description of Related Art:

Patients requiring frequent skin invasive actions such as injections or infusions of medicament into the skin can develop lipodystrophy at the injection sites. Lipodystrophy is a degenerative disorder of subcutaneous tissue. One type of lipodystrophy is lipohypertrophy, which can present in a patient as thickening of tissue such as lumps, or dents, or red and swollen tissue that is hard when palpated, in the affected area. The term "injection" as used herein can be, for example, injection by a needle (e.g., single dose syringe, or injection pen), or by infusion (e.g., a medicament pump with cannula for subcutaneous insertion such as an insulin pump), or any other action by which a patient's outer skin is pierced or crossed to deliver a medicament or to take a sample (e.g., a blood or tissue sample).

Lipodystrophy can be problematic for the patient because it can affect the rate of absorption of the medicament being administered by injection. For example, insulin therapy relies on reproducible absorption of insulin from a patient's subcutaneous (SC) tissue. Some patients with diabetes may require injections of a medicament (e.g., insulin) several times per day. Repeated application of insulin in a small skin area of a patient can induce lipodystrophic changes in the patient's skin structure (e.g., in the fatty tissue in the SC space). For example, a patient can suffer from lipodystrophy in an affected body area when he injects in that same body area and too close to adjacent injection sites in that area within a time period that is too short in duration to allow these injection site(s) to recover from the skin invasive action of the injection(s). Injection of insulin into a body area affected by lipodystrophic changes to the skin structure (e.g., SC tissue that may be fibrous and relatively avascular) can, in turn, induce erratic insulin absorption since a lack of blood vessels in the vicinity of the injection location (i.e., insulin depot) can reduce the rate of insulin absorption. For diabetic patients who administer insulin by injection or infusion techniques, less than optimal rate absorption can cause increased insulin requirements and/or poor metabolic control. Alternatively, a faster absorption rate may occur, which leads to poor glucose control.

Illustrative injection regimens will now be described with respect to insulin administration to diabetic patients. It is to be understood that the illustrative embodiments of the invention described below are applicable to other types of medical conditions requiring repetitive injections, and to other types of injection regimens using other types of medicament. Example injection regimens are:

Conventional therapy: use fast-acting and intermediate-acting types of insulin, typically requiring 2-3 injections per day;

Multiple daily injections (MDI): mealtime injections of fast-acting insulin to manage blood sugars during a meal and in the post-prandial period, and an injection of long-acting insulin manage blood glucose levels between meals, which can be at least 4 injections per day; and Continuous subcutaneous insulin infusion (CSII): administer insulin through a temporary flexible catheter inserted into subcutaneous tissue and worn in rotating sites for 2-3 days or 4-5 days. Lipohypertrophy can occur in body areas used for continuous insulin delivery systems (e.g., subcutaneous indwelling catheters and insulin pump), as well as injections using syringes or pen needles. Although patients may be instructed to avoid placing catheters in areas of lipohypertrophy, these areas are not necessarily recognized by patients or their caregivers and, as such, catheters are often placed where early lipohypertrophy is already present.

Evidence suggests a correlation between lipodystrophy, and failure to rotate injection sites or using small injection zones (e.g., body areas) repeatedly or injecting into the same location and/or re-using needles. Systematic site rotation can help to reduce the risk of developing lipohypertrophy. Thus, an easy-to-follow injection site rotation plan or scheme taught from the start of injection therapy is recommended.

With reference to FIG. 23A, eight body areas have been identified for insulin administration, that is, right and left sides of the patient's abdomen, arms, buttocks, and thighs. An important part of a care plan for a diabetic patient is education on and implementation of an injection site rotation plan. A site rotation plan can include injections or catheterization with an infusion device in a single body area (e.g., the abdomen) but using a pattern or grid to help distribute injections over this area. For example, one illustrative rotation scheme divides the area surrounding a patient's umbilicus (e.g., a target body area for injections), into sections (e.g., body area zones) such as the 12 hours of a clock face as shown in FIG. 24, or quadrants centered with respect to the umbilicus or halves of a body area such as the thigh as shown in FIG. 23B, to help a patient distribute injection sites within that body area.

The injection site rotation plan can also involve plural body areas. For example, other illustrative rotation schemes can include, but are not limited to, a patient rotating shots among plural body areas in a given day, or distributing shots within the same selected body area for a selected time period (e.g., a week) before rotating to another body area to distribute shots therein for the selected time period. One scheme with proven effectiveness involves dividing the target body area for injection sites into quadrants or halves, depending on the size of the area, using one quadrant or half per week, rotating within that area from day to day, and then moving clockwise each week to a new area[1].

[1] Pledger et al. "Importance of Injection Technique in diabetes" Journal of Diabetes Nursing 16 No 4 2012 pp 160-165.

Many patients, however, do not adhere to an adequate injection site rotation plan to avoid or minimize lipodystrophy and its related problems. For example, even when advised to rotate injection sites, patients continue with a less than optimal routine of using too few body areas and injection sites for different reasons. One reason is the Human Factor or ergonomic ease with which a patient can reach his or her different body areas to self-inject. For example, a patient's abdomen and thighs may be easier to reach with her hands to self-inject than her back or arms. As stated above, lipodystrophy can occur because a patient injects the same site day after day. It frequently occurs on both sides of the umbilicus or in the mid-thigh areas as these are convenient places to inject for diabetic patients. Another reason patients may purposefully or even unconsciously fail to practice an adequate injection site rotation plan is fear of pain in new sites. Further, some patients simply adhere to a less than optimal injection site rotation plan out of habit and for no particular reason other than not having adequate reminders or encouragement to rotate injection sites before lipodystrophy occurs. A need therefore exists for methods and/or apparatuses that encourage a patient to adhere to an injection site rotation plan such as, but not limited to, provide reminders, or help the patient keep record of past injection sites and select the next target body area and/or injection site.

In addition, rotation schemes may not sufficiently distribute injections over a target body area. For example, one rotation plan may provide 2 or 4 target areas (e.g., left, right thigh and/or left, right abdominal area), but leave where in that area to inject to the discretion of the patient, resulting in the patient most likely locating injections in only a few concentrated locations or injection sites within the target body area. A need therefore also exists for methods and/or apparatuses that help a patient distribute injection sites within a target body area.

Effective injection site rotation is therefore an important component to medicament administration. Early detection of a lipodystrophic site or site at imminent risk for developing lipodystrophic characteristics, and refraining from using such a site for a selected period of time, may preserve that site for future medicament delivery. Some sites need to be avoided for a period of time or avoided altogether, depending on the degree of damage done to the tissue. Further, injection sites need to be not only visually examined but also palpated since not all skin lesions are visible. A need therefore exists for methods and/or apparatuses that help a patient track lipodystrophic sites and avoid using them as target injection sites for at least a selected period of time, and optionally to help a patient discern whether a particular site on his or her body is developing lipodystrophic characteristics.

A variety of devices for administering insulin are available to diabetic patients, and range from unit dose disposable syringes, to reusable pen injectors, to infusion sets. A need therefore also exists for methods and/or apparatuses that encourage patients to adhere to an injection site rotation plan as well as accommodate their choice of insulin delivery mechanism.

SUMMARY OF THE INVENTION

The above and other problems are overcome, and additional advantages are realized, by illustrative embodiments of the present invention.

In accordance with illustrative embodiments of the present invention, methods and systems are provided to help a user adhere to an injection site rotation plan to minimize lipodystrophy. The methods and systems are implemented using a number of different form factors and devices such as improved injection pens, medicament containers such as vials, unit dose syringes and related packaging, infusion pump sets, various portable devices, and mobile apps.

In accordance with aspects of illustrative embodiments of the present invention, a device for encouraging injection site rotation can be implemented in a medication delivery device or be a separate device.

In accordance with aspects of illustrative embodiments of the present invention, a reminder system for varying the location of an injection site is provided that has a user-operable device including an indicator having indicia thereon related to a plurality of injection sites.

In addition, the reminder system can have any one or more of the following aspects:

the indicator comprises an indicator sleeve, which is rotatably secured to one of an injection pen body, an injection pen cap, and a medicament vial;

the indicator comprises an indicator sleeve, which is mounted to one of an injection pen body, an injection pen cap, and a medicament vial, and the system further comprises a window sleeve rotatably mounted to the one of the injection pen body, the injection pen cap, and the medicament vial to selectively permit viewing of a single one of the indicia at a time;

the reminder system comprises an additional indicator having indicia thereon related to days of the week, and a mechanism linking the indicator sleeve and the additional indicator so that advancing the additional indicator by seven indicia advances the indicator sleeve by a single indicia. For example, the additional indicator comprises a disc, or a sleeve. Further, a complete rotation of the additional indicator advances the indicator sleeve by a single indicia. The mechanism can comprises a lost-tooth gearing;

the reminder system comprises a rotating mechanism wherein the indicator comprises an indicator sleeve, which is movably disposed inside an injection pen having an injector button, the indicia being visible one at a time through a window disposed on the injection pen, and distal displacement of the injector button to complete the injection causes the rotating mechanism to advance the indicator sleeve by a single indicia;

the rotating mechanism can comprise a primary advancing protrusion disposed on the injection pen, and a plurality of radial protrusions disposed on the indicator sleeve, each of the plurality of radial protrusions corresponding to a single one of the indicia, wherein upon distal displacement of the injector button to complete an injection, the injector button displaces the indicator sleeve distally, and the interaction between the primary advancing protrusion and one of the radial protrusions during the distal displacement of the indicator sleeve causes rotation of the indicator sleeve;

the rotating mechanism can comprise a biasing member biasing the indicator sleeve proximally relative to the injection pen, and a secondary advancing protrusion disposed on the injection pen, the secondary advancing protrusion being circumferentially and axially offset from the primary advancing protrusion, wherein upon proximal displacement of the indicator sleeve due to the biasing member, the interaction between the secondary advancing protrusion and one of the radial protrusions during the proximal displacement of the indicator sleeve causes additional rotation of the indicator sleeve.

In accordance with aspects of illustrative embodiments of the present invention, a package is provided that comprises a carton, and a plurality of medical injection devices contained within said carton, said carton having printed indicia representing body areas on a patient, and printed indicia directing the injection by the medical injection devices to an injection site within respective body areas of the patient;

In addition, the package can have any one or more of the following aspects:

the carton has a plurality of compartments, and where each compartment contains a plurality of said medical injection devices;

the package includes printed indicia identifying each of said compartments as corresponding to respective body areas of the patient;

said indicia for each of said compartments has a different distinguishable color;

said indicia for each of said compartments has a different shape for identifying a body area of the patient;

each of said medical injection devices include printed indicia corresponding to the printed indicia for a respective compartment in which the medical injection device is arranged;

said indicia for each of said medical injection devices identifies an injection site within the body area of the patient;

the package can comprise a chart for recording the sequence of injection sites administered by the patient;

each of said medical injection devices include a label containing said indicia identifying an injection site, and where said labels are removable from the medical injection device and can be adhered to the chart to record the injection site;

the package can be used with a software application stored in non-transitory computer-readable memory that comprises instructions to control a programmable processing device to generate a display on a screen connected to the processing device, the display comprising the indicia representing the body areas, the processing device being controlled by the software application to receive a user input selecting one of the indicia on the display to correspond to an injection and its target location in the body area represented by the selected indicia, and to record in memory data relating to the injection comprising date and time of the injection and selected indicia;

the processing device is one of a mobile phone and a mobile computing device and the screen is a touchscreen, the user input comprising a touchscreen selection of one of the indicia on the display;

the processing device is controlled by the software application to generate a historical report of injections occurring over a selected period of time and their corresponding data comprising date and time and corresponding body area.

In accordance with aspects of illustrative embodiments of the present invention, an adhesive tape injection site indicator removably applied to a user's skin is provided that comprises at least one ply, said ply having a plurality of holes, said plurality of holes are arranged in said ply to correspond to a selected injection site distribution pattern, wherein the pattern is arranged such that, when an injection is made into respective ones of the plurality of holes, the pattern causes the respective injections to be spaced apart in the body area of the user that is covered by the indicator.

In addition, the adhesive tape injection site indicator can have any one or more of the following aspects:

the pattern arranges the holes to be spaced apart a selected distance to minimize lipohypertrophy in the body area when the respective injections are administered within a selected period of time;

the pattern arranges the holes to be at least the selected distance of 0.3-2.0 centimeters from adjacent ones of the holes;

the adhesive tape injection site indicator comprises a plurality of plies wherein corresponding holes in the plies are substantially aligned with respect to each other, and indicia are provided with respect to a different one of the holes on respective plies to represent a target injection site on that ply;

the adhesive tape injection site indicator comprises s plurality of plies, wherein the holes on each of the plies do not overlap.

In accordance with aspects of illustrative embodiments of the present invention, an adhesive tape injection site indicator kit is provided that comprises a plurality of indicators configured to be removably applied to a user's skin, and a template configured to indicate a distribution pattern for the indicators when they are affixed to a body area of a patient to mark respective target injection sites.

In addition, the adhesive tape injection site indicator kit can have any one or more of the following aspects:

the distribution pattern is configured to space the target injection sites a selected distance from each other to minimize lipohypertrophy in the body area when the respective injections are administered within a selected period of time;

the distribution pattern arranges the indicators to be at least the selected distance of 0.3-2.0 centimeters from adjacent ones of the indicators;

the indicators are stickers that each comprise adhesive to affix one side thereof to the patient;

the template is configured to have the indicators affixed to one side thereof in the distribution pattern, and the indicators are transferable onto a patient's skin when the one side of the template is placed against the patient;

the indicators are stickers that each comprise double-sided adhesive to affix one side thereof to the one side of the template and the other side thereof to the patient;

the indicators each comprise transferable ink on one side thereof and are configured to transfer a marking onto the patient from the template to represent a target injection site.

In accordance with aspects of illustrative embodiments of the present invention, an optical tool for tracking injection sites on a patient's body is provided that comprises an optical mouse, a memory device, a processing device connected to the memory device and the optical mouse, the processing device being configured to determine distances traveled by the mouse when moved over a patient's body and assigning position coordinates for target injection locations based on optical mouse outputs.

In addition, the optical tool can have any one or more of the following aspects:

the injections can be in designated body areas on the patient and each body area has a reference location, the processing device being configured to determine distances traveled by the optical mouse in a body area and assign position coordinates of the optical mouse relative to the reference location at selected points of the body area over which the optical mouse is being moved;

the memory stores injection data comprising an injection regimen indicating number of injections per day and recommended injection rotation plan, and position coordinates and dates and times of past injections, and the processing device is configured to select a target injection site using the current position coordinates of the optical mouse and the stored injection data;

the processing device is configured to space the position coordinates of the injection sites relative to adjacent sites by a selected amount to reduce lipohypertrophy;

the memory stores injection data comprising body area sites that are to be avoided as target injection sites, and the processing device is configured to not use these body area sites when selecting a target injection site;

the processing device is configured to generate an indication when the current position coordinates are determined to be proximal to a body area site that is to be avoided as a target injection site;

the processing device is configured to generate an indication when the current position coordinates are determined to be a target injection site.

In accordance with aspects of illustrative embodiments of the present invention, an image projection device is provided that is configured to be handheld and to project an injection site target image onto a body area of a patient.

In addition, the image projection device can have any one or more of the following aspects:

the image is a pattern representing a plurality of target injection sites spaced apart relative to each other to reduce lipohypertrophy;

the target injection sites in the pattern are spaced apart from each other by a selected distance of 0.3-2.0 centimeters;

the image projection device is deployed in a reusable part of an infusion pump set to facilitate selecting a location for deploying an injection assembly associated with the infusion pump;

the image projection device further comprises a memory device, a user interface, a processing device connected to the image projection device, the memory device and the user interface, the memory device storing a plurality of injection site target images, the user interface being configured to display a listing of the plurality of injection site target images from which a user can select a target image, and the processing device being operable to control the image projection device to display a selected target image;

the plurality of injection site target images comprises different target images for use on different body areas of the patient;

different target images are different sizes and/or shapes depending on their corresponding body areas;

the plurality of injection site target images comprises at least one target image that comprises different zones or sectors.

In accordance with aspects of illustrative embodiments of the present invention, a software application stored in non-transitory computer-readable memory is provided that comprises instructions to control a portable computing device having an image sensor, a screen display and a programmable processing device, the processing device being controlled by the software application to receive image data from the image sensor when pointed at a body area of a patient and display the image data on the screen display and an image of injection sites.

In addition, the software application can have any one or more of the following aspects:

the image sensor also captures an image of a user pointing to the body area with finger or other pointer, further comprising instructions to control the screen display to display the image of the pointer with the image data of the body area;

a target injection site in the body area is selected and the instructions control the processing device to generate feedback data when at least a selected portion of the pointer coincides with an orientation point corresponding to the target injection site;

the feedback data is at least one of audible indicator that the user has located the target injection site in the body area with the pointer, and a visual indicator on the target injection site on the screen display when the pointer reaches it in the body area, and a visual indicator of a direction and/or distance for moving the pointer to reach the target injection site;

the feedback data comprises an indicator of sites in the body area that should be avoided for injections;

the instructions control the processing device to automatically select the target injection site;

the processing device is controlled to analyze data comprising an injection regimen comprising number of injections per day, at least one target injection body area, a body area rotation plan if more than one body area is used, at least one injection pattern to distribute injections within a body area, and injection data comprising date and time and locations of past injections to automatically select the target injection site;

the portable computing device operates with another sensor that records image data related to a skin condition in the body area;

the image data comprises infrared wavelengths;

the skin condition comprises at least lipohypertrophy.

One embodiment is a software program that runs on a smart phone, computer, IPAD, PDA or other portable electronic device with a graphical display that guides the user as to where to inject to prevent lipodystrophic sites (e.g., hereinafter "lipos") from forming. An image of the body can be displayed showing the regions on the body to be used for injections and allow the user to zoom in on a region and site being suggested by the system for the next injection. The user can be provided with an option to accept the site or advance to a new site. All used sites are tracked and recorded so that the user can see which sites have been used the most when compared to other sites. The software program or application (hereinafter "app") can also provide the user with information for identifying lipos that may exist and record those possible sites in device memory with date and time, so that injections at those locations may be avoided (e.g., for a selected period of time) and the user's doctor can be consulted. The app can also provide incentive to the user to purchase a particular vendor's or manufacturer's needles in order to continue using the app by requiring the user to scan the product's bar code or enter a particular key. The app can also provide the user with coupons when used for an extended period of time. The app can be downloadable from the vendor's or manufacturer's website or any app store.

In accordance with aspects of illustrative embodiments of the present invention, a lipohypertrophy education tool is provided comprising a base, and a synthetic material provided on the base having a first texture selected to simulate subcutaneous fatty tissue when palpated, wherein the synthetic material comprises at least one area having a second texture selected to simulate a lipohypertrophy occurrence in the subcutaneous fatty tissue.

In addition, the lipohypertrophy education tool can have any one or more of the following aspects:

the base is dimensioned to be at least one of credit-card size, to be disposed in or on packaging containing injection supplies, to be disposed in a portable kit, and to be disposed on a wall or other surface on display to users.

Illustrative embodiments and respective aspects thereof can be used with other illustrative embodiments.

Additional and/or other aspects and advantages of the present invention will be set forth in the description that follows, or will be apparent from the description, or may be learned by practice of the invention.

BRIEF DESCRIPTION OF THE DRAWINGS

The present invention will be more readily understood with reference to the illustrative embodiments thereof as shown in the attached drawing figures, in which:

FIG. 23A depicts illustrative target body areas for administering injections and FIG. 23B depicts illustrative zones in a target body area;

FIGS. 39A, 39B, 40A, 40B, 40C, 40D, 40E, 40F, 41 and 42 are lipohypertrophy education devices constructed in accordance with illustrative embodiments of the present invention.

Throughout the drawing figures, like reference numbers will be understood to refer to like elements, features and structures.

DETAILED DESCRIPTION OF ILLUSTRATIVE EMBODIMENTS

Figure 1:
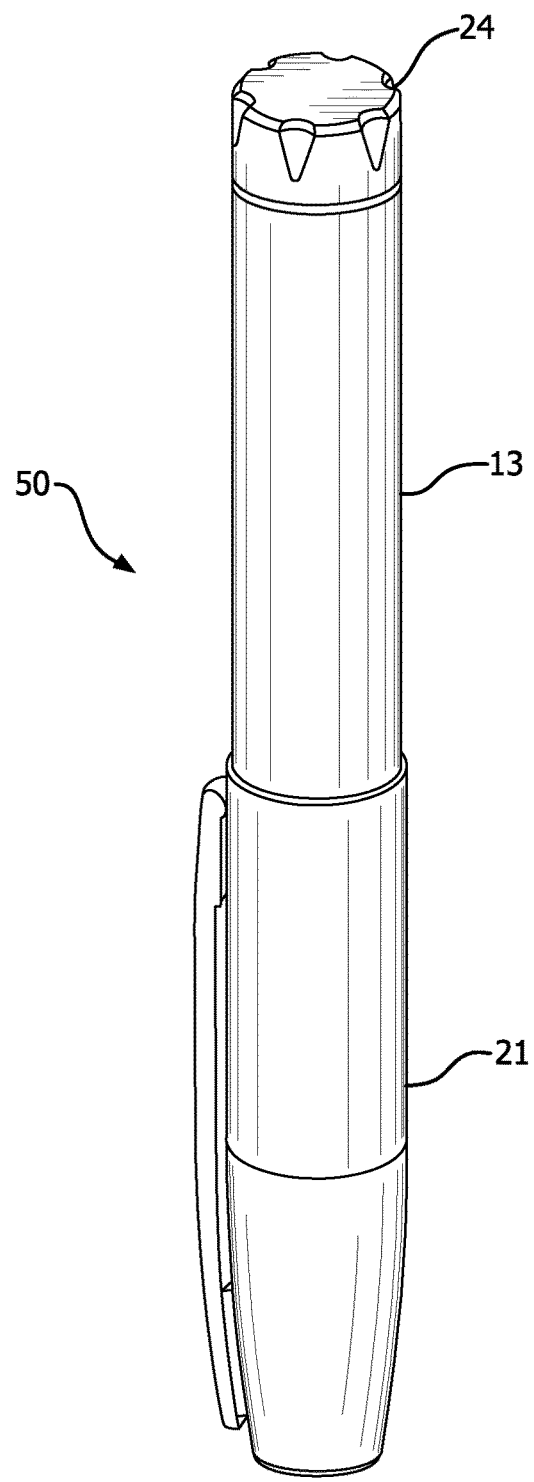
FIG. 1 is a perspective view of an illustrative drug delivery pen.

Reference will now be made in detail to embodiments of the present invention, which are illustrated in the accompanying drawings. The embodiments described herein exemplify, but do not limit, the present invention by referring to the drawings. As will be understood by one skilled in the art, terms such as up, down, bottom, and top are relative, and are employed to aid illustration, but are not limiting.

Illustrative embodiments of the present invention will now be described that encourage users (e.g., patients and/or their caregivers) to practice injection site rotation and therefore avoid or minimize the occurrence of lipodystrophy in patients and the above-mentioned potentially adverse effects of administering medicaments into lipodystrophic body areas of patients.

The illustrative embodiments of the present invention provide users with choices of different tools (e.g., different media and/or devices and formats) for tracking locations of injection sites, as well as rotation of target injection sites among different body areas or at least within a zone or section of a target body area for medicament administration by injection or infusion. The illustrative embodiments are with reference to diabetes management using insulin therapy. It is to be understood that these illustrative embodiments can be used with different injection and infusion devices and related products, as well as for different drug therapies and regimens for other medical conditions besides diabetes.

Drug Delivery Pens and Vials

Medication delivery pens are used for self-injection of precisely measured doses of medication. Pens are widely used, for example, by diabetics to self-inject insulin. A typical medication delivery pen includes a cartridge which contains a volume of liquid medication sufficient for several doses. Using a disposable pen needle attached to the pen device, the dose is injected into a tissue area, such as the intramuscular tissue layer, the subcutaneous tissue layer, or the intradermal tissue layer.

The assembly and operation of a typical pen injection device is described in commonly-assigned U.S. Pat. No. 7,645,264, which is hereby incorporated by reference in its entirety.

Figure 2:
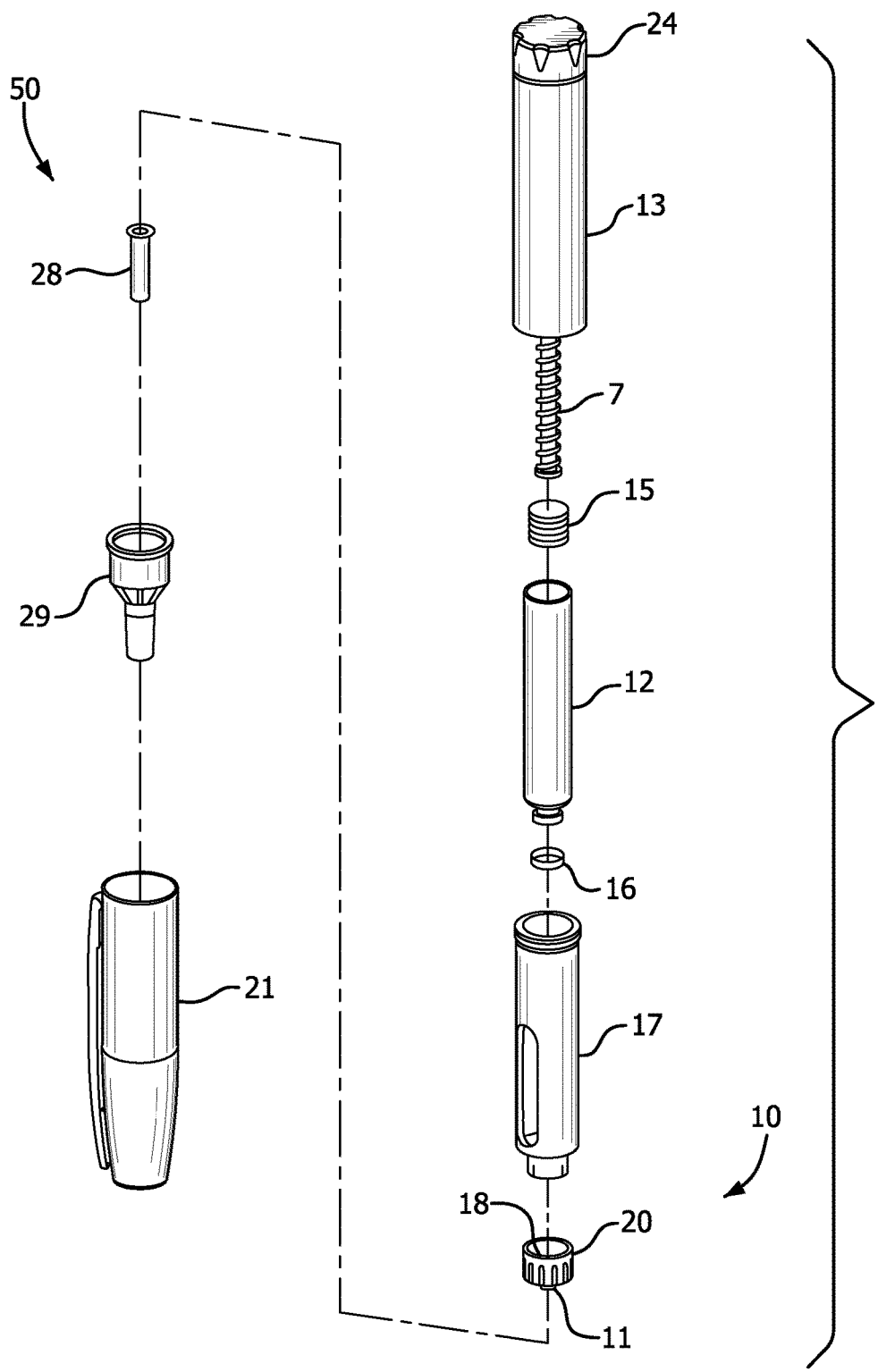
FIG. 2 is an exploded view of the illustrative drug delivery pen of FIG. 1.

Pen injection devices, such as an illustrative drug delivery pen or pen injector or injection pen 50, as shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is employed by the user to securely hold the pen injector 50 in a shirt pocket, purse, or other suitable location.

FIG. 2 is an exploded view of the illustrative drug delivery pen 50 shown in FIG. 1. The dose knob/button 24 has a dual purpose and is used to both set the dosage of the medication to be injected and to inject the dosed medicament via a lead screw 7 and stopper 15 from a medicament cartridge 12, which is attached to the drug delivery pen through a lower housing 17. The medicament cartridge 12 is typically a glass tube sealed at one end with a septum 16 and at the other end with the stopper 15. In standard drug delivery pens, the dosing and delivery mechanisms are all found within the outer sleeve 13. Those mechanisms are not described in greater detail herein as they are understood by those knowledgeable of the art. A pen needle assembly 10 includes a hub 20, a patient needle 11 extending from a patient end of the pen needle assembly, and a septum-penetrating needle cannula 18 disposed within the hub 20 on a non-patient side thereof. The septum-penetrating needle cannula 18 is in fluid communication with the patient needle 11. The hub 20 is typically screwed onto the lower housing 17. In attaching the hub 20 to the lower housing 17 or directly to the medicament cartridge 12, the septum-penetrating cannula 18 pierces the septum 16. The distal movement of the plunger or stopper 15 within the medicament cartridge 12 (due to advancement of the lead screw 7) causes medication to be forced into the patient needle 11 of the hub 20. To protect a user, a rigid outer shield 29 attaches to and covers the hub 20. The outer shield 29 can also be used as a handle or grip to screw hub 20 onto or off of pen injector 50. An inner shield or needle cover 28 covers the patient needle 11 within the outer shield 29.

Figure 3:
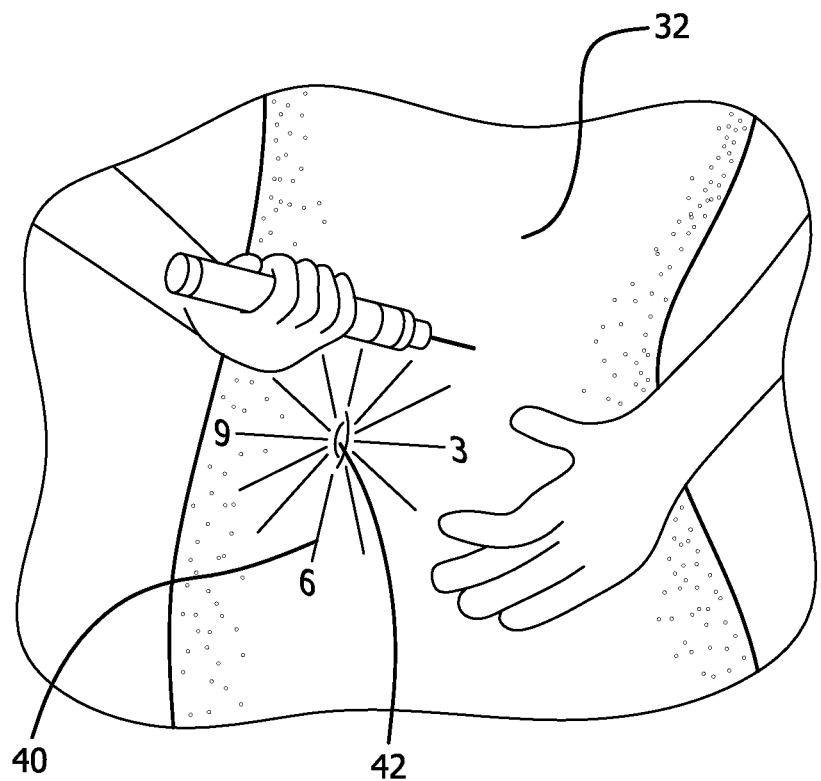
FIG. 3 is a perspective view of an injection site rotation scheme.
Figure 23B:
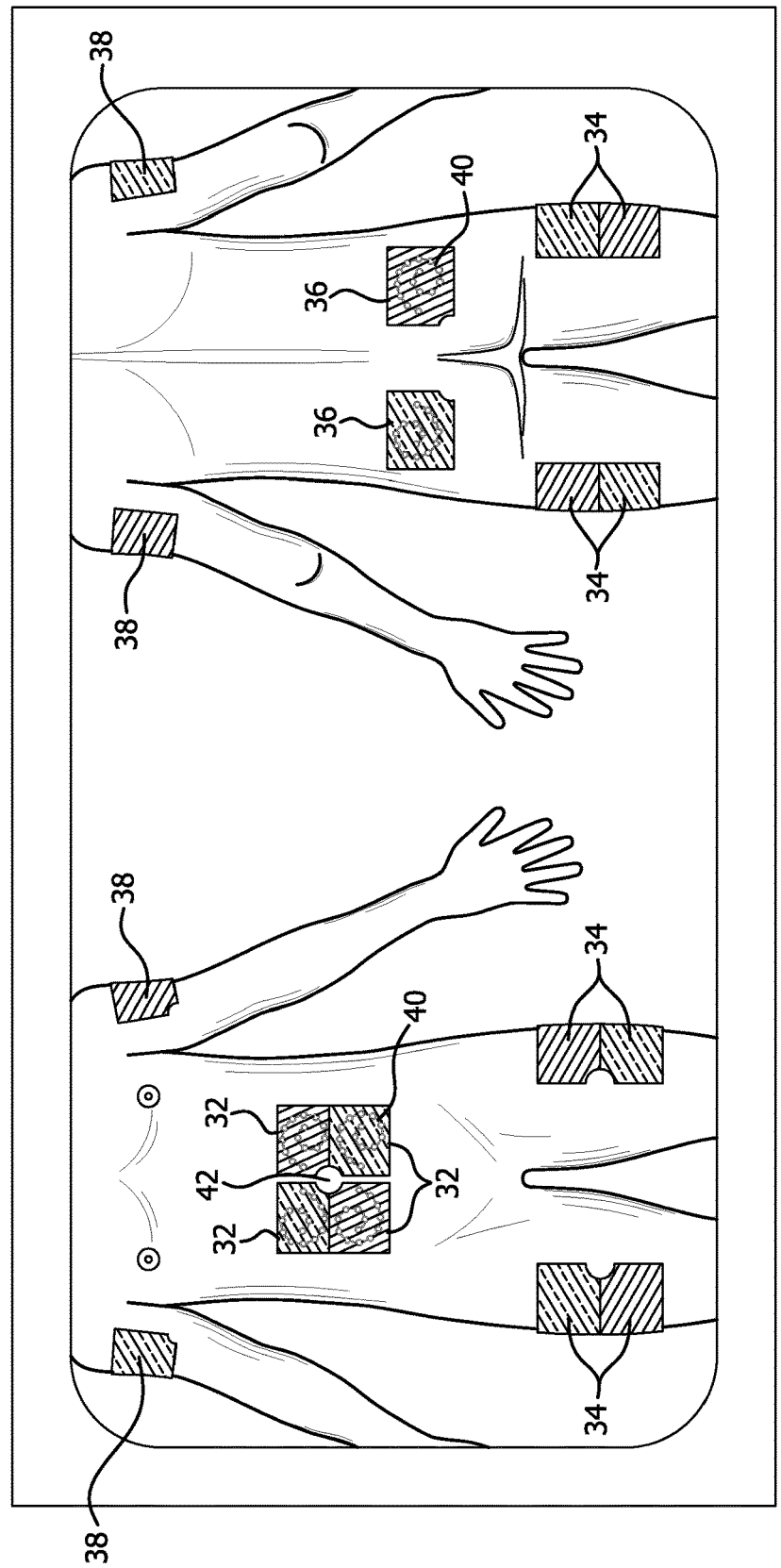
Figure 24:
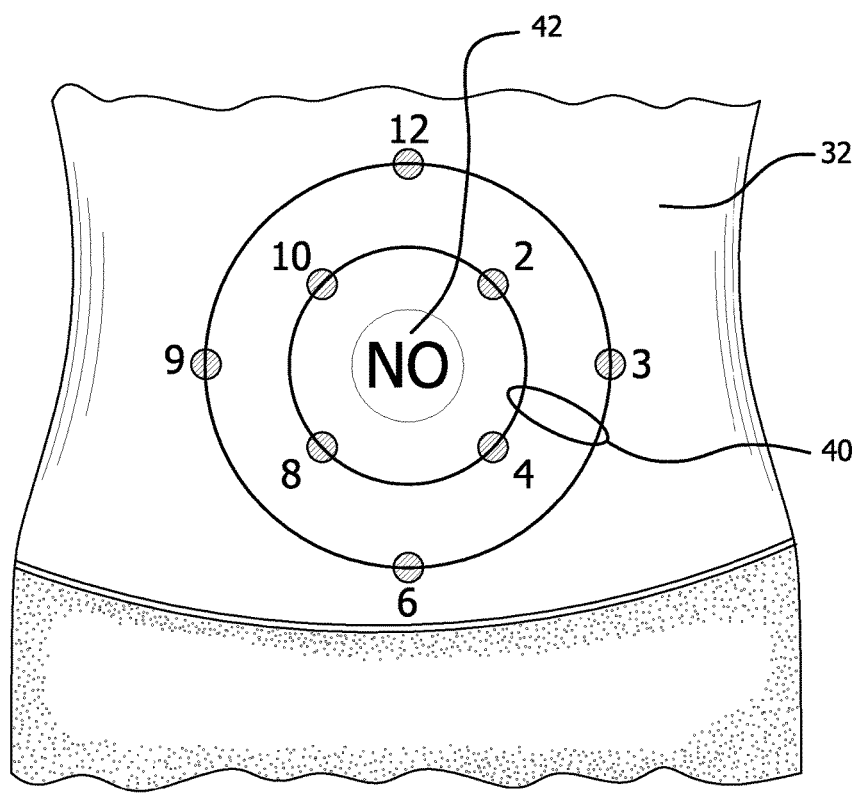
FIG. 24 depicts illustrative sections or zones of a target body area for administering injections.

FIG. 3 illustrates a schema for varying the location of an injection site. More specifically, a pattern 40 for injections within a body area can be, for example, an imaginary clock face 40 on the user's abdomen 32, and the user varies the injection site like the hour hand of the clock, for example, moving from 12 o'clock for one injection to one o'clock for the next injection and so on. The clock face can be centered on the user's umbilicus (i.e., belly button). Alternatively, the abdominal area of the body can be divided into different types of zones such as using compass zones (e.g., N, NE, E, SE, S, SW, W, and NW). Patterns 40 for dispersing injection sites on the abdomen can also be accomplished using concentric circles, as shown in FIG. 24, or dividing the abdominal area into designated areas such as quadrants as shown in FIG. 23B and then employing a pattern 40 within each designated area (e.g., quadrant) such as a matrix or grid pattern or a spiral pattern as depicted in FIG. 23B.

Figure 4:
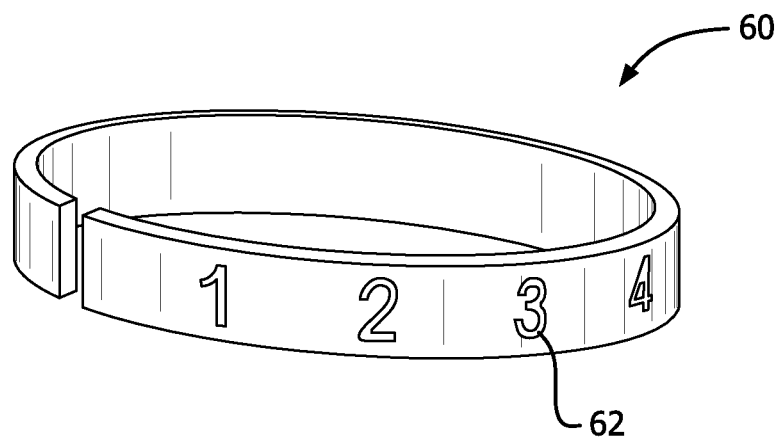
FIG. 4 is a perspective view of an indicator sleeve in accordance with an illustrative embodiment of the present invention.

According to one embodiment, a reminder system to aid a user in varying the location of an injection site includes an indicator, such as a hollow indicator sleeve 60, as shown in FIG. 4. The indicator sleeve 60 has indicia 62 thereon related to a plurality of injection sites. More specifically, the indicator sleeve 60 has numbers 1-12 corresponding to hours on a clock face, such as the imaginary clock face in FIG. 3. According to one embodiment, the indicator sleeve 60 is a flexible ring that can fit around another object, such as an injection pen, an injection pen cap, or a medicament vial. It is to be understood that the ring can be provided with different indicia to accommodate different injection regimens such as the afore-mentioned compass zones, or indicia representing different quadrants or sites on two or more concentric circles imagined or placed around the umbilicus, or number of days (e.g., 1-7, or abbreviations for the days of the week), or coordinates for a grid, or other indicia that represent a pattern of injections and that may vary depending on which body area(s) is used.

Figure 5:
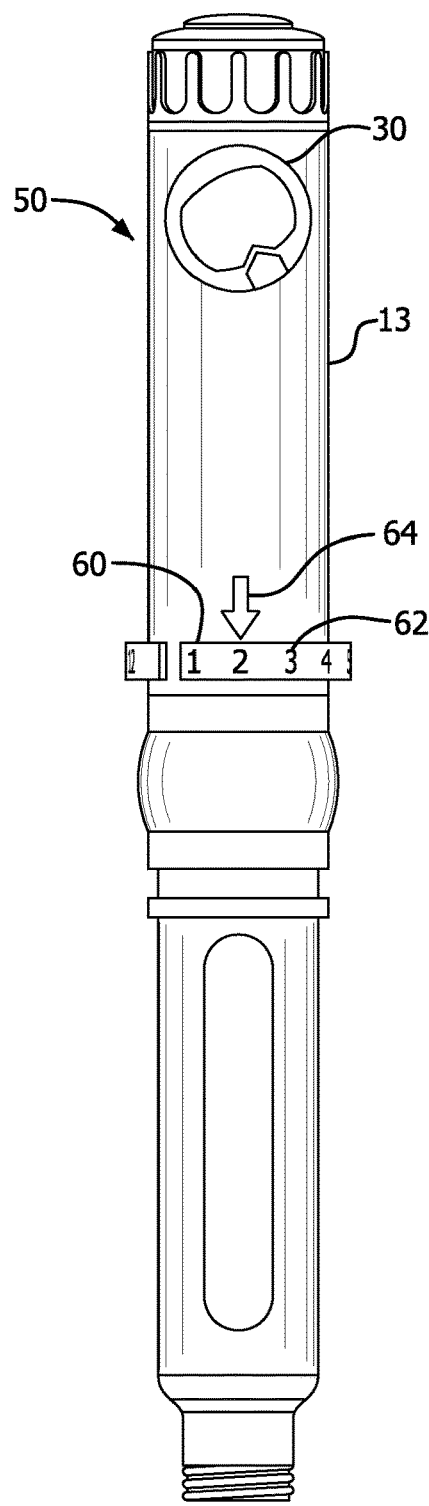
FIG. 5 is a perspective view of an injection pen in accordance with an illustrative embodiment of the present invention.

As shown in FIG. 5, the indicator sleeve 60 is rotatably disposed about the injection pen 50. For example, the sleeve 60 can be a flexible ring (e.g., made of rubber or other flexible material) that can be continuous or have a space along its circumference and can accommodate different sizes of pen housings. The sleeve 60 is provided with indicia 62 corresponding to a target injection site pattern or grid (e.g., numerals 1 through 12 representing a site rotation plan that employs a clock pattern or compass coordinates such as N, NE, E, SE, S, SW, W, and NW) to be employed in a selected body area. The indicia 62 can be aligned with the dose window. Alternatively, in addition to a dose window 30 used for setting a dose, the injection pen 50 can also include a site indicator 64, such as an arrow fixedly disposed on the injection pen body. According to one embodiment, the site indicator 64 is a separate piece adhered to the outer sleeve 13. One skilled in the art, however, will appreciate that the site indicator 64 can be, a raised or recessed feature molded into the outer sleeve 13, a marking, or other indicia without departing form the scope of the present invention. According to one embodiment, the outer sleeve 13 and the indicator sleeve 60 include detents to provide the user with tactile feedback to indicate revolution of the indicator sleeve 60 corresponding to the advancement of a single indicium. The detents can also provide audible feedback, such as a click.

Figure 22A:
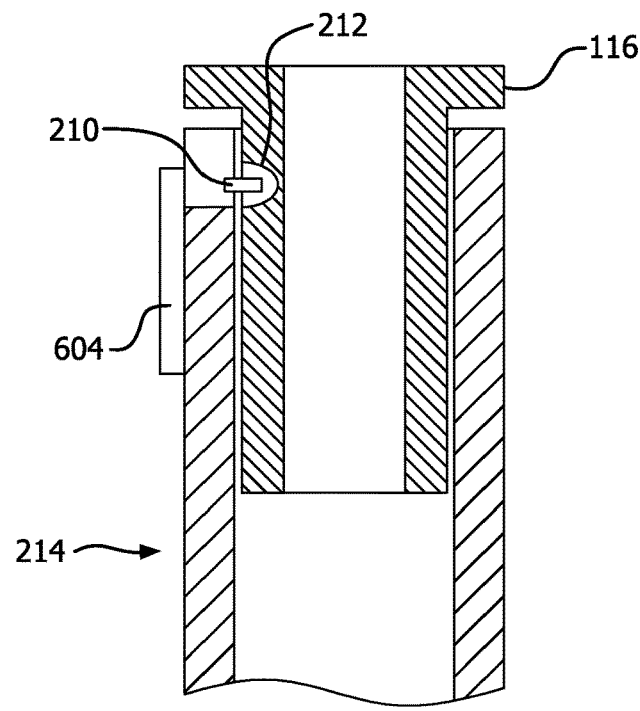
FIGS. 22A and 22B are, respectively, a partial cross-sectional view and a partial front view of a pen in accordance with an embodiment of the present invention.
Figure 22B:
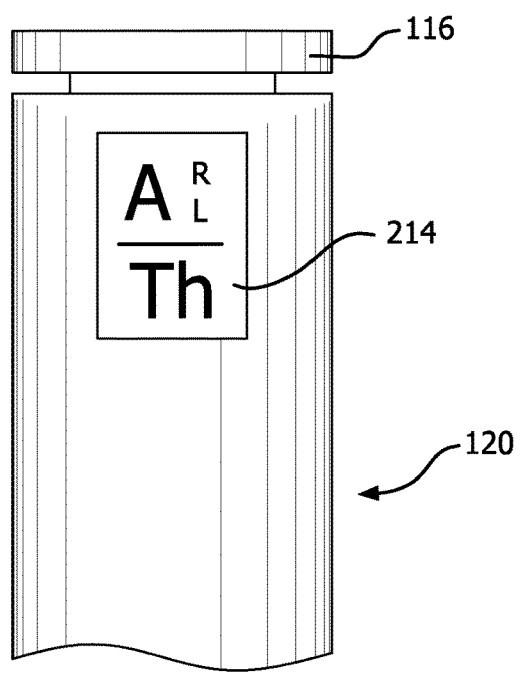
Figure 22C:
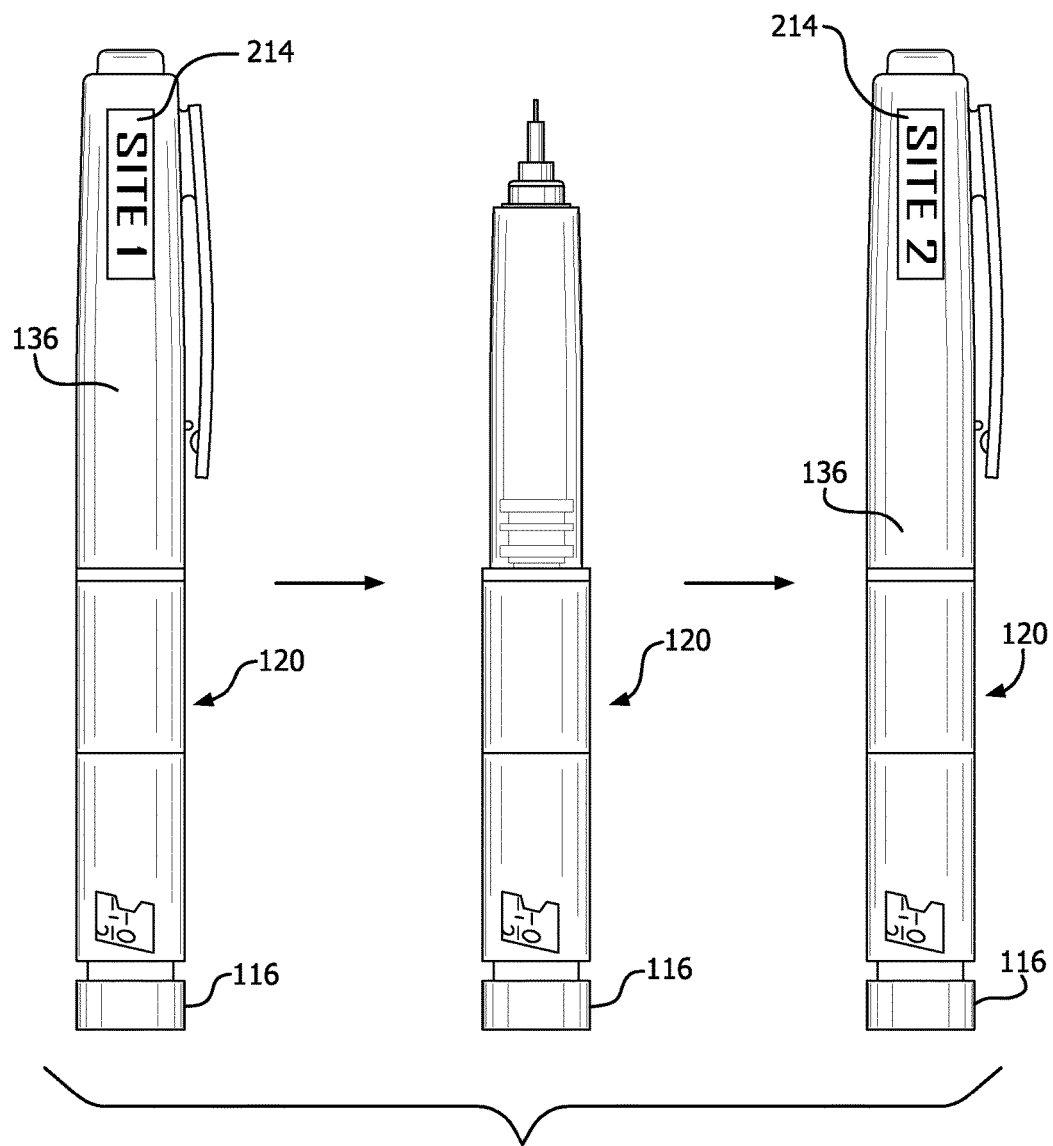
FIG. 22C depicts a pen having display on its pen cap for automatically indicating the next target injection site after pen is recapped in accordance with an illustrative embodiment of the present invention.

To use the reminder system illustrated in FIG. 5, before or after giving the injection at the site on the abdomen or other body area that corresponds to the indicium 62 aligned with the site indicator 64, the user manually rotates the indicator sleeve 60 so that the next consecutive indicium is aligned with the site indicator 64. Thus, prior to the next injection, the user can be reminded of the site for the next injection, and by varying the site, can reduce the likelihood of developing lipodystrophy. Use of this embodiment is simple, easy to remember, and can work on any injection pen, such as an insulin pen. Alternatively, the indicium can be advanced automatically, for example, as shown in FIGS. 22A through 22C and described below.

Figure 6:
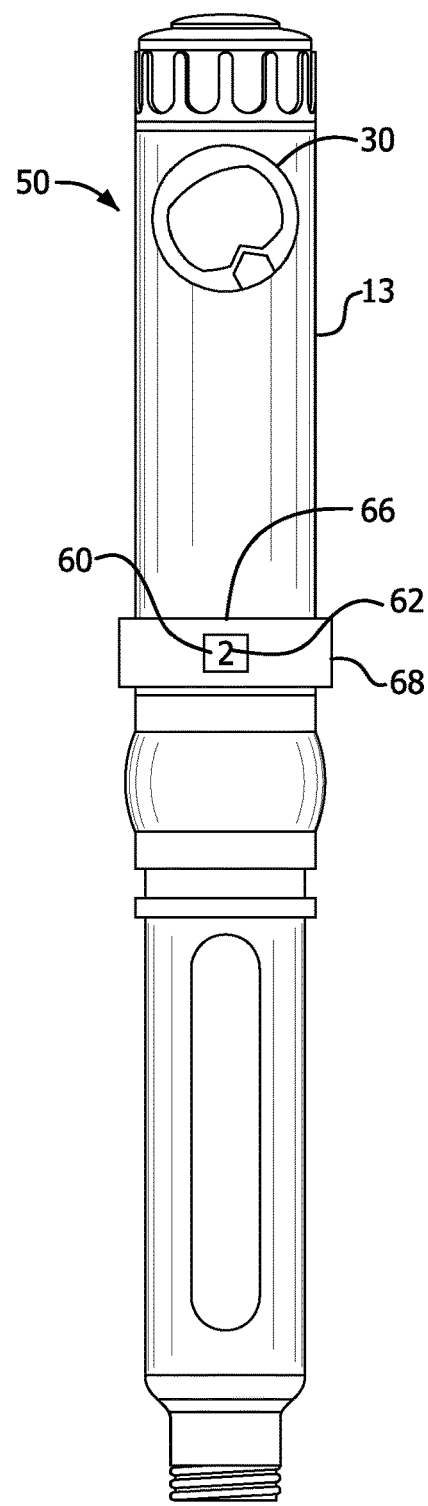
FIG. 6 is a perspective view of another injection pen in accordance with an illustrative embodiment of the present invention.

FIG. 6 illustrates another embodiment in which the indicator sleeve 60 is secured to the outer sleeve 13, and a window sleeve 66 having a window 68 is rotatably disposed about the outer sleeve 13. According to one embodiment, the indicia 62 are spaced and the window 68 is sized so that only one indicium is visible through the window at a given time. Use of this embodiment is similar to that of the FIG. 5 embodiment, except that instead of rotating the indicator sleeve 60, the user rotates the window sleeve 66. According to one embodiment, the window sleeve 66 and at least one of the outer sleeve 13 and the indicator sleeve 60 include detents to provide the user with tactile feedback to indicate revolution of the window sleeve 66 corresponding to the advancement of a single indicium. The detents can also provide audible feedback, such as a click.

In addition to a sleeve, an indicator in accordance with another illustrative embodiment of the present invention can be a wheel or disc with indicia on a face of the disc. In one embodiment, the disc is rotatably mounted in conjunction with a fixed site indicator. In use, the disc is rotated to align the next indicium with the site indicator subsequent to injection. According to one embodiment, the site indicator is an arrow. According to another embodiment, the fixed site indicator is a window, through which a single indicium is visible at a given time.

Figure 7:
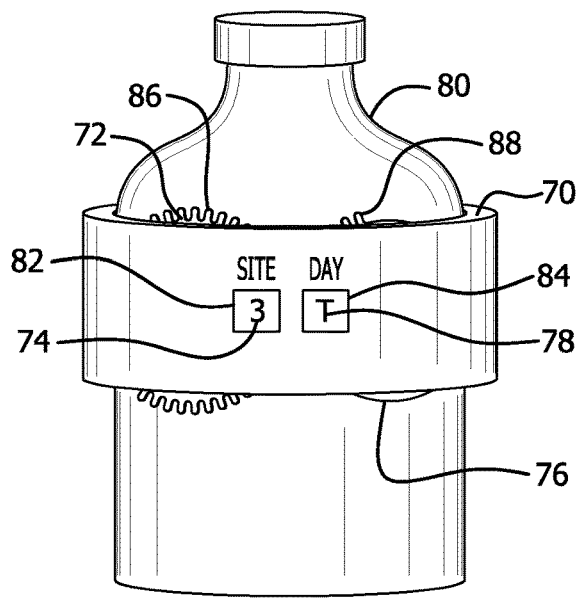
FIG. 7 is a perspective view of medicament vial in accordance with an illustrative embodiment of the present invention.
Figure 8:
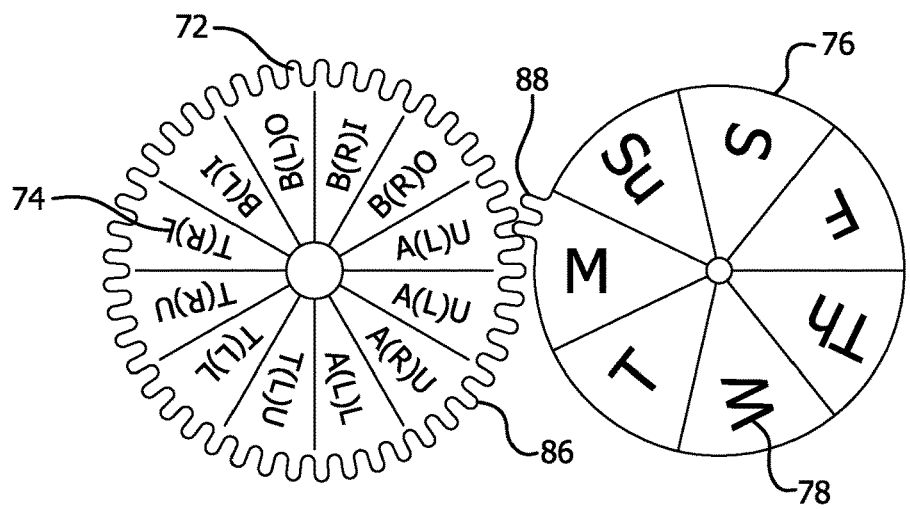
FIG. 8 is a top view of a lost-tooth gearing in accordance with an illustrative embodiment of the present invention.

In addition to a single indicator, embodiments of the present invention can include and additional indicator. For example, as shown in FIGS. 7 and 8, a reminder system 70 includes an indicator 72 with indicia 74 related to injection sites in combination with an additional indicator 76 that has indicia 78 related to days of the week. Alternatively, indicator 76 could have indicia 78 to indicate days of the week in addition to a time of the day. FIG. 7 illustrates the reminder system 70 disposed on a medicament vial 80, and includes a site window 82 and a day window 84.

The indicator 72 is a disc with teeth 86 disposed circumferentially all around the disc, and the additional indicator 76 is a disc with only a few teeth 88 circumferentially disposed. The additional indicator 76 is a lost-tooth gear, as best shown in FIG. 8. For clarity, most of the teeth 86 on the indicator disc 72 are omitted in the figure. In operation, the teeth 88 only engage the teeth 86 during part of the rotation of the additional indicator 76. Thus, during one full rotation of the additional indicator (all seven days of the week) 76, the teeth 88 only engage the teeth 86 to advance the indicator 72 by a single indicium 74. As stated herein, other indicia can be used depending on the desired shot regimen and injection site rotation plan. Also, the reminder system 70 can be used on other drug delivery products such as on a package of syringes or vials, or as a separate handheld device that is apart from a vial or pen (e.g., a portable counter that can have a form factor like a credit card for storage in a wallet or purse or for use as a refrigerator magnet).

In addition to representing sites around the abdomen (e.g., numerals 1, 2, . . . , 12 as described with FIG. 4), indicia 74 on the indicator 72 can represent injections sites at different locations on the body. For example, as shown in FIG. 8, the indicia 74 on the indicator disc 72 represent three general locations (A—abdomen, T—thigh, and B—buttocks), as well as four subdivisions (left (L), right (R), upper (U), and lower (L)) within the general locations as indicated in the following table.

TABLE 1

Illustrative injection site rotation scheme

| Body Area | Body Area Zone | 1 | 2 | 3 | 4 | 5 | 6 | 7 |
|---|---|---|---|---|---|---|---|---|
| Abdomen | (Left) Upper | | | | | | | |
| Abdomen | (Right) Upper | | | | | | | |
| Abdomen | (Left) Lower | | | | | | | |
| Abdomen | (Right) Lower | | | | | | | |
| Thigh | (Left) Upper | | | | | | | |
| Thigh | (Left) Lower | | | | | | | |
| Thigh | (Right) Upper | | | | | | | |
| Thigh | (Right) Lower | | | | | | | |
| Buttocks | (Left) Inner | | | | | | | |
| Buttocks | (Left) Outer | | | | | | | |
| Buttocks | (Right) Inner | | | | | | | |
| Buttocks | (Right) Outer | | | | | | | |

Thus, in this example, the indicia 82 are related to twelve injection sites at different locations on the body.

Figure 9:
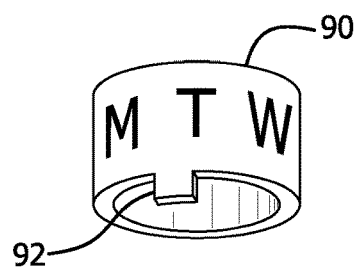
FIG. 9 is a perspective view of a lost-tooth sleeve in accordance with an illustrative embodiment of the present invention.

FIG. 9 illustrates a lost-tooth sleeve 90 that can be employed in embodiments of the present invention. In embodiments in which the lost tooth sleeve 90 is employed with a disc indicator, such as indicator 72 with gear teeth 86 disposed circumferentially all around the disc, the sleeve 90 rotates about a first axis (e.g., a longitudinal axis of a medicament bottle, an injection pen, or an injection pen cap) and the disc indicator 72 rotates about an axis that is substantially perpendicular to the first axis. In this manner, during a complete revolution of the sleeve 90, the tooth 92 only engages the teeth 88 sufficiently to advance the indicator 72 by a single indicium. In such an embodiment, the windows 82 and 84 can be arrayed vertically, rather than the horizontal disposition illustrated in FIG. 7.

Figure 10:
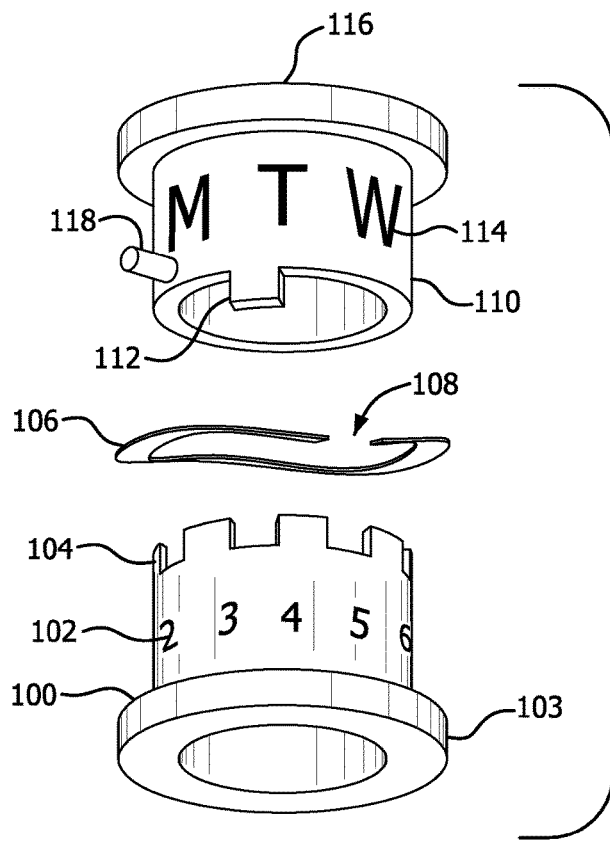
FIG. 10 is an exploded, perspective view of components of a reminder system in accordance with an illustrative embodiment of the present invention.

In addition to being employed with an indicator disc, in embodiments of the present invention, a lost-tooth sleeve can be employed with an indicator sleeve. FIG. 10 is an exploded, perspective view illustrating a hollow indicator sleeve 100, a wave spring 106, and an additional, hollow, lost-tooth sleeve 110 in accordance with an embodiment of the present invention. The indicator sleeve 100 has a plurality of indicia 102 relating to a corresponding plurality of injection sites circumferentially arrayed around the sleeve 100. Additionally, the indicator sleeve 100 includes a distal flange 103 and a plurality of gear teeth 104 disposed on a proximal end thereof. The additional, lost-tooth sleeve 110 includes a gear tooth 112 disposed at a distal end thereof, a plurality of indicia 114 corresponding, for example, to days of the week, a user interface 116, and a follower 118 that will be subsequently explained in greater detail.

Figure 13:
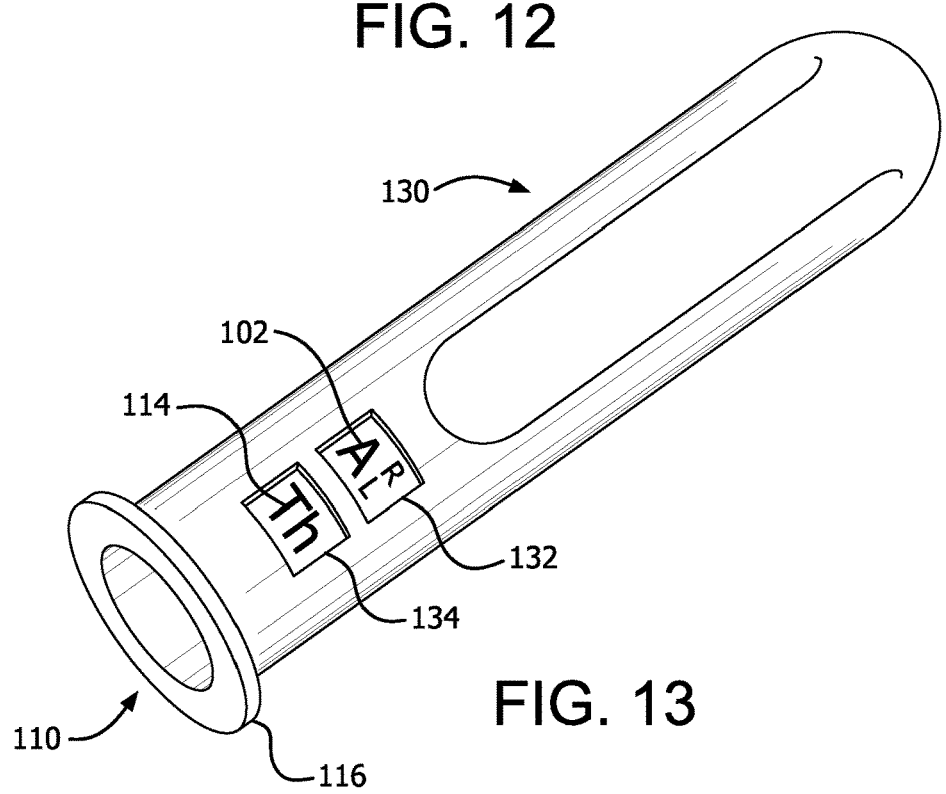
FIG. 13 is a perspective view of an injection pen cap in accordance with an illustrative embodiment of the present invention.

The wave spring 106 includes a gap 108 that surrounds the tooth 112, and is disposed between the indicator sleeve 100 and the additional sleeve 110 to bias the additional sleeve distally, According to one embodiment, a single one of the indicator sleeve indicia 102 and a single one of the additional sleeve indicia 114 are visible at a given time through a window or a plurality of windows on a device, such as an injection pen or an injection pen cap (see, for example, FIG. 13).

Figure 11:
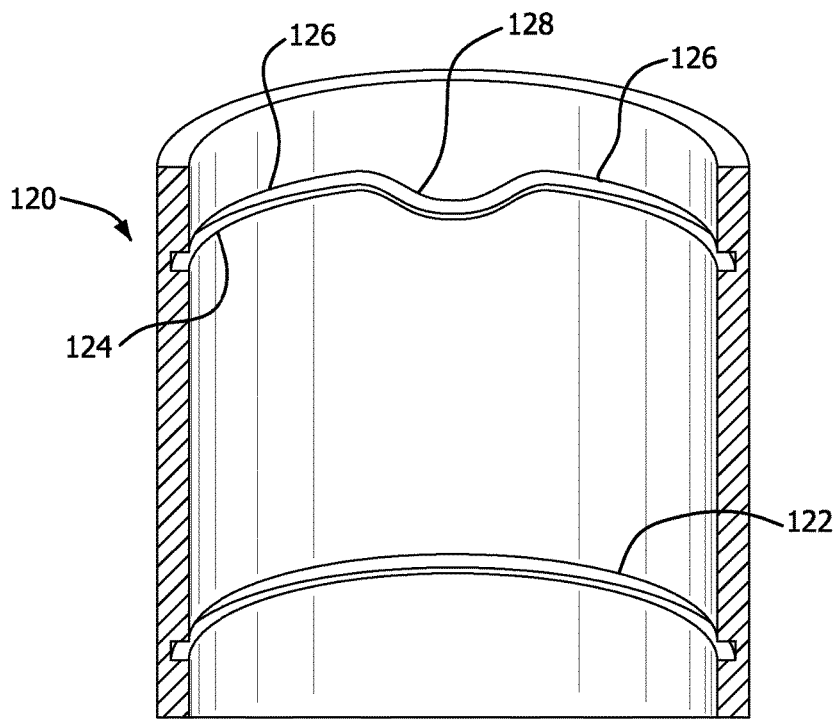
FIG. 11 is a partial, perspective, cross-sectional view of an injection pen in accordance with an illustrative embodiment of the present invention.
Figure 12:
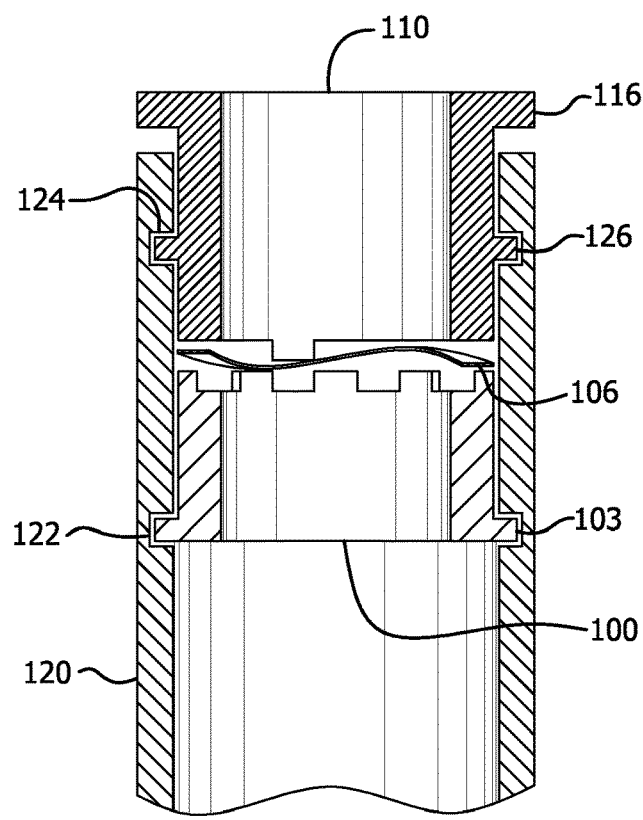
FIG. 12 is a partial cross-sectional view of the pen of FIG. 11.

As shown in FIGS. 11 and 12, an injection pen 120 has a retaining track 122 for rotatably retaining the distal flange 103 of the indicator sleeve 100 and substantially preventing axial displacement of the sleeve 100 relative to the pen 120. One skilled in the art will appreciate that the flange could be disposed on the interior of the pen and a corresponding retaining track could be disposed on the indicator sleeve without departing from the scope of the present invention. The pen 120 also has a cam track 124 for guiding the follower 118.

The cam track 128 includes a first portion 126 that guides the follower 118 (and thus the lost tooth sleeve 110) in a substantially planar manner. While the lost tooth sleeve 110 is rotating with the follower disposed in the first portion 126, the bias of the wave spring 106 prevents the lost tooth sleeve 110 from contacting the indicator sleeve 100. In other words, the bias of the wave spring 106 prevents the additional sleeve gear tooth 112 from engaging the indicator sleeve gear teeth 104 when the follower 118 is travelling in the plane defined by the first portion 126 of the cam track 124. In contrast, when the follower 118 travels in a second portion 128 of the cam track 124, the follower 118 (and thus, the lost tooth sleeve 110) overcomes the wave spring bias, displaces distally, and the gear tooth 112 engages one of the gear teeth 104. Upon continued rotation of the lost tooth sleeve 110, because of the engagement of the gear teeth, the lost tooth sleeve 110 advances the indicator sleeve 100 by a single indicium, the gear teeth disengage, and the follower returns to travelling in the first portion 126 of the cam track 124.

Although a single follower 118 and single second portion 128 are illustrated for clarity, one skilled in the art will appreciate that a plurality of followers 118 and a corresponding plurality of second portions 128 can be employed without departing from the scope of the present invention, and can enhance the stability of the additional sleeve's travel, and provide a smoother path as well. For each follower, there is a corresponding plurality of indicia. For example, in an embodiment with two followers 118 and two second portions 128, two weeks of indicia are arrayed around the lost-tooth sleeve 110. In such an embodiment, one half of a rotation of the lost-tooth sleeve 110 passes through a week and advances the indicator sleeve 100 by a single indicium. One skilled in the art will also appreciate that the follower(s) can be disposed on the interior of the pen and a corresponding cam track could be disposed on the additional or lost-tooth sleeve without departing from the scope of the present invention. One skilled in the art will also appreciate that additional sleeves can be disposed on the device with a corresponding cam track to indicate a third set of indicia.

According to one embodiment, advancing the lost-tooth sleeve 110 by a single indicium generates audible and/or tactile feedback for the user. One skilled in the art will appreciate that any number of mechanisms can be employed to provide such feedback without departing from the scope of the present invention. Additionally, such mechanisms can aid in more precisely positioning indicia adjacent to a viewing window. Mechanisms such as odometer-type mechanisms employing an additional gear could be utilized to provide the intermittent motion of the second and subsequent rings.

For example, the lost-tooth sleeve 110 and related mechanical components illustrated in FIGS. 10-12 for advancing the indicator sleeve 100 can be replaced by an electronic display 214, and electromechanical and/or electronic means can be used in the pen for tracking injection sites (e.g., whenever the user interface is turned or pushed prior to an injection) and providing microswitch 210 output signals to the display 214 (e.g., having an integrated controller) or a separated processor (not shown) connected to the microswitch and the display, as illustrated in FIGS. 22A through 22C. The casing of the pen 120, for example, can be provided with a microswitch 210 on its interior that operates in conjunction with an actuator 212 provided on the user interface 116 or a plunger, which can be an indentation or groove or other means to provide a force to a button or lever on the microswitch 210 each time the pen is used for an injection. In response to movements of the user interface 116 and corresponding activations of the microswitch 210, previous injections sites can be tracked (or at least counted), and a display 214 can be controlled to change whenever the next injection site needs to be displayed in accordance with a selected site rotation plan (e.g., show one of the 12 locations in Table 1 and a corresponding day of the week, or show a number 1 through 12 representing injection locations around the umbilicus). The display 214 can be one or more display screens or windows in the casing of the pen. Alternatively, the microswitch 210 or other electronic or electromechanical means for advancing the display can be provided on the outer surface of the user interface 116 that slidably engages the interior of the pen 120, and the aforementioned corresponding actuator 212 can be provided on the interior of the pen casing.

FIG. 13 illustrates a reminder system similar to that shown in FIGS. 10-12, except that it is inverted and disposed in an injection pen cap 130. The cap 130 includes windows 132 and 134 for viewing the indicia 102 and 114. The user interface 116 extends from the proximal end of the cap 130. Alternatively, the cap can be provided with electronic or electromechanical means (e.g., a microswitch 210 on the outer surface of the pen that slidably engages the interior of the pen cap), and the aforementioned corresponding actuator 212 provided on the interior of the pen cap) to cause changes to the display(s) 102 and 114 in accordance with a selected site rotation plan. Alternatively, the locations of the microswitch 210 and actuator 212 can be reversed (e.g., the actuator on the outer surface of the pen that slidably engages the interior of the pen cap, and the corresponding microswitch on the interior of the pen cap).

With reference to FIG. 22C and in accordance with illustrative embodiments of the present invention, the display 214 on the pen cap 136 can indicate a target injection site that is automatically advanced upon detection of the pen being recapped. For example, the display 214 can indicate "SITE 1" according to a selected site rotation plan. After the cap 136 has been removed and an injection made, the pen 120 is recapped. The operation of the microswitch 210 and actuator 212 provided on respective ones of the pen cap 136 and the exterior of the pen casing cause the display 214 to be automatically advanced to indicate the next target injection site "SITE 2". Other displayed indicia can be used to represent the next target injection site based on the injection rotation plan used by the patient. The pen 120 can be pre-configured or configurable to display target injection sites in accordance with a designated injection site rotation plan and indicia representing the target sites.

Figure 14:
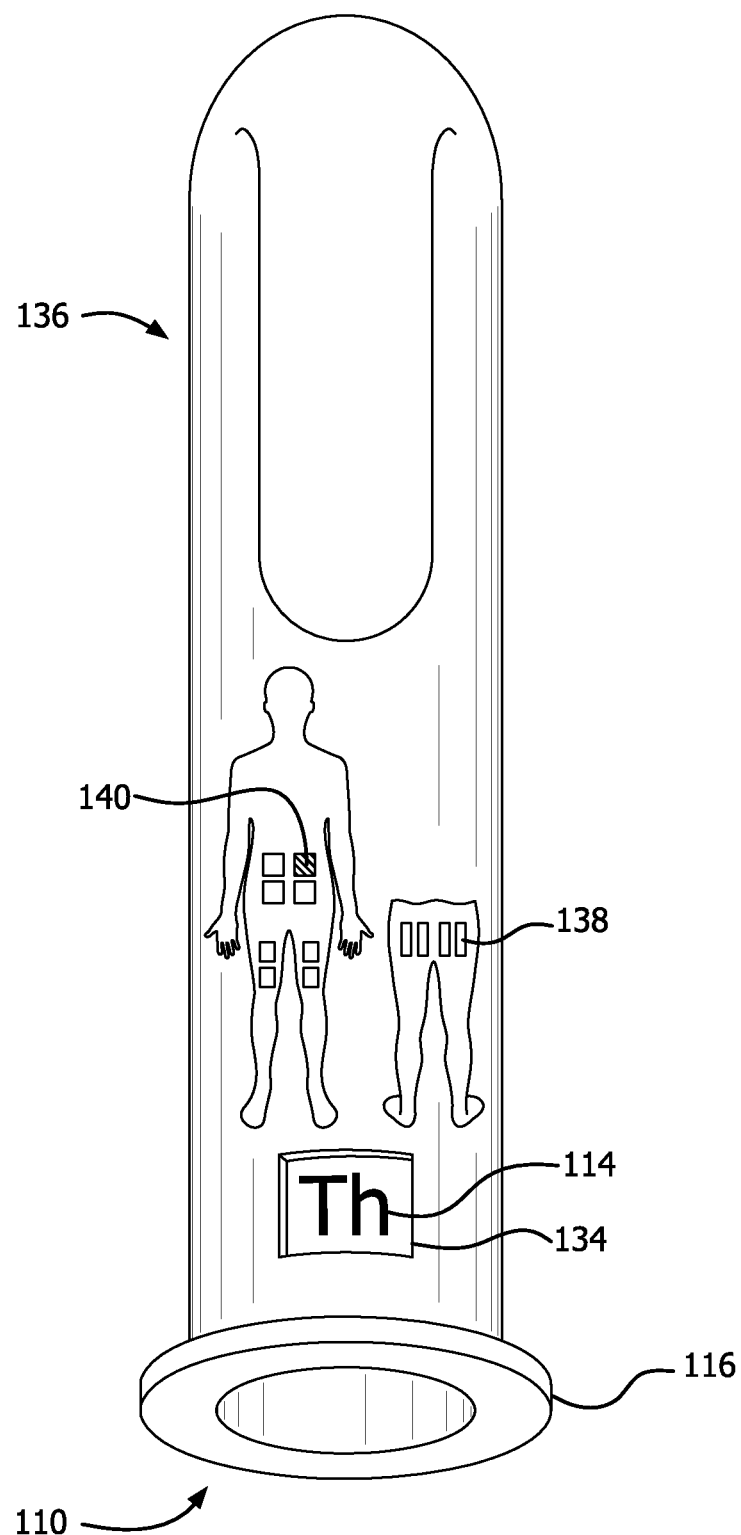
FIG. 14 is a perspective view of another injection pen cap in accordance with an illustrative embodiment of the present invention.
Figure 15:
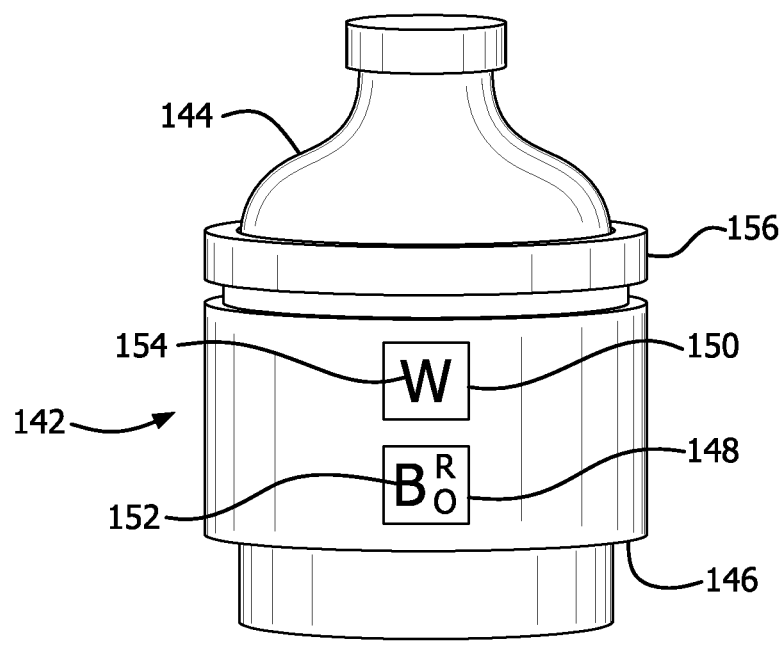
FIG. 15 is a perspective view of a medicament vial in accordance with an embodiment of the present invention.

FIG. 14 illustrates another illustrative embodiment of a reminder system in an injection pen cap 136. The cap 136 is similar to the cap 130 in many respects; for example, the user interface 116 extends from the proximal end of the cap 130, and the window 134 displays the indicia on the lost-tooth sleeve 110. In contrast, however, the cap 136 includes a plurality of windows 138 that graphically correspond to body areas for injection, and rather than being alpha-numeric, the indicia 140 on the hollow indicator sleeve are simply a shaded or colored area. In operation, rotation of the lost-tooth sleeve 110 through a set of indicia (for example, one week), advances the indicator sleeve to indicate a different body area. For example, the shaded or colored indicia 140 could advance from a window 138 representing the right, upper abdomen to a window 138 representing the left, upper abdomen.

Such an embodiment can reduce the number of indicia on the indicator sleeve, depending on the sequence of body areas, because the same indicium can be used in at least two windows. For example, for the windows representing the front of the body, a single indicium 140 can be visible through a window 138 representing a given right body area (upper abdomen, lower abdomen, upper thigh, or lower thigh), and then, upon counter-clockwise rotation of the lost-tooth sleeve 110 and advancement by the selective contact between the tooth 112 on the lost tooth-tooth sleeve 110 and the teeth on the indicator sleeve, the same indicium 140 can be visible through the window 138 representing the corresponding left body area (upper abdomen, lower abdomen, upper thigh, or lower thigh). Further, assuming a sequence of buttocks areas of outer right, inner right, inner left, and outer left, a single indicium 140 can be sequentially visible though the corresponding windows 138. One skilled in the art will appreciate, however, that other body area sequences can be employed without departing from the scope of the present invention. Additionally, the display may be implemented electronically.

Similar to the reminder system shown in FIGS. 10-12, FIG. 15 illustrates a reminder system 142 disposed on a medicament vial 144. Such an embodiment can be useful for patients that use syringes and a medicament vial rather than an injection pen. According to one embodiment, the reminder system 142 is fixedly secured to the medicament vial 144. According to another embodiment, the reminder system 142 can be removed from the vial 144 and attached to another vial to be re-used.

The reminder system 142 includes housing 146 with windows 148 and 150 for viewing the indicia 152 and 154 on the hollow indicator sleeve and the hollow, additional or lost-tooth sleeve, respectively. In use, similar to the reminder system shown in FIGS. 10-12, the user rotates a user interface 156 to sequentially show the indicia 154 through the window 150, and upon a complete cycle of the indicia 154, the indicator sleeve is advanced to show the next sequential indicium 152 through the window 148.

Figure 16:
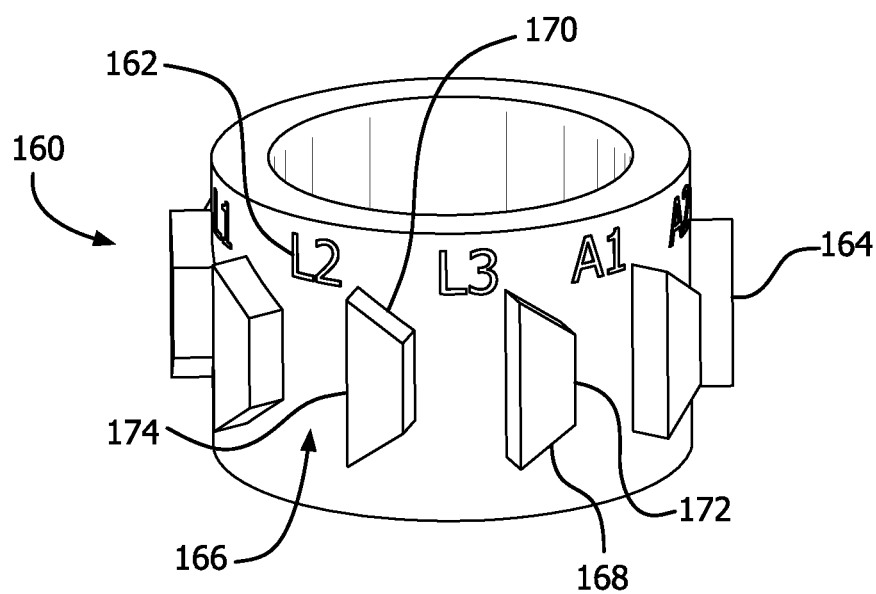
FIG. 16 is a perspective view of an indicator sleeve in accordance with an embodiment of the present invention.

FIG. 16 illustrates a hollow indicator sleeve 160 in accordance with an embodiment of the present invention. The indicator sleeve 160 includes a plurality of indicia 162 arrayed circumferentially, and a corresponding plurality of radial protrusions 164 arrayed circumferentially. The space between adjacent radial protrusions 164 forms a slot 166. According to on embodiment, the radial protrusions 164 are substantially trapezoidal, having a first angled surface 168, a second angled surface 170, and a pair of parallel sides 172 and 174 that are substantially aligned with the longitudinal axis of the hollow indicator sleeve 160.

Figure 17:
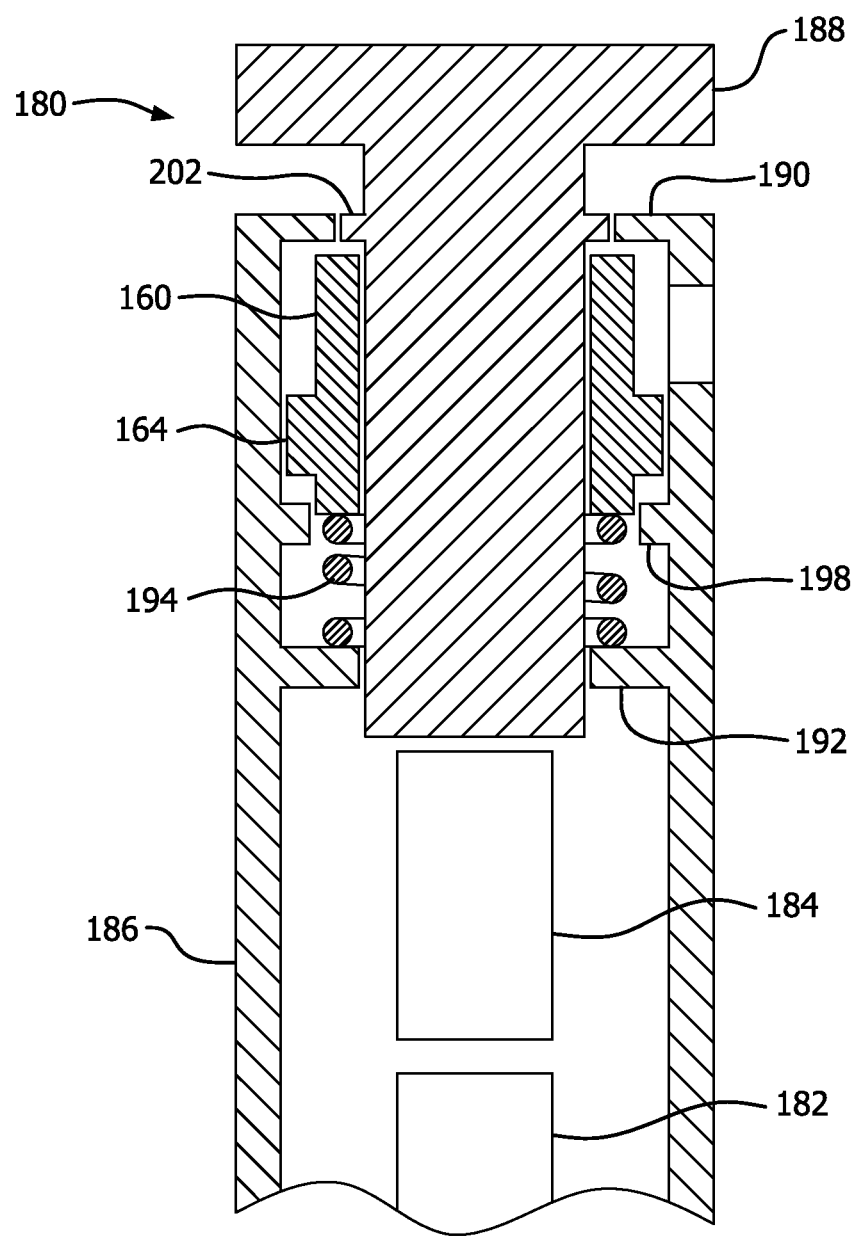
FIG. 17 is a partial, cross-sectional, schematic view of an injection pen in accordance with an illustrative embodiment of the present invention.
Figure 18:
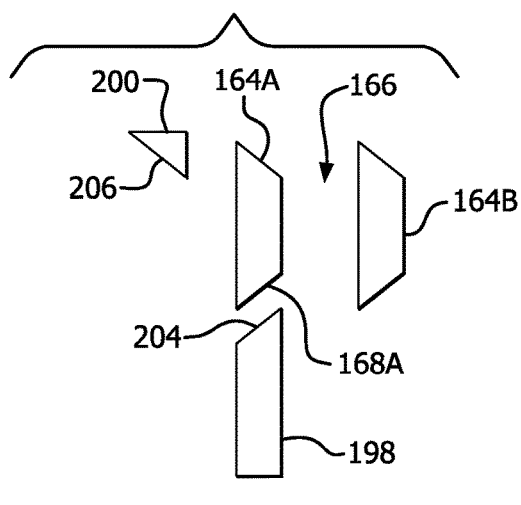
FIGS. 18-21 are diagrams illustrating operation of the injection pen of FIG. 17.
Figure 19:
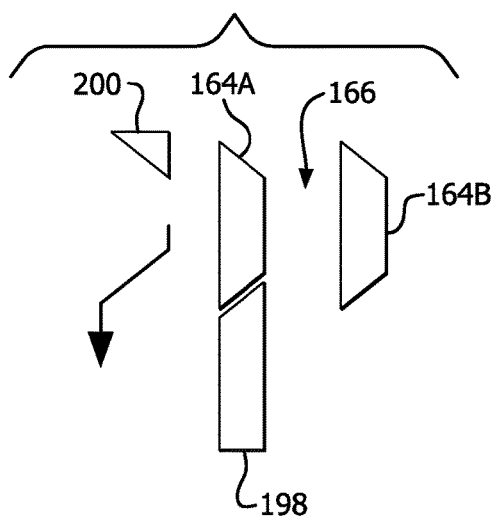

FIG. 17 is a partial, cross-sectional, schematic view of an injection pen 180 incorporating the indicator sleeve 160. The pen 180 includes a medicament cartridge 182 and a dosing mechanism 184, both of which are shown schematically for clarity. The pen 180 also includes an outer case 186 and an injection button 188 for setting the dose (in conjunction with the dosing mechanism 184) and injecting the medicament.

The outer case 186 includes a proximal flange 190 that prevents the indicator sleeve 160 from proximally exiting the pen 180. The case 186 also includes a shelf 192 that protrudes radially inward and supports a biasing element (such as a spring) 194, which proximally biases the indicator sleeve 160. In addition, the case 186 includes a primary advancing protrusion 198 (shown in FIG. 17) and a secondary advancing protrusion 200 (shown in FIGS. 18-21), which are circumferentially and axially offset form each other. Further, both advancing protrusions 198 and 200 protrude radially inward.

Figure 20:
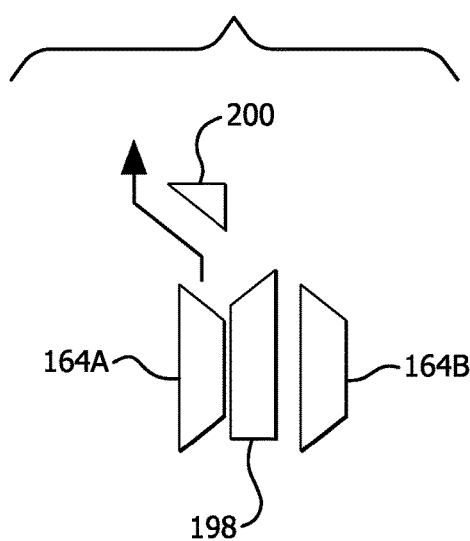

Referring to FIGS. 16-21, as the user depresses the button 188 distally, a button flange 202 engages the proximal end of the indicator sleeve 160 to displace the indicator sleeve 160 distally and overcome the force of the biasing element 194. For illustrative purposes, in FIGS. 18-21, two adjacent indicator sleeve radial protrusions 164 are referred to as protrusions 164A and 164B. As the first angled surface 168A of the protrusion 164A is displaced distally, it engages and slides against the proximal angled surface 204 of the primary advancing protrusion 198 (FIGS. 18 and 19), to rotate the indicator sleeve 160 and align a slot 166 with the primary advancing protrusion 198 (FIG. 20).

Figure 21:
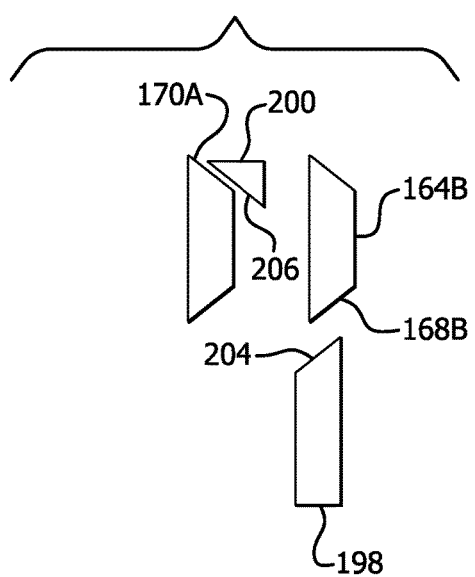

Subsequently, once the user releases the button 188 after finishing the injection, the biasing element displaces the indicator sleeve 160 proximally. During this proximal displacement (FIGS. 20 and 21), the second angled surface 170A engages and slides against a distal angled surface 206 of the secondary advancing protrusion 200, to further rotate the indicator sleeve 160. This further or secondary rotation of the indicator sleeve 160 aligns the next indicium 162 with a viewing window (not shown), and aligns the adjacent protrusion 164B, so that upon the next depression of the button 188, the first angled surface 168B will engage and slide against the proximal angled surface 204 of the primary advancing protrusion 198 (FIG. 21).

The embodiment shown in FIGS. 16-21 can be useful for changing the body area for each injection. Additionally, by repeating indicia 162, a particular body area can be visible through the viewing window for a given number of injections before a different body area is visible through the viewing window. A similar sequential advancing mechanism is described in commonly-assigned U.S. Pat. No. 7,597,853, which is hereby incorporated by reference in its entirety.

As exemplified herein, illustrative embodiments of the present invention provide users of injection pens or vials with different injection site tracking and/or reminder methods and apparatuses to recollect where the last injection was administered and/or be advised where to locate the next injection site, or when to rotate to a new body area and/or body area section or zone.

Single Dose Syringes or Vials or Other Devices and Related Packaging

Many diabetic patients choose to administer their insulin using disposable, pre-measured single dose syringes, or single or multiple dose vials of insulin for use with a pen needle assembly. Example pens are illustrated in FIGS. 1-2 as described above. The following illustrative embodiments help patients follow an injection site rotation plan using the insulin product packaging such as boxes, cartons or other containers comprising disposable supplied such as pen needles, unit dose syringes or vials.

In one embodiment of the invention, the packaging for the insulin delivery devices provides instructions and recommended guidelines to assist the patient in selecting a body area and/or an injection site within the body area to reduce the risk of lipohypertrophy. The packaging can have a variety of forms and shapes with preprinted labels or indicia on the cover, or other surfaces of the packaging for the insulin delivery devices, or as a printed insert placed in or on the packaging, or on each of the insulin delivery devices stored within the packaging. The packaging typically contains a number of insulin vials, ampoules, prefilled syringes, injection pens or other single use insulin delivery devices. Indicia on the insulin delivery devices are preferably coordinated with the packaging to encourage rotation and relocation of the body area injection site to reduce the occurrence of repeated injection in the same or similar area or injection site of the patient. It is generally recommended that sequential injection sites be spaced apart a distance sufficient to reduce the risk of lipohypertrophy (e.g., 1-2 centimeters apart, or one to two finger widths apart).

Figure 25A:
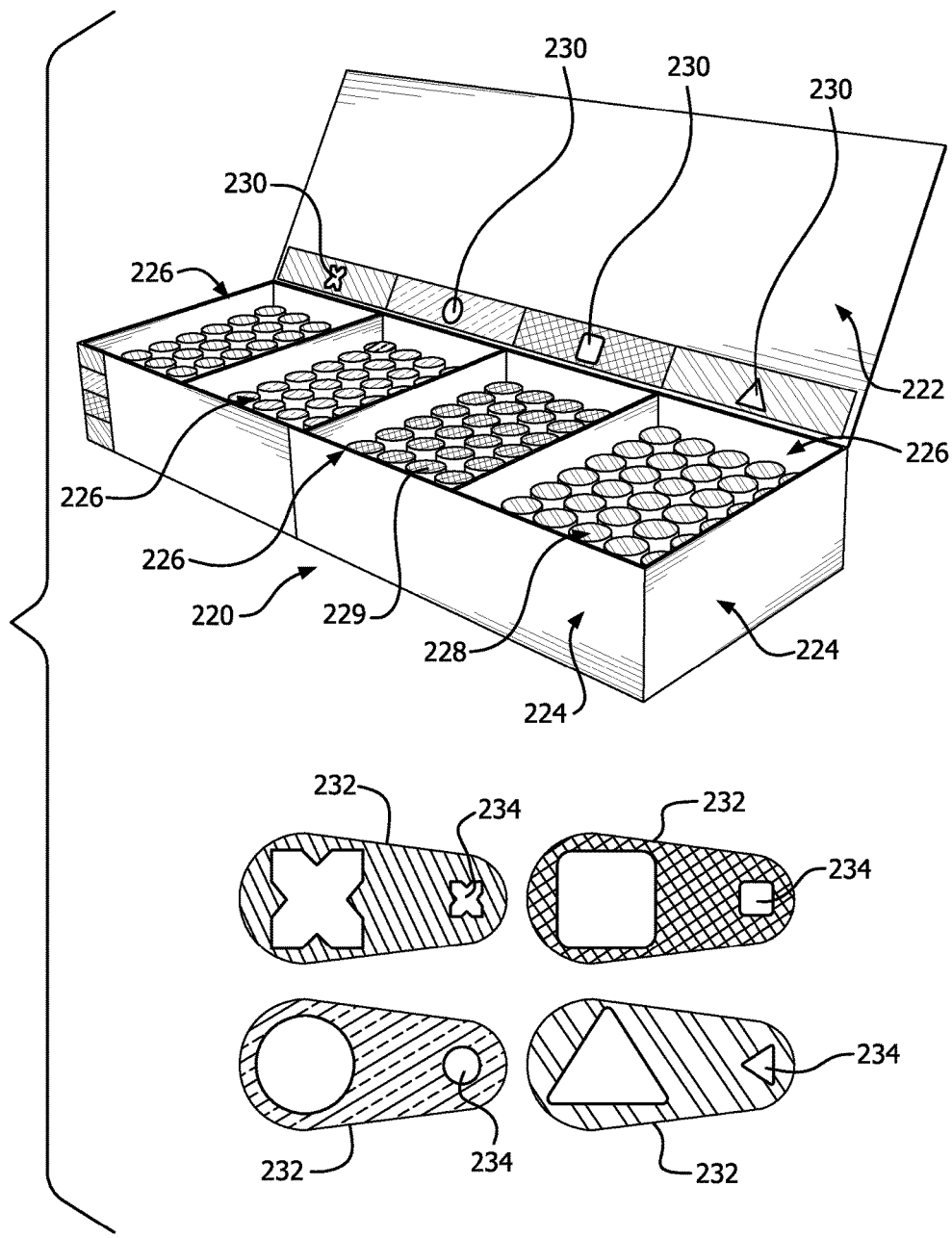
FIGS. 25A and 25B depict a package (e.g., of injection supplies) having instructions in the form of printed indicia providing the instructions, guidelines and recommendations for the rotation of injections among body areas or the target injection sites within a body area in accordance with illustrative embodiments of the present invention.

Referring to the drawings, a package can be produced for shipping and storing insulin vials, ampoules or other single use delivery devices. In the embodiment shown in FIGS. 25A and 25B, the package 220 is a box having a lid 222 or other surface which can have instructions in the form of printed indicia providing the instructions, guidelines and recommendations for the rotation of injection sites within a body area. In the embodiment shown, the instructions can be preprinted on a surface of the package such as on the interior of the lid 102 or on a side 104 of the package. Instructions can be, for example, all or part of the instructions illustrated in FIGS. 40A through 40F, or indicia or patterns (e.g., different colors and/or shapes) on the package box 220 and stickers or labels on individual delivery devices (e.g., pen needles, vials, syringes) 228 stored in the box 220 that correspond to box compartments 226, or chart or other storage arrangement to facilitate reminding a user to rotate or otherwise intersperse injection sites within a body area and/or among plural body areas each time a delivery or injection device 228 is removed from the package 220 for use.

The package 220 in the embodiment shown is divided into four compartments 226 for storing and shipping the insulin injection devices 228 (e.g., vials, single dose syringes, pen needles, and so on). It is to be understood that the compartments can be separated by physical dividers 229 in the package, or on the basis of coding of the packaging 220 and/or the devices 228. Each compartment 226 can contain the same or a different number of the insulin delivery devices 228. The compartments are identified according to the location of a recommended body area or the injection site within a body area on the patient according to the injection protocol. The compartments 226 have suitable indicia 230 or other visual indicator corresponding to a predetermined body area or injection site on the patient. The compartments 226 can be color coded as shown with different colors or hues or printed patterns that enable the patient or technician to quickly and easily select an insulin delivery device 228 by color for a designated body area or target injection site corresponding to that color. The individual compartments 226 and the insulin delivery devices 228 can have coordinating colors and/or labels 232 so that the insulin delivery device 228 has the same identifying indicia, color or markings as the corresponding compartment 226 in which it is stored before use. In the embodiment shown, each of the compartments 226 has a different color such as for example red, blue, green and orange. Preferably, the colors and shades are selected to be visually distinguishable to the average user and color blind users.

The compartments 226 with the insulin injection devices 228 and the corresponding colors are preferably designated to correspond to a different body area or region on the patient such as, for example, the abdomen 32, one or both legs or thighs 34, one or both buttocks 36, or one or both arms 38, or to any other suitable area on the patient, as illustrated in FIGS. 23A and 23B. The different compartments 226 of the package 220 can also be identified by distinctive markings 230 such as a geometric shape or design assigned to either a body area or the injection site within the body area. Preferably, each insulin injection device 228 includes the same or similar markings corresponding to the designated compartment 226 in the package 220 in which it is stored or otherwise contained. In the embodiment shown, the four compartments 226 include markings 230 identified by an X, circle, square and a triangle, although other shapes and designs can be used either alone or in combination. Preferably, each of the individual insulin injection devices 228 includes a label 232 as shown where the label is color-coded and includes one of the geometric design markings 234 corresponding to the respective marking 230 of the compartment 226 in which the device 228 is stored prior to use. The labels 232 are preferably attached to the individual insulin injection device 228 or a container for the insulin delivery device by an adhesive. In one embodiment, the adhesive is a pressure sensitive adhesive that allows the label 232 to be removed and reapplied as needed.

During use, the patient identifies each of the colors and geometric markings as corresponding to a selected body area or injection site of the patient for injecting the insulin. The patient is able to select an insulin injection device 228 from a particular compartment 226 to monitor the number of injections in the particular injection site or body area and to encourage selecting an alternate injection site or body area to avoid repeated injection within the same body area or injection site. As each of the insulin injection devices 228 are used and discarded, the remaining insulin injection devices 228 within the packaging 220 and the respective compartments 226 provide an indication or record of the number of injections in the particular injection area or injection site identified by the color and/or marking 234.

Figure 37:
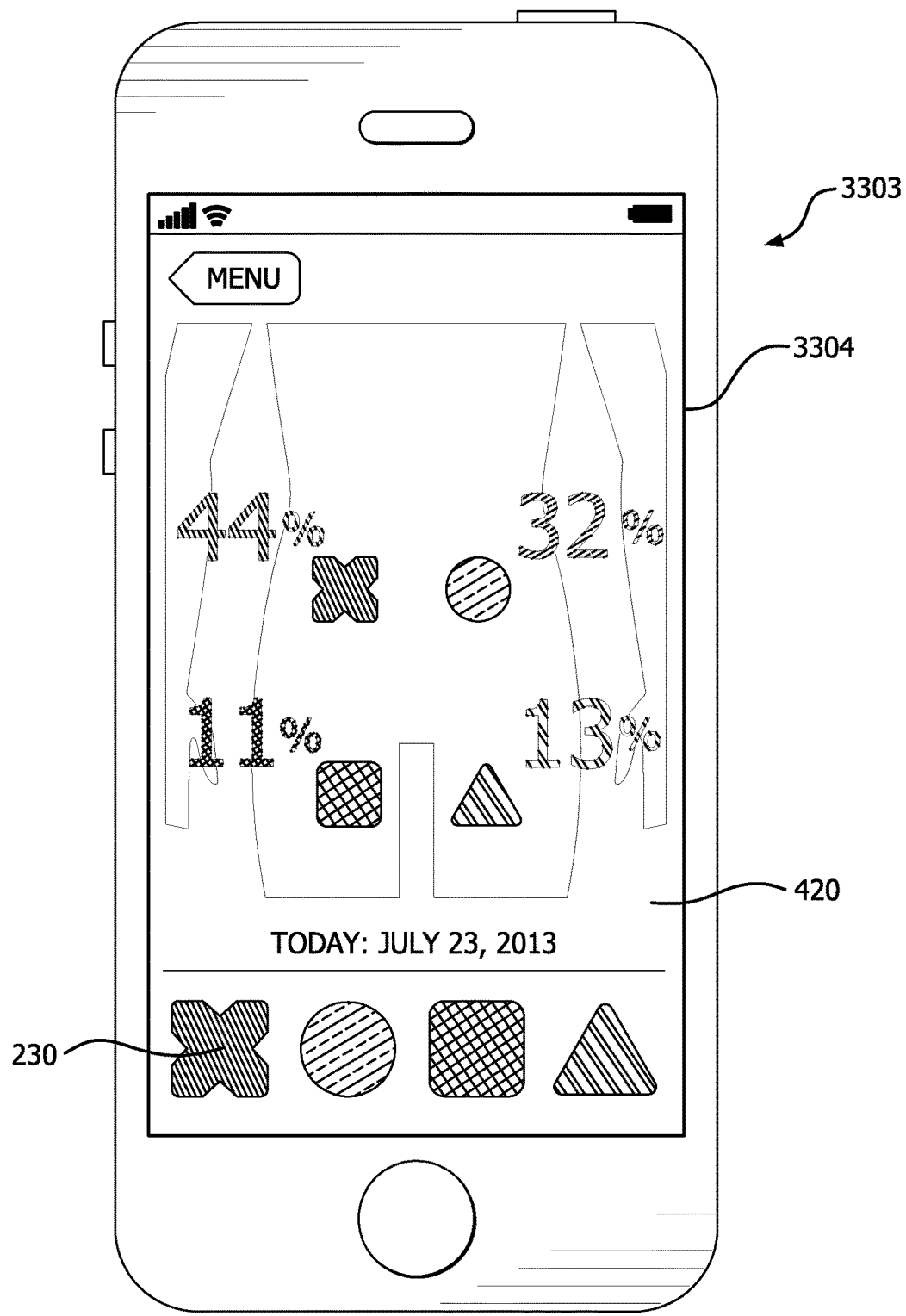

With reference to FIG. 37, a mobile phone app can also be provided for downloading onto a user's phone and used in conjunction with the coding scheme of the packaging 220 as described below.

Figure 25B:
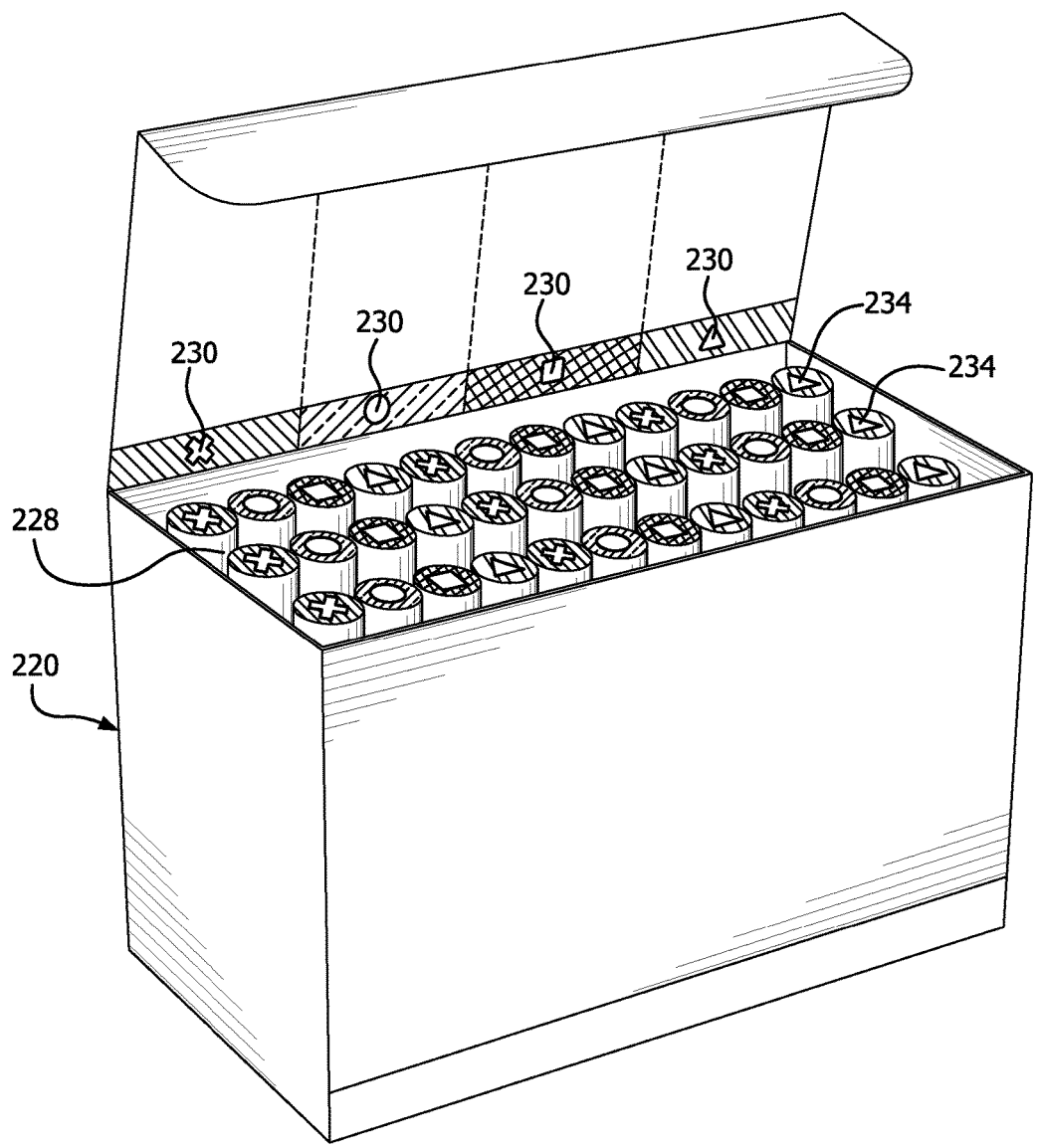
Figure 25B:
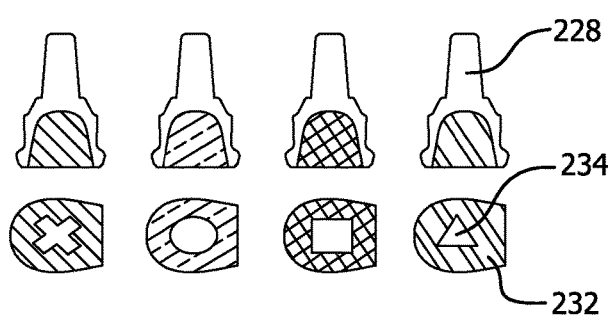

In another embodiment the package 220 can include indicia and/or colors 230 to identify a specific body area, such as for example, the legs, arms, and abdomen. The packages 220 can contain a plurality of insulin injection devices 228 having various markings for identifying specific injection sites within the body area. In the embodiment as shown in FIG. 25B, the packaged insulin injection devices are positioned in rows and columns by dividers within the package 220. The injection devices can be aligned in a row corresponding to a particular day of the week, for example. The columns can correspond to the number of injections per day, for example, and can include indicia corresponding to the recommended injection site to provide the desired rotation or sequential movement and relocation of the injection sites. Different configurations for arranging injection devices 228 within the compartments 226 or simply within the package 220 (e.g., rows and columns) can be used to facilitate guiding a user to employ a particular device 228 at a selected injection site within a selected body area at a designated date and/or time (e.g., different numbers of compartments, and/or rows and columns, depending on the injection regimen).

Figure 26:
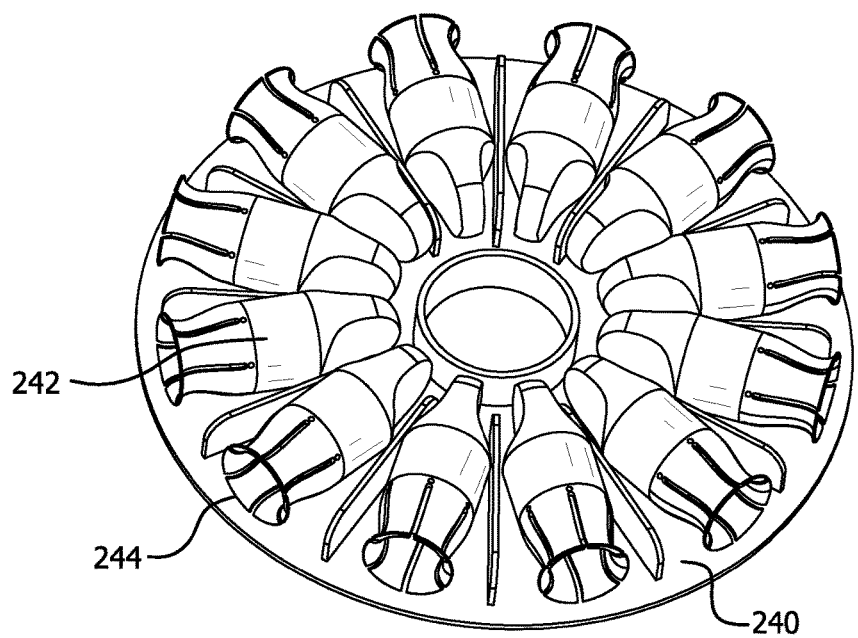
FIG. 26 depicts a package divided into separate compartments corresponding to a selected injection site or injection area in accordance with an illustrative embodiment of the present invention.

In another embodiment shown in FIG. 26, the package 240 is divided into separate compartments or sections 242 configured to each receive or otherwise store a delivery device (e.g., pen needles or ampoules which are not shown) 228 such that the devices are arranged corresponding to a selected pattern of injection sites. For example, with reference to FIGS. 3, 24 and 29 where the abdomen 32 is the designated body area to receive injections, the regimen may require dispersing injection sites along radii of one or more concentric circles centered on the umbilicus 42. The radii can correspond to the hours of a clock or compass zones or other pattern. As shown, the compartments 242 are identified by indicia or markings 244 (e.g., numbers 1 through 12 corresponding to the hours on clock) depicting the recommended location for the injection site to encourage rotation and selection of a different injection site for each subsequent insulin injection by simply removing the device from a compartment and administering the injection at a point on the abdomen that is referenced relative to the compartment (e.g., the compartment labeled with "12" can be held at the top of the umbilicus 42 to determine the injection site for the device in compartment currently in use). The insulin injection devices (e.g., the pen needles or ampoules) 228 can be optionally provided with a respective label that has the same indicia or markings corresponding to the indicia 244 on the package 240 for the respective compartments 242 in which the devices are stored or arranged.

Figure 27A:
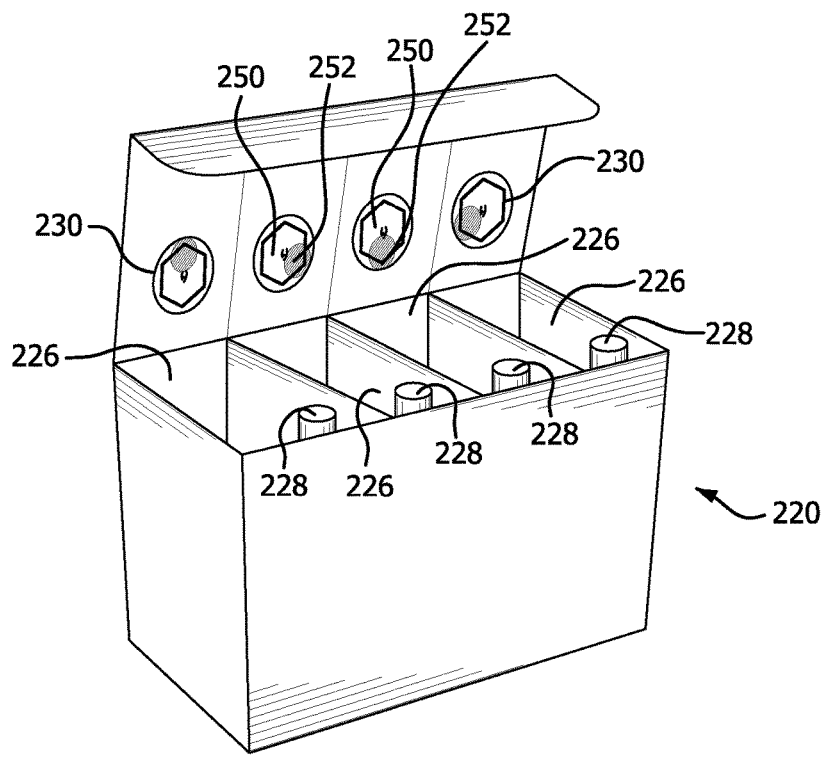
FIGS. 27A and 27B depict printed indicia on packages and on stickers applied to pen caps, syringes or other individual injection devices that can identify an injection site at an upper region, a lower region, a right side and a left side of a user's abdomen to encourage injection site rotation in accordance with an illustrative embodiment of the present invention.
Figure 27B:
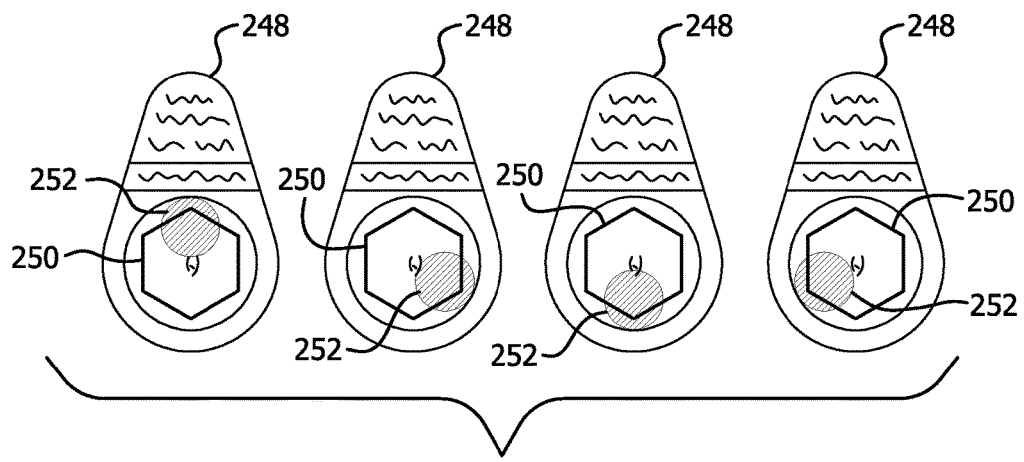
Figure 28:
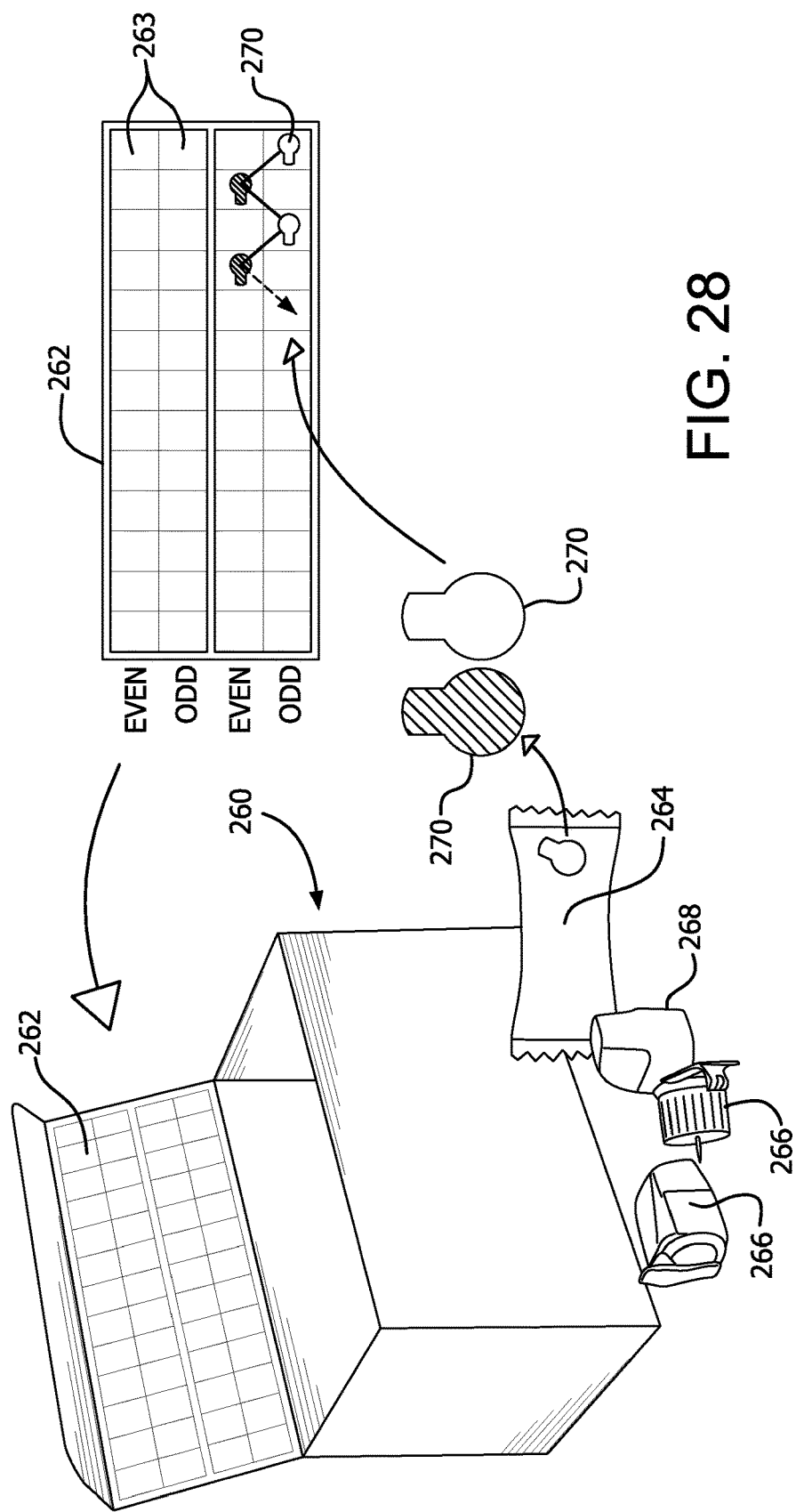
FIG. 28 depicts a package having a chart printed on the package or as a removable card and corresponding injection device indicia for recording and tracking the injection sites accordance with an illustrative embodiment of the present invention.

In accordance with another illustrative embodiment shown in FIGS. 27A and 27B, indicia or markings 250, 252 depict a specific injection site which can be within a designated body area. The package 220 can be designated for a particular body area (e.g., the abdomen 32) so that the compartments 226 and the respective indicia 230 correspond to the recommended sequential injection sites 252 within that body area 250. In the examples shown, the compartments 226 are given a marking 230 which provides a site map for an injection site 252 in a designated body area 250 such as, for example, the abdomen 32. Similarly, the injection devices 228 stored in the respective compartments can be provided with labels 248 or other medium having indicia (e.g., a site map) showing the injection site 252 within the body area 250. The site map provided by the indicia 230 and labels 248 divides the body area 250 into a predetermined number of segments corresponding to an identifiable injection site 252. In the embodiment shown, the indicia or markings 250 are a hexagon-shaped site locator map where each point corresponds to a location around the abdomen 32 to identify an injection site 252. Each point can be identified by a circle 252, color or other visual marking to identify the recommended injection site. In the embodiment shown, the package 220 has four compartments 226 so that four points are identified on the labels 248 corresponding to the injection site around the abdomen. The points on the hexagon can identify an injection site at an upper region, a lower region, a right side and a left side of the abdomen as shown in FIGS. 27A and 27B. The geometric shape can have the same number of identifying locations 252 corresponding to the number of compartments 226 in the package. Although four compartments are shown, the package 220 can have six compartments 226 corresponding to the number of available injection sites or points on the indicia represented by the hexagon in the illustrated example. In another embodiment of the invention, the package 260 as shown in FIG. 28 is provided with a chart 262 printed on the package or as a removable card for recording and tracking the injection sites. By recording each injection site, the patient is able to avoid or reduce the risk of injecting into the same site repeatedly and select a different injection area or injection site for each subsequent injection. The patient can have a predetermined order or location of the injection sites that can be translated and recorded onto the chart 262 to record the sequence, location and rotation of injection sites. By way of example shown in FIG. 29, the abdomen 32 is the designated body area which can be divided into 12 injection sites 272 representing a clock face where each imaginary clock face number is used to identify an injection site. Alternatively, the injection sites 272 can be oriented as concentric circles as in FIG. 24. The chart 262 can be divided into a number of injection sites where each space 263 on the chart corresponds to the desired injection site. The insulin delivery devices 266 (e.g., pen needles 266 which can have a cover 268), or packaging 264 for enclosing one of the individual insulin delivery devices 266 (e.g., with its cover 268), are provided with a removable tab or label or sticker 270 to indicate the intended injection site. The tab or label 270 is removed by the patient at the time of use and attached to the chart 262 to provide a continuous record of the injection sites. The label 270 can be printed with the recommended injection site or provided with a writing surface where the patient can write directly on the label to record the injection site, date, time or other desired information pertaining to the injection and the injection site. The label 270 is then attached to the chart 262 to record the injection history.

For example, in one embodiment as shown in FIG. 28, the chart 142 includes a plurality of spaces arranged in rows corresponding to the even number and odd numbers of the image of the clock face on the injection area of the abdomen. The injection site can be selected corresponding to an even number or an odd number of the image of the clock face and then the label 270 is removed from the insulin delivery device 266 and adhered to the chart 262 in a row corresponding to the even number or odd number. The chart provides a visual record of the sequence of injection site locations. In other embodiments, the chart 262 can be provided with a row or column corresponding to each of the numbers of the clock face image or other pattern identifying the injection sites of the designated injection area. The chart 262 can be printed directly on the package such as on the inside surface of the lid or any convenient location that is accessible by the patient. Alternatively, the chart 262 can be separate from the package and carried by the patient and stored in a selected location. The chart 262 can have can have various rows and columns to identify the day of week, the body area of the injection, the injection site within the body area and other information relating to the injection sites to assist the patient in recording the previous injection sites and select an injection site spaced from previous injection site a distance to prevent injecting in the same site.

Body Stickers

In accordance with illustrative embodiments of the invention, labels or stickers or other markers can be provided for adhesion to the patient's skin at an injection site instead of to a chart (e.g., chart 262 in FIG. 28). Thus, the user has an accessible visual record of previous injections sites and guidance for locating target injection sites.

With reference to FIG. 30, an indicator 280 is provided which can be adhered to a patient's skin. The indicator 280 can be, for example, a sticker with an adhesive backing for application to a user's skin. The sticker can use a medical grade adhesive that allows the sticker to remain on for most user activities but also allows the sticker to be removed when desired by the user.

The indicator 280 can be a multiple ply sticker, that is, where each ply 281 is removably adhered to another ply 281 beneath it (e.g., overlapping plies 281a, 281b, . . . 281g). Each ply can be provided with indicia (e.g., printed indicia on the ply, or a punched hole through the ply) corresponding to respective site locations.

For example, the sticker 280 can be provided with a number and selected arrangement of holes 282 that correspond to the grid or pattern of injection shots to be distributed to the body area beneath the sticker when it is adhered to the skin of the user. For example, the sticker 280 can define a circular distribution area for injection sites with seven holes 282 arranged in a circle. The arrangement of the holes 282 can be identical on each ply 281, and the plies 281 aligned with respect to teach other, so as to align the holes of each ply and accommodate the insertion of needle or catheter of the drug delivery device in the aligned holes and into the injection site underneath.

With continued reference to FIG. 30, each ply 281 provided with a printed indicia 284 with respect to one of its holes to represent a target hole 282 and corresponding target injection site associated with that ply. The printed indicia 284 is associated with a different one of the holes 282 in each ply 281. Once an injection is administered through the hole with printed indicia 284 in the top most ply, that ply is removed before the next shot. The underlying ply 281 then guides the user to next inject via a different hole as indicated by its corresponding printed indicia.

The number of plies 281 in a sticker 280, and the number of holes 282 in each ply 281 can differ, depending on the injection regimen and injection site rotation plan. Further, the arrangement of holes 282 and/or printed indicia 284 on each ply 281 can vary depending on the desired injection site distribution pattern (e.g., sites arranged in a grid or matrix, or sites spaced apart from each other along a circle or spiral line) for the body area beneath the sticker 280 when adhered to the user's skin. The numbers of plies and holes and the arrangement of holes and indicia can be arranged to adhere to a prescribed shot regimen that minimizes lipodystrpohy in the tissue underneath the sticker 280. Preferably, the plies underneath the indicated hole 304 have a corresponding void to allow an injection needle to access to the skin.

Figure 29:
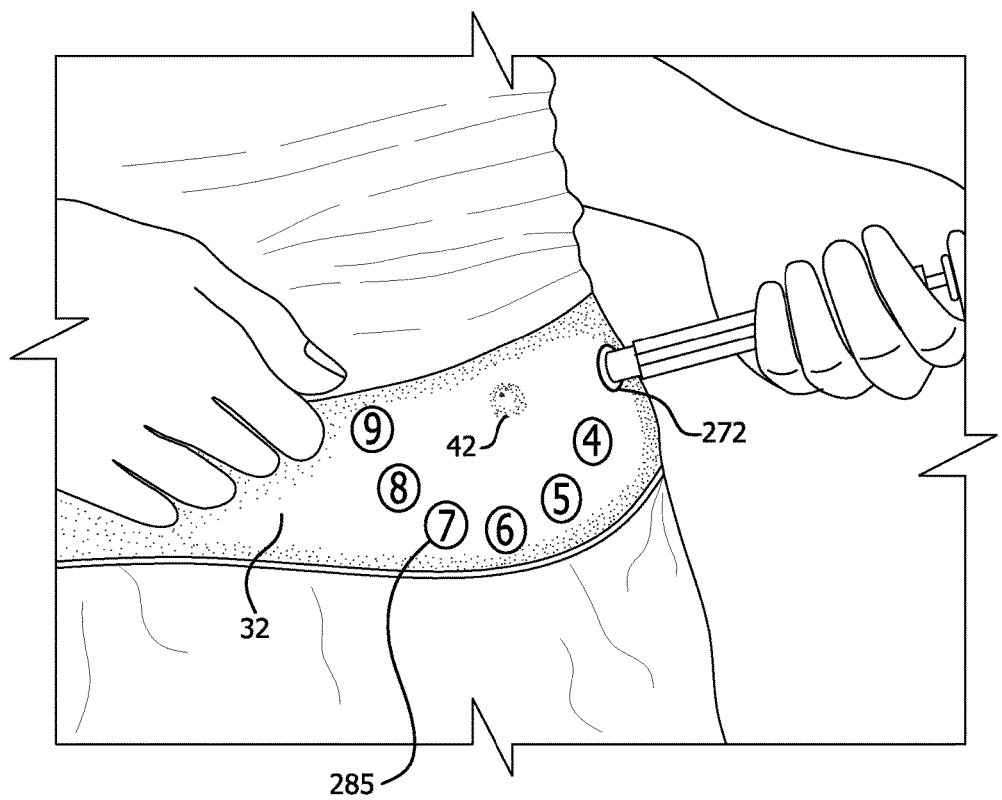
FIG. 29 depicts a user's abdomen as the designated body area divided into 12 injection sites representing a clock for which a chart can be divided into a number of injection sites where each space on the chart corresponds to the desired injection site in accordance with an illustrative embodiment of the present invention.
Figure 30A:
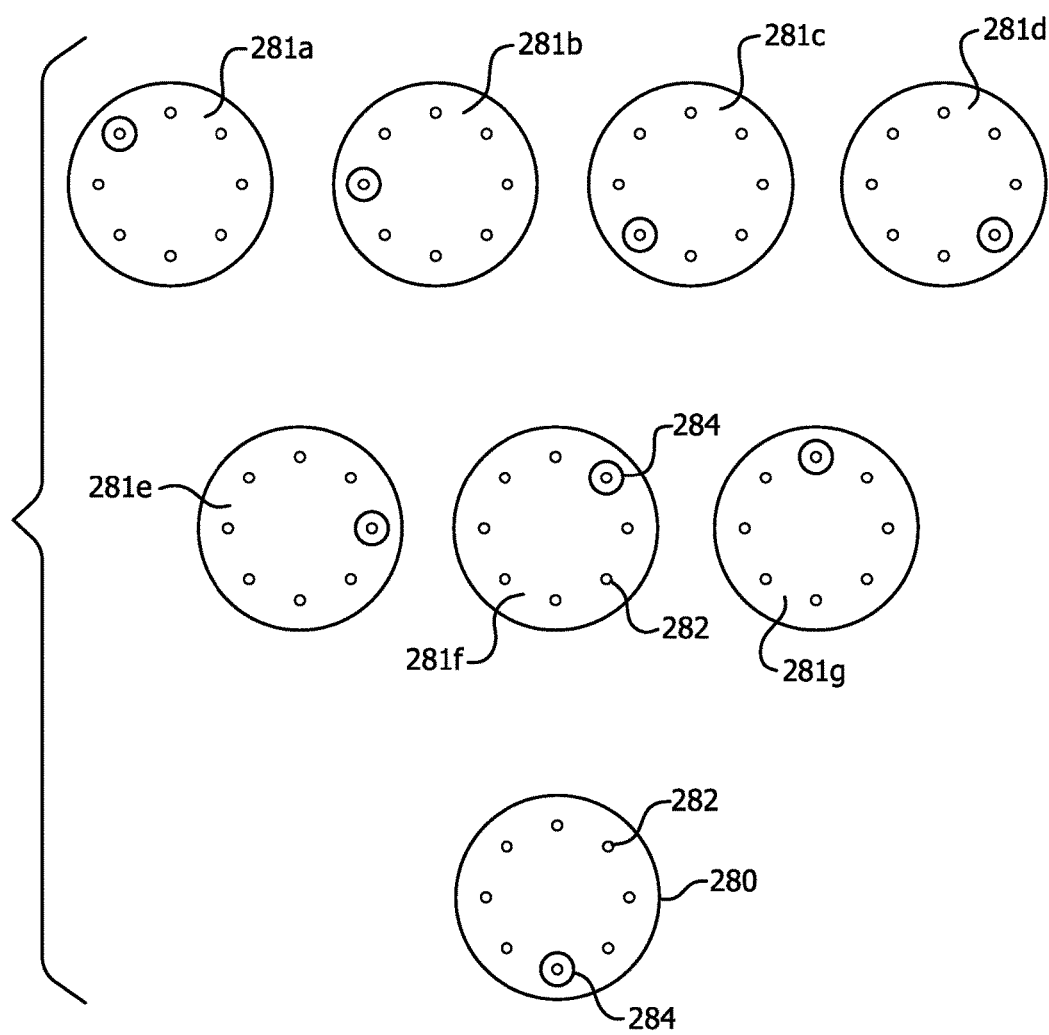
FIGS. 30A, 30B, 30C, 30D and 30E depict a sticker or other marker for application to a user's skin as guidance for where to locate a target injection site and identify previous injection site(s) on the user in accordance with illustrative embodiments of the present invention.
Figure 30B:
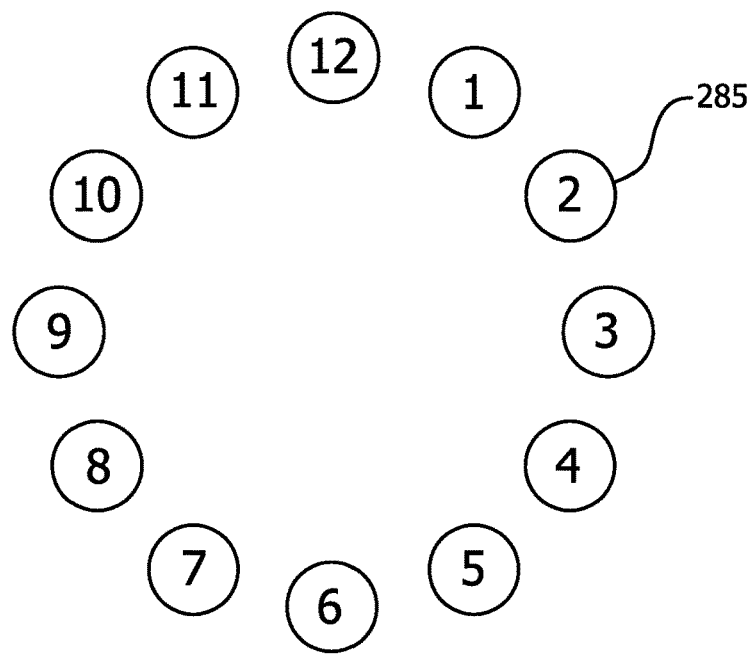
Figure 30C:
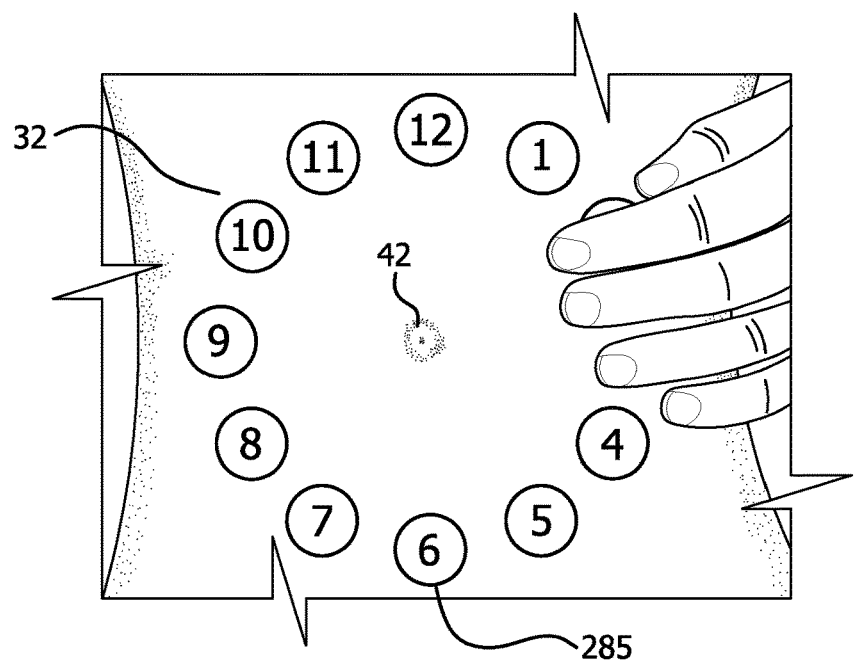

In accordance with another embodiment of the present invention, separate stickers can be provided for respective target injection sites as illustrated by each sticker 285 shown arranged in a designated pattern (e.g., a circle) in FIG. 30B. The respective stickers 285 can be arranged around the umbilicus 42 on a patient's abdomen 32, for example, as shown in FIGS. 29 and 30C. It is to be understood that the stickers can be arranged in other patterns (e.g., in a matrix or grid, or dispersed or spaced along a spiral 40 as shown in FIG. 23B or other type of path) on other body areas (e.g., the thighs, arms or buttocks). The spacing of the stickers can be selected so that the sites directly under the stickers are spaced 1 to 2 cm or other distance apart to prevent or reduce lipodystrophy.

A template can be provided with the stickers 285 to guide their placement on the patient's body area. A template can be a sheet of material with suggested pattern, or a sheet on which the stickers 285 are temporarily adhered (e.g., via double-sided adhesive) such that they can be rubbed onto or otherwise transferred to the patient body area in the pattern indicated on the template.

Figure 30D:
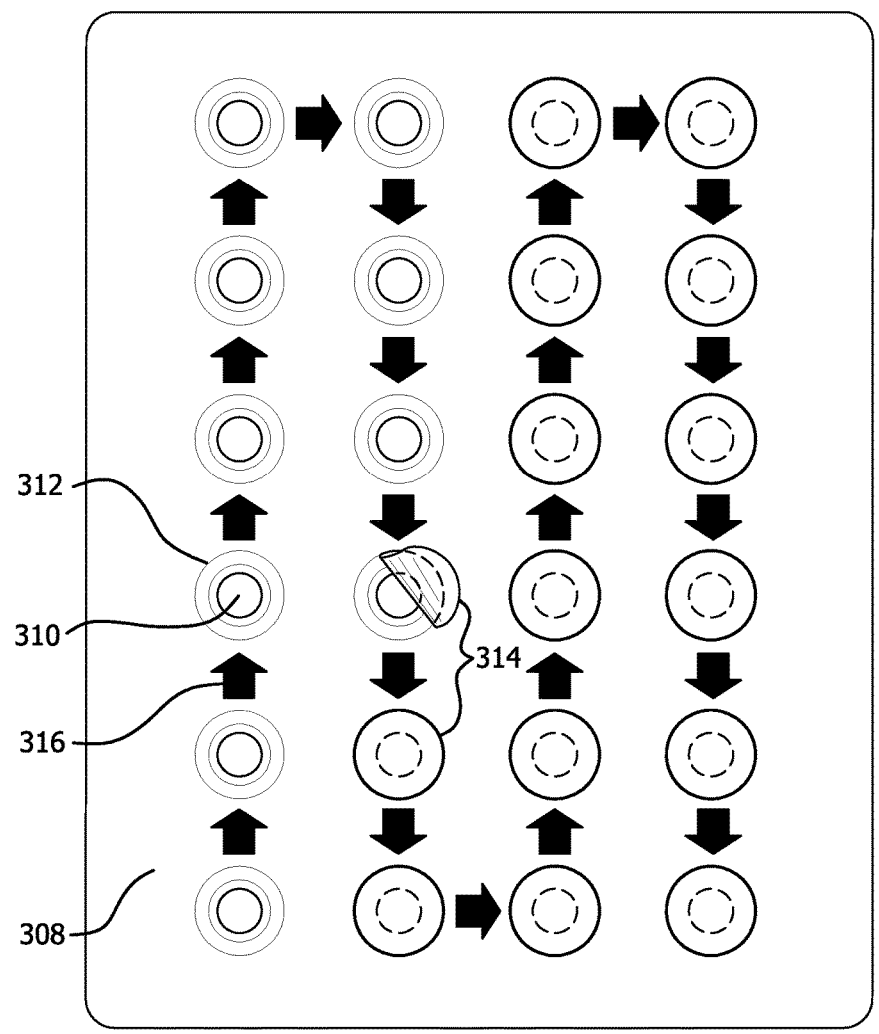
Figure 30E:
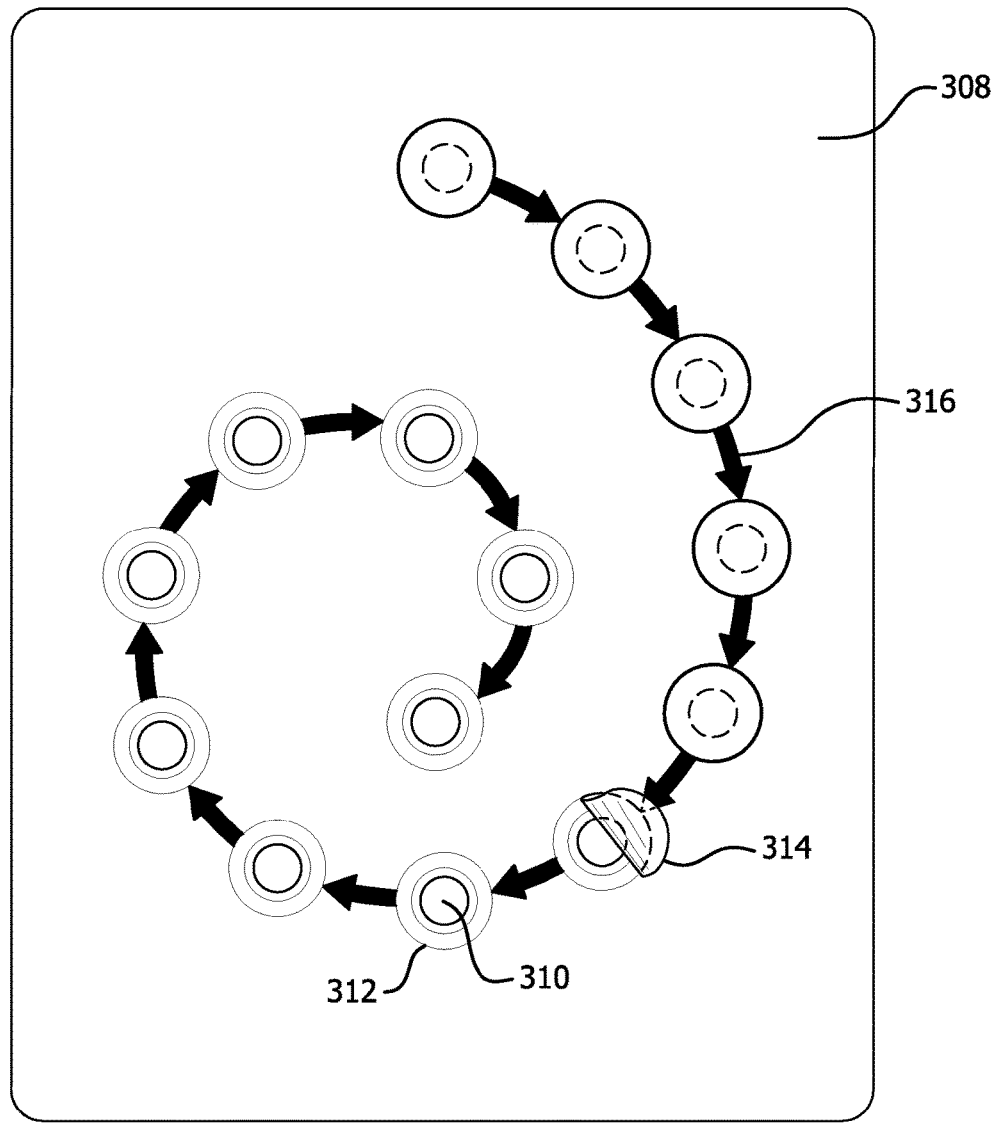

Alternatively, with reference to FIGS. 30D and 30E, a larger sticker 288 that comprises apertures 290 arranged in a pattern for injection site rotation can be used instead of a plurality of individual stickers 285, each sized for designating a single injection site. The apertures 290 can each be covered by an individual adhesive cover 294 that is removed prior to an injection at the body area site surrounded by an aperture 290 in the sticker 288. Thus, the covers 294, or lack thereof at a target site or aperture 290 serves as a visual reminder of where injections have already occurred. The apertures 290 can be dimensioned to have a diameter large enough to receive a needle. Alternatively, depending on the material of the sticker 288, no aperture 281 is provided, but rather indicia 292 are used to indicate a target site, and a user plunges a needle through the sticker material to inject into the body area beneath the indicia 292. This arrangement can also be used with a multi-ply sticker 280 wherein no holes are provided but rather indicia for guiding the penetration of one or more plies represents the target injection sites. If apertures 290 are provided in the sticker, the indicia 292 can still be provided around the aperture 290 as a visual guide for the user to that corresponding target site. In addition, pattern indicia 296 can be provided as a visual guide to the user to inject in the target sites using an order indicated by the pattern indicia. The pattern indicia 296 can be arrows between target sites 290, or numbers, lettering or other graphic provided on the sticker 288 next to or on the target sites 290 (e.g., if no aperture is provided), or on the covers 294 of apertures 290.

Regardless of whether stickers are multi-ply stickers 280 or individual stickers 285 per target site, or a sticker 288 comprising a pattern of target sites, the stickers can be made for example, from an adhesive strip with printed indicia that is applied to a patient's skin and remains until a user manually peels off the strip. Alternatively, the sticker 295 and 288 can be implemented using a material which is similar to a temporary tattoo, that is, the sticker is applied to a patient's skin and remains on his skin until removed with an alcohol swab. Since alcohol can be used to prepare a target site for injection, the alcohol swab can also wipe off the corresponding tattoo for that next injection.

Thus, the sticker 280, 285, 288 provides a simple mechanism by which a user can track past injection sites and an indication of where the next target injection site is located.

Optical Mouse Tools

Figure 31:
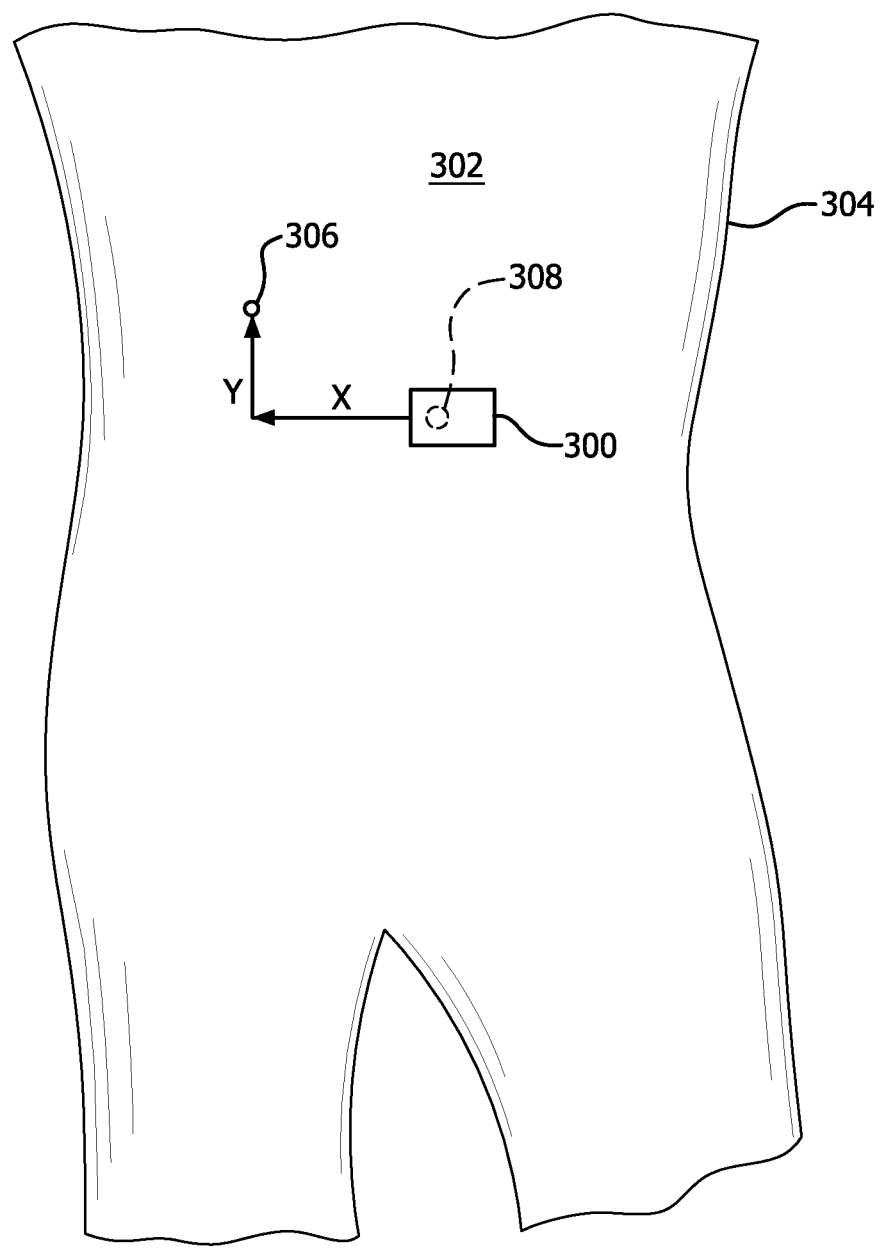
FIG. 31 depicts an injection site locating (ISL) device in accordance with an illustrative embodiment of the present invention.

In accordance with another illustrative embodiment of the present invention, an injection site locating device can be deployed that is similar in operation to a computer mouse interface. With reference to FIG. 31, the injection site locating (ISL) device 300 can be a portable, handheld device that is part of, or separate from, an injection device (e.g., a CSII catheter or pen needle), or other medical device (e.g., a continuous glucose monitor, or CSII pump), a mobile phone, or portable computing device (e.g., a personal data assistant (PDA), laptop, tablet, and so on), among other devices.

The ISL device 300 can be operated by a user (e.g., patient or caregiver) moving the ISL device over (e.g., on or proximal to the surface of) the target body area 302 of the patient 304. Using any of several different types of computer mouse technology to track motion of the ISL device 300, a processor integral to the ISL device, or at least communicatively coupled to the ISL device, can use the motion tracking to determine corresponding distances traveled by the ISL device over the body area 302 and define position coordinates 306 (e.g., Cartesian coordinates (x,y) or polar coordinates) of locations on the body area (e.g., coordinates for a target injection site or a past injection site(s)). For example, the ISL device 300 can track motion of the device 300 relative to a reference point 308 (e.g., the umbilicus 42) in a selected body area 302 (e.g., the abdomen) to facilitate defining, storing and tracking coordinates of past injection sites, planned or target injection sites, or sites to be avoided such as lipodystrophic sites. It is to be understood that that ISL device 300 can be used with respect to other body areas 302 (e.g., thigh, arm, buttock, and so on) and that other reference points 308 can be used (e.g., reference points corresponding to a naturally occurring feature on the body, artificially occurring feature such as a tattoo or user's mark) that may vary depending on target body area 302.

For example, an ISL device can be provided with optical computer mouse components such as a light-emitting diode (LED) and corresponding image sensor (e.g., a photodiode), that is, an optoelectronic sensor that operates as a low-resolution video camera to detect movement relative to a surface. The LED can be an infrared laser diode or a regular LED. The optical computer mouse components can be, for example, components developed and commercially available from Agilent Technologies or Logitech International S.A.). As with an optical mouse, the injection site location device 300 employs a tiny camera to take pictures (e.g., on the order of at least 1,500 pictures every second) as it traverses a surface such as a body area 302 being considered for a target injection site (i.e., that supports plural injection sites having medically acceptable spacing). The device 300 has a small, light-emitting diode (LED) for bouncing light off that body area surface 302 onto a complementary metal-oxide semiconductor (CMOS) sensor. The CMOS sensor, in turn, sends each image to a digital signal processor (DSP) or other processor in the device (or in another connected device) for analysis. The DSP detects patterns in the images and determines how those patterns have moved since the previous image. Based on the changes in patterns over a sequence of images, the DSP determines how far the ISL device 300 has moved and sends the corresponding coordinates to the computer or other control device (e.g., programmed controller or ASIC) in the ISL device 300. The sensing and image storing and processing can be performed via the same processor or different processors. Further, the motion tracking achieved via the image processing and the application of the motion tracking device to injection site tracking and monitoring can be achieved via the same processor or different processors.

The ISL device uses the coordinates received from the image sensor/processor to track, monitor and manage injection site rotation by providing one or more functions, with associated feedback to the user including but not limited to:

site selection site avoidance site tracking and reporting (e.g., storing coordinates and dates and times of each injection)

generation of reminders and incentives.

For example, the ISL device 300 can be programmed to store information for at least one injection site rotation regimen including information regarding each body area 302 to be used for target injection sites 306, the frequency with which the body area 302 is used with respect to other body areas (e.g., a time period or total number of injections before rotation to another body area is recommended), the time, date and coordinates of past injection sites, the coordinates of injection site locations 306 and/or body areas 302 to be avoided and a corresponding time period or other criteria that needs to be met before the site 306 or area 302 can be used again for target injection sites, among other information.

The ISL device 300 can be configured in accordance with software or using an ASIC or FPGA to perform a number of operations such as site selection. The ISL device can have an integral user interface or be connected or wirelessly coupled to a device having a user interface. The user interface can be configured with a user input (e.g., button or switch) to allow a user to select an initial body area 302 to receive an injection and corresponding reference point 308. For example, a button on the ISL device 300 can be depressed by the user when the ISL device is centered over the umbilicus or other feature used as a reference point 308. The ISL device or connected device can have an output such as a display, or indicator (e.g., LED(s) illuminated and optionally flashed), or audible sound generator to generate an indication of when the currently detected coordinate is acknowledged as the reference point 308. Multiple presses of the button or other user input mechanism can allow for the user to scroll through a list of target body areas 302 on a display (e.g., a display that is integral to the ISL device 300 or on a connected external device) and to select one (e.g., depress the button a selected number of times or for a selected duration such as for 2-3 seconds).

Once the body area 302 and corresponding reference point 308 are set, the user can move the ISL device 300 over the body area toward a target injection site 306. Using motion tracking and stored data on past injection sites and sites to be avoided and regimen regarding when to select a new body area 302, the target injection site can be evaluated by the ISL device 300 and an indication generated (e.g., audible and/or visual) when the target injection site is determined to be a valid site. The ISL device 300 then stores the coordinates for that injection site, as well as time and date. Evaluation and determination of valid injection sites can depend on a number of programmed and/or configurable parameters and criteria such as, but not limited to, permissible proximity to adjacent past injection site (e.g., which can depend on body area 302, amount of time that has elapsed since the injection occurred at the adjacent injection site, degree of lipodystrophy presented in the area, among other factors).

The ISL device 300 can also be configured to automatically determine (e.g., based on the above-referenced factors and stored data such as past body area rotations and injection sites and stored regimen data) and output a suggested target site 306 to the user. The indication can occur at the outset of the use of the ISL, or can occur in real-time as the ISL is being moved about the body. For example, the ISL device 300 can generate audible or visual indications of the suggested target injection site, or generate varying audible and/or visual indications as the ISL device 300 approaches the suggested target site 306 when moved by the user.

As stated above, a number of different regimens can be implemented with varying numbers of injections per day, or injections or infusions per week, or a selected number of days, or target body areas, and so on.

Although the above illustrative embodiments of an ISL device 300 have been described using optical mouse technology, it is understood that a mechanical mouse implementation (e.g., employing rotation of orthogonal shafts which drive chopper wheels for distance measurement) could be used. Such an implementation, however, could be somewhat difficult or less accurate given any unevenness of the surface of the body area 302 over which it is used, which can vary significantly from body area to body area and from patient to patient. Alternatively, the use of an internal accelerometer to track the movements of the ISL about the body area 302 can accomplish the same result.

Figure 32:
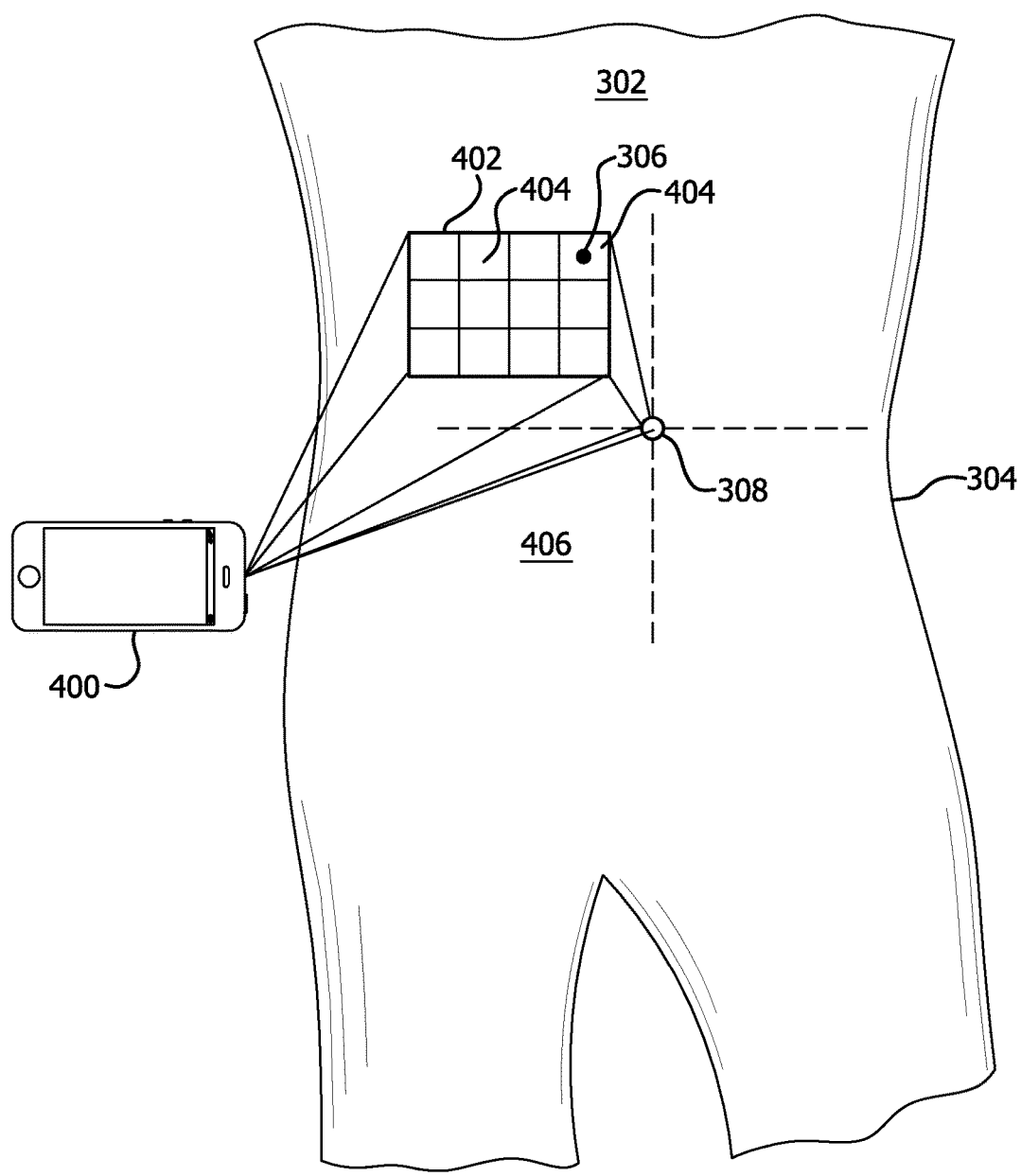
FIG. 32 depicts an injection site projection (ISP) device in accordance with an illustrative embodiment of the present invention.

Optical Projection Tools:

In accordance with another illustrative embodiment of the present invention, an injection site projection device 400 can be deployed that is similar in operation to a computer mouse interface. With reference to FIG. 32, the injection site projection (ISP) device 400 can be a portable, handheld device that is part of, or separate from, an injection device (e.g., a CSII pump/catheter or pen needle), or other medical device (e.g., a continuous glucose monitor), a mobile phone, or portable computing device (e.g., a personal data assistant (PDA), laptop, tablet, and so on), among other devices. For example, the injection site projection device 400 can be located in the reusable portion of a patch pump for CSII. The patch pump can, in turn, be used to project an image of a grid or other target image onto a body (e.g., a patient's abdomen)

to help a user (e.g., the patient or a caregiver) locate a target injection site in the body area for attaching a catheter for medicament infusions via the pump. The location of such a projection function in the patch pump would be particularly convenient to such a user and can help guide the user to better distribute injection sites within an area.

The ISP device 400 can be operated by a user (e.g., patient or caregiver) holding the ISP device 400 over a target body area 302 of the patient 304. By configuring the ISP device 400 with any of several different types of handheld image projection technology, the ISP device 400 can project a grid 402 onto the body area 302. The grid 402 comprises a plurality of sections or sectors that represent different or respective target injection sites. For example, the ISP device 400 can be provided with a handheld projector (e.g., a pico projector or mobile projector) to project a stored digital image of a grid 402 onto the surface of a selected body area 302. The grid 402 has respective sectors 404 that represent an injection distribution pattern for that body area 402. It is to be understood that different grid patterns can be stored for use on respective body areas 302. For example, a grid 402 for use with respect to the abdomen may have a different overall size and/or shape than a grid 402 that is intended to be projected onto a thigh or the buttocks. Further, the size and number of sections 404 in a grid 402 can vary depending on which body area 302 or zone 406 of that area 302 the grid is to be projected. For example, as shown in FIG. 32, the body area 302 corresponding to the abdomen is divided into four zones 406 in accordance with an example injection administration regimen. The same body areas can be divided into different numbers of zones and locations of zones, depending on a patient's preferred or prescribed medicament administration regimen and injection site rotation plan.

The ISP device 400 can be configured with a user interface that allows a user to input or otherwise select a body area and optionally a zone of that selected body area (e.g., outside of right thigh, or outer section of left buttocks, or right, upper quadrant of zone of abdomen). The ISP device 400 can be configured to project an image of the same grid regardless of the target body area 302, or select a grid image that corresponds to the target body area 302, or select from a plurality of grid images that are stored at the device 400 to accommodate different patients' medicament administration regimens and injection site rotation plans.

In a manner similar to the ISL device 300 described above, the ISP device 400 is configured to allow the user to select a reference point 308 from which to project the image of the grid 402, or at least specify the target body area 302 for which a default or automatically selected reference point 308 is used as a point of origin from which the device 400 can project the image of the grid onto the target body area. The user can employ a mobile app, or printed media (e.g., a calendar or printed indicia on injection or infusion device packaging), or a temporary skin marker, or other apparatuses and methods described herein to maintain a record of which sectors 404 of a grid 402 in a selected body area 302 and zone 406 have been used as injection sites.

Mobile Phone Applications and Tools

Figure 34:
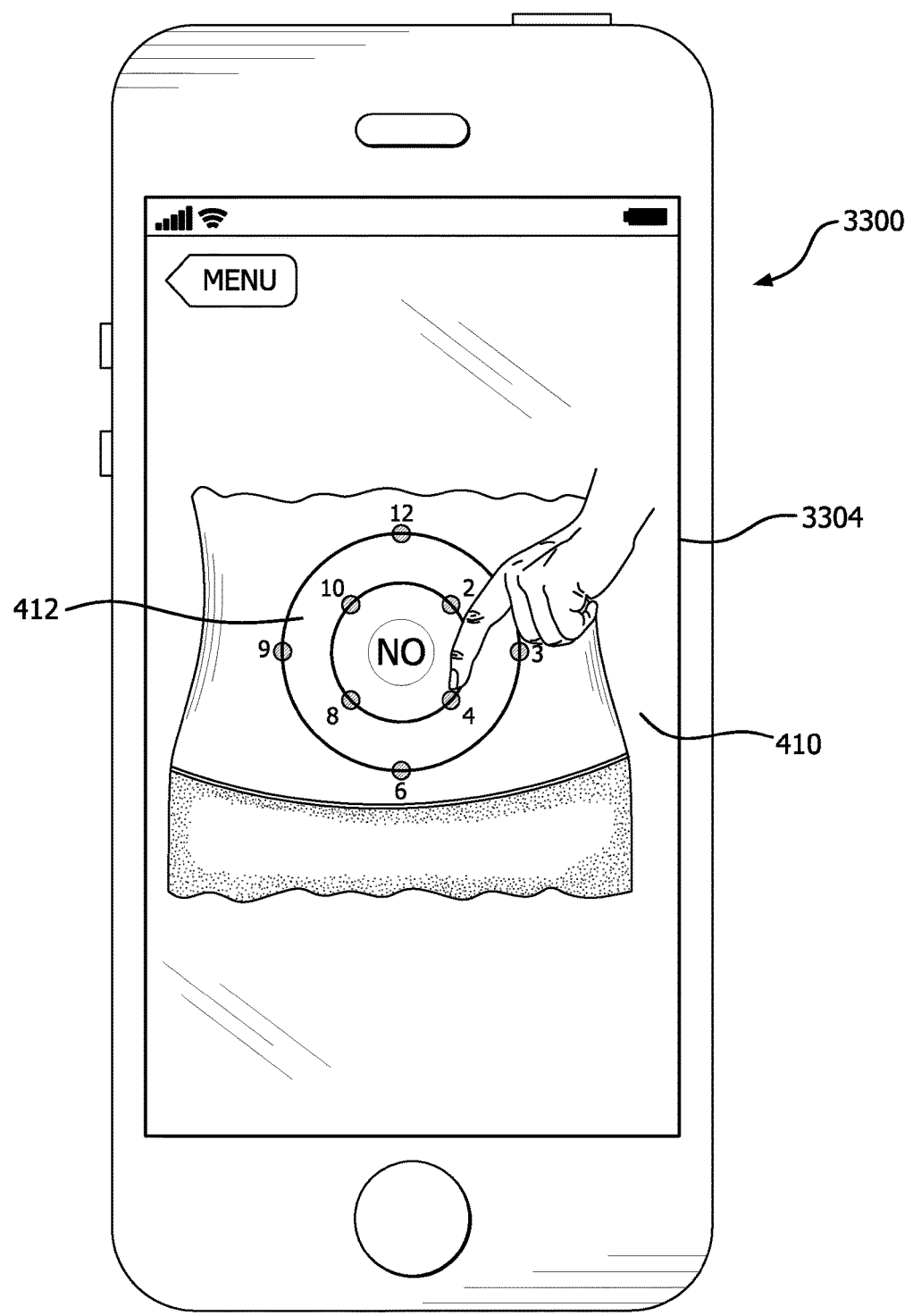
FIGS. 34, 35, 37 and 38 are diagrams of respective screen displays on a mobile phone with mobile app in accordance with an illustrative embodiment of the present invention.

In another embodiment, a mobile device such is a cellular phone or mobile phone may be used to further enhance body area and injection site diversity, that is, rotate injections among body areas, as well as distribute injection sites within an area. FIG. 34 depicts an illustrative mobile phone running software according to an embodiment of the invention. As will be appreciated, the mobile phone includes an image sensor such as a camera, and preferably a front facing camera. The mobile phone further includes software and data storage adapted to perform functions to assist a user in tracking injections and diversifying body area and injection locations within body areas. The mobile phone software utilizes the front facing camera and displays the camera view on the display of the mobile phone, such that the user may point the front-facing camera at her body and view an image of the front-facing camera view of her body with information preferably overlaid onto the provided view.

Figure 33:
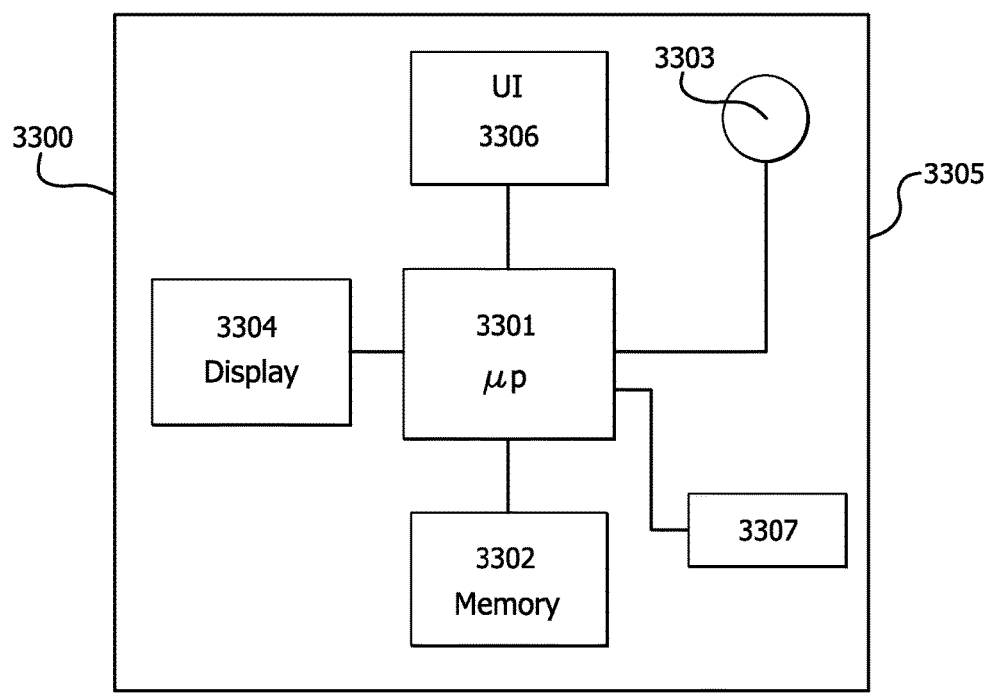
FIG. 33 is a block diagram of a mobile phone with mobile app in accordance with illustrative embodiments of the present invention.

As shown in FIG. 33, a mobile device 3300 according to an embodiment of the present invention preferably includes a processor 3301, a memory 3302, an image sensor 3303, a display 3304 preferably oriented on the same surface of the device as the image sensor 3303, a housing 3305, and a user interface 3306. Memory 3302 preferably stores software to perform required functions for assisting the user with body area and injection site diversity as discussed above. The memory further stores the user shot regimen, an injection site rotation plan, user injection data, injection site status data, and any other data necessary to perform functions as discussed above.

The image sensor 3303 is preferably a camera such as those provided on most mobile devices. The image sensor provides image data to the processor 3301 and/or the memory 3302 in order to perform the functions described above, and to be described in further detail below. The image sensor 3303 may further be a specialized image sensor to provide additional functionality. For example, the image sensor 3303 may record images in the infrared wavelengths to provide additional diagnostic information to the memory 3302 and/or the processor 3301 (e.g., for detection of skin conditions such as lipodystrophy presenting as swelling or hardness but not necessary skin color changes that may be detected by a conventional camera). By providing additional functionality to the image sensor 3303, more sophisticated and/or accurate diagnoses may be made by the mobile device, and less user interaction and/or judgment may be needed, according to the software functions performed by the mobile device.

The display 3304 preferably displays at least the view of the image sensor 3303, along with additional information as discussed above and to be discussed in further detail below. For example, the display 3304 preferably displays the injection sites overlaid onto the image of the body area viewed by the image sensor 3303, as well as feedback information such as the guide arrow discussed above. The display 3304 also preferably displays injection site status information for the injection sites within view of the image sensor 3303. For example, injection sites that are lipodystrophic (hereinafter referred to as "lipos") may be indicated as such to remind the user to avoid injections in those injection sites.

All of the components are preferably housed in a convenient housing 3305, as is common in mobile devices. The mobile device further preferably contains at least a touch screen user interface 3306 coupled to the display 3304 to provide a convenient user interface. The user interface 3306 may of course include other elements known or foreseeable in mobile devices such as buttons, proximity sensors, gyroscopes, compasses, GPS sensors, photosensors, and the like. The mobile device 3300 may further optionally include a pico-projector 3307, or the like, to work in conjunction with, or separate from the display 3304. The pico-projector 3307, as discussed above, preferably projects information directly onto the user's body to assist the user to achieve body area and injection site diversity. Alternatively a virtual grid is placed on the live image (or photograph) of the patient's body shown in the display 3304.

The image sensor of embodiments of the present invention may advantageously be used for additional functions, such as scanning a medication box. Scanning a medication box may include, for example, scanning a QR code imprinted on the box. The app may require scanning of a particular manufacturer's box to continue functioning or receiving updates to the app, or scanning may trigger an advertisement or advice to be displayed on the mobile device. In an advantageous business scheme, and to encourage loyalty to a particular manufacturer, discounts may be provided to users for continued use of the app, or for every predetermined number of injections administered. The app can preferably provide additional feedback to the user, such as reminding him to change his needles, or providing feedback on his compliance with his healthcare provider's recommended therapy regimen.

The app can also be programmed to alert the user when the next injection should be administered based on the stored information mentioned above (e.g., injection regimen, injection data). The app can also be programmed to determine where the next injection site should be based on the stored site rotation plan and past injection data (e.g., location and time), and can include warnings to avoid identified and stored sites exhibiting lipodystrophy (at least for a programmed duration of time or until site is cleared by a physician) or at least refrain from suggesting identified lipo sites (e.g., and optionally a selected number of adjacent sites) for a next injection.

FIG. 34 further illustrates views that may be provided by a mobile phone 3300 according to an illustrative embodiment of the invention. FIG. 34 shows a screen view 410 on a display 3304 generated when a user selects her abdomen as a body area. Injection locations on the abdomen indicated generally at 412 are overlaid onto the smartphone display view 410 of the abdomen. The preferred current injection site (e.g., position "4") is highlighted so that the user may locate the site using feedback from the mobile phone display view. In one embodiment, the user points her finger to a location on the body area, the abdomen in FIG. 34, and the software determines the location of the finger relative to the abdomen (e.g., using image information from the image sensor 3303 such as a camera), the location of the preferred current injection site on the abdomen (e.g., a designated location in accordance with an injection regimen, or selected using criteria described above in connection with the ISL device in FIG. 31 to track, monitor and manage injection site rotation) and provides an on-screen guide arrow pointing from the position of the finger on the display to the position of the preferred current injection site (e.g., position "4" as shown in FIG. 34). As the user moves his finger, the guide arrow is updated until the finger is within a predetermined range of the preferred current injection site. Having determined the location of the current preferred injection site using feedback from the mobile phone, the user can inject in that site, and record the injection in the mobile phone. The mobile phone records the injection and calculates the next preferred body area and injection site according to an injection regimen and site rotation plan programmed into the mobile phone, and preferably coordinated with the user's healthcare provider.

As will be appreciated, the software may be provided to a user's mobile phone by way of an app download as is customary in the art. The app preferably tracks injection sites as they are administered, and in particular stores the location of the last injection so that the user can be alerted if they attempt to inject in the same spot twice in a row. The app preferably is programmed with an injection regimen, and advises the user where the next injection should be administered. The app preferably permits a user to exclude certain body areas or injection sites within a body area. The app may store a history of injection sites and the time and date of injections, which history may also be shared with a healthcare provider.

Figure 35:
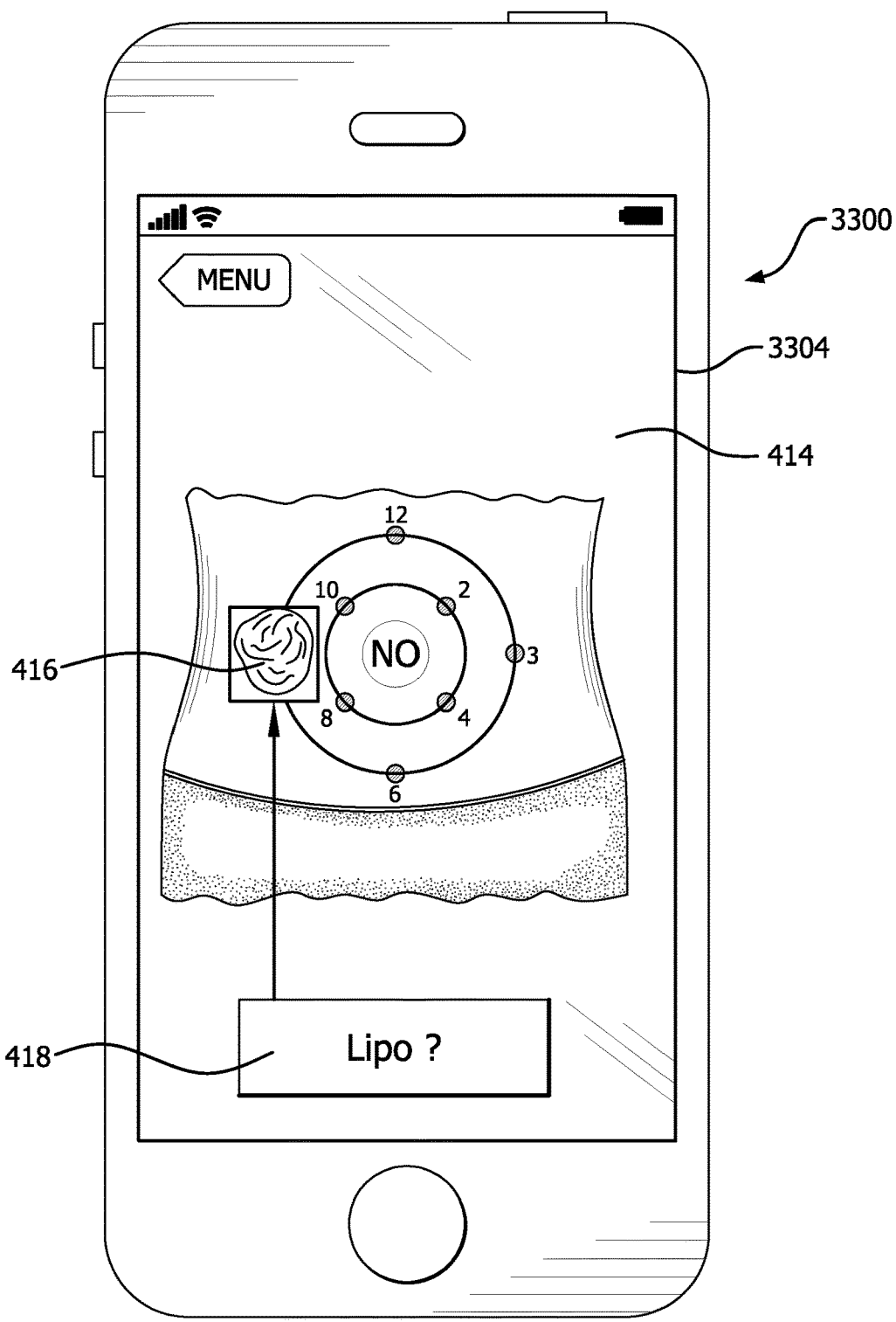

As will be appreciated the mobile phone and camera combination may perform additional functions. As shown in FIG. 35, the camera 3303 analyzes coloration patterns of the user's body area, and determines if any injection sites appear to be lipos. The mobile phone 3300 preferably identifies any such lipos 414 on a screen view 416 and alerts 418 the user to perform further evaluation of the potential lipo by, for example, palpating the area. If a lipo is determined to exist for one or more injection sites by any combination of color change or manual entry of a site following palpation, the user can confirm the existence of the lipos (e.g., by an input on the touchscreen display 3304 or on another user interface 3306 associated with the mobile phone), and the mobile phone advantageously records the lipo site locations (e.g., in memory 3302) to update the ongoing injection regimen and/or site rotation plan to avoid the lipo locations until sufficient time has been provided for the lipos to heal. Lipo sites may be eliminated from the regimen by any combination of determination by the patient or a healthcare provider such as the user's doctor.

In another embodiment, the mobile phone according to an embodiment of the present invention is provided with a pico-projector 3307, or the like. The pico-projector 3307 may be used in place of the mobile phone display to project information onto the user's body. The information preferably includes site locations for the particular body area within view of the mobile phone camera. The information may further include status information for the injection locations, and information identifying the current preferred injection site location. In this manner, with information projected directly onto the user's body, the user may more easily determine the correct current injection site location.

Figure 38:
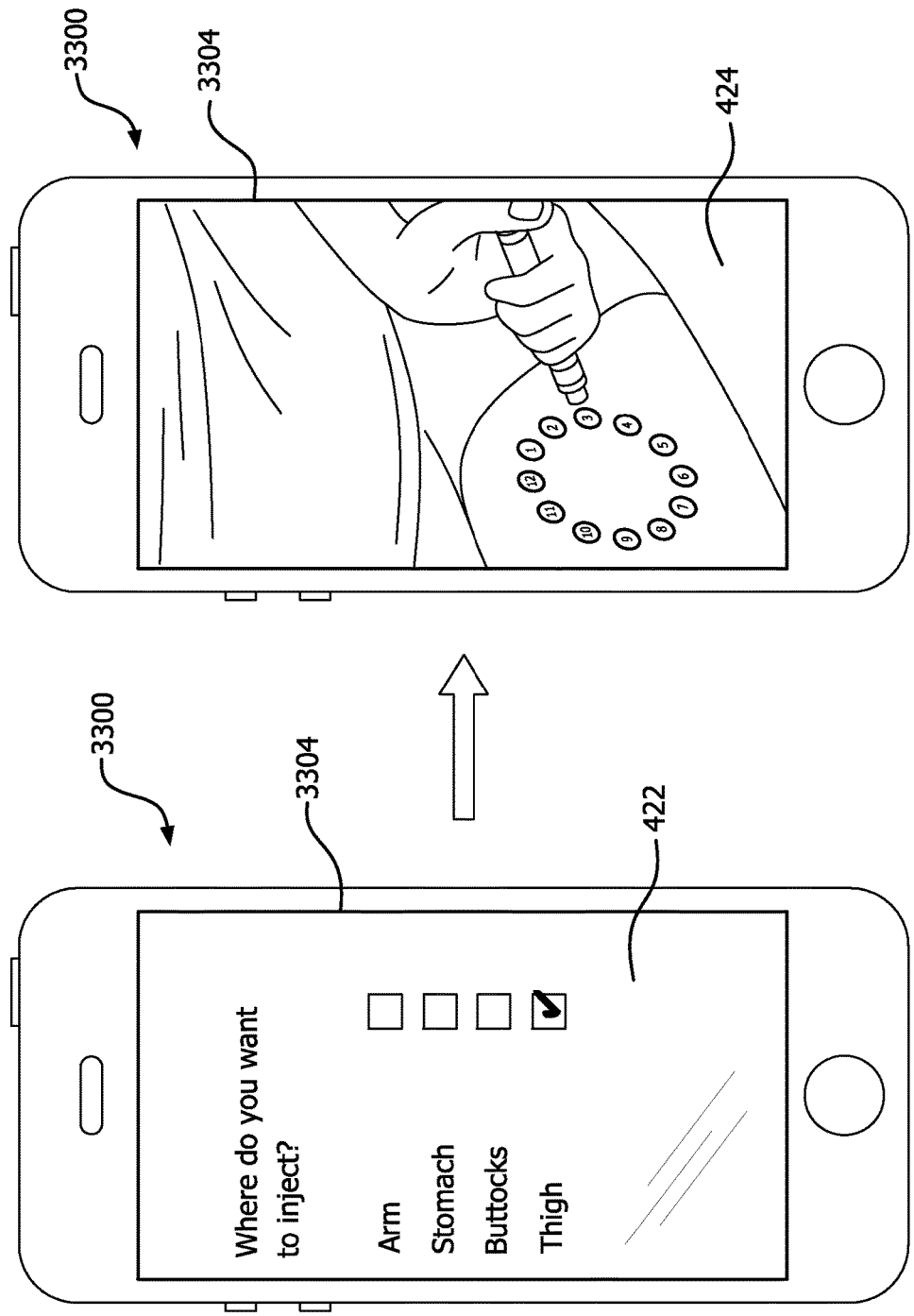

In yet another embodiment, the mobile phone need not necessarily utilize the camera 3303, but rather may simply record injection locations according to user input. In this embodiment, the mobile phone preferably is programmed to track the user's shot regimen as provided by his healthcare provider, and alerts the user to injection times, and preferred current injection body area and injection site in accordance with a stored site rotation plan. As discussed above, the mobile phone may further track injection sites to be avoided such as due to lipos, or the like, and preferably alters the injection regimen according to any such conditions. With reference to FIG. 38, the phone app can generate a screen 422 requesting user input on the selected body area where the user wishes to inject. The phone app can be configured to display a screen view 424 providing a designated distribution pattern for the inputted body area (e.g., a spiral pattern for the buttocks area, or a grid or circular pattern for the thigh or abdomen, or a grid for the arm or for a abdomen section or quadrant, and so on) and, based on stored data relating to history of injections for that body area and in which sites, the phone can indicate a selected one of the target sites. Depending on the sophistication of the features provided by the phone app, the phone can simply indicate a pattern, or indicate a pattern and a suggest target site in that pattern, or use the optical technology described above to project a grid or use an optical mouse feature to assist the user in locating the target site on the body.

In a further embodiment of the present invention, the mobile phone 3300 may be programmed to work in connection with particular medication packaging as discussed above in connection with FIGS. 25-28. That is, medication packaging may contain codes, such as QR codes, or the like, which may be scanned by the image sensor 3303 of the mobile device to identify the medication packaging and/or injection regimen directed by the medication packaging as shown in FIG. 37. In this embodiment, the mobile device software preferably coordinates with the printed indicia on the medication packaging. For example, in the case of four indicia icons to indicate which body area for injection, the mobile device may present the same indicia icons (e.g. icons 230) as user interface elements for ease of recording injections as indicated by the example screen view 420. That is, for example, if the packaging indicia with an "X" indicated the abdomen as a body area for the next injection, then the mobile device would present the four indicia types ("X", "O", "Square", "triangle") as user interface elements, and the user simply presses the "X" on the touchscreen 3304 to indicate that the "X" medication was injected in the abdomen. The mobile device software records an injection in the abdomen at the given time. In other words, the user presses a colored and/or shaped button on the mobile phone display that corresponds to compartment of packaging from which the user removed an insulin product for administration as illustrated in FIGS. 25-28. The mobile app is programmed to provide daily and historical (e.g., over multiple days) tracking of injection site locations and such information can be displayed in a simple, easy to understand manner, using the packaging printed indicia.

Figure 36A:
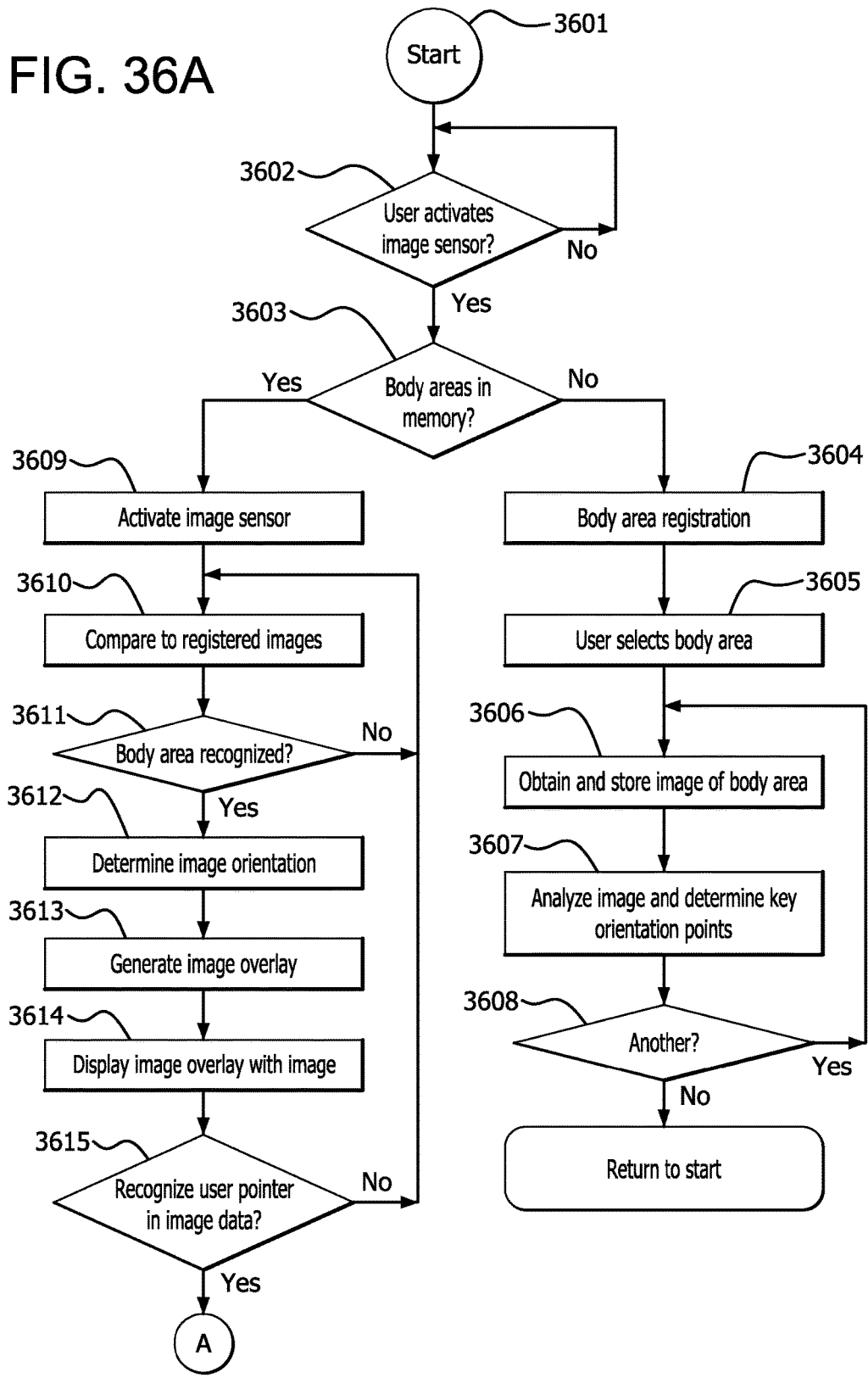
FIGS. 36A and 36B are a flow chart of operations of a mobile phone with mobile app in accordance with an illustrative embodiment of the present invention.
Figure 36B:
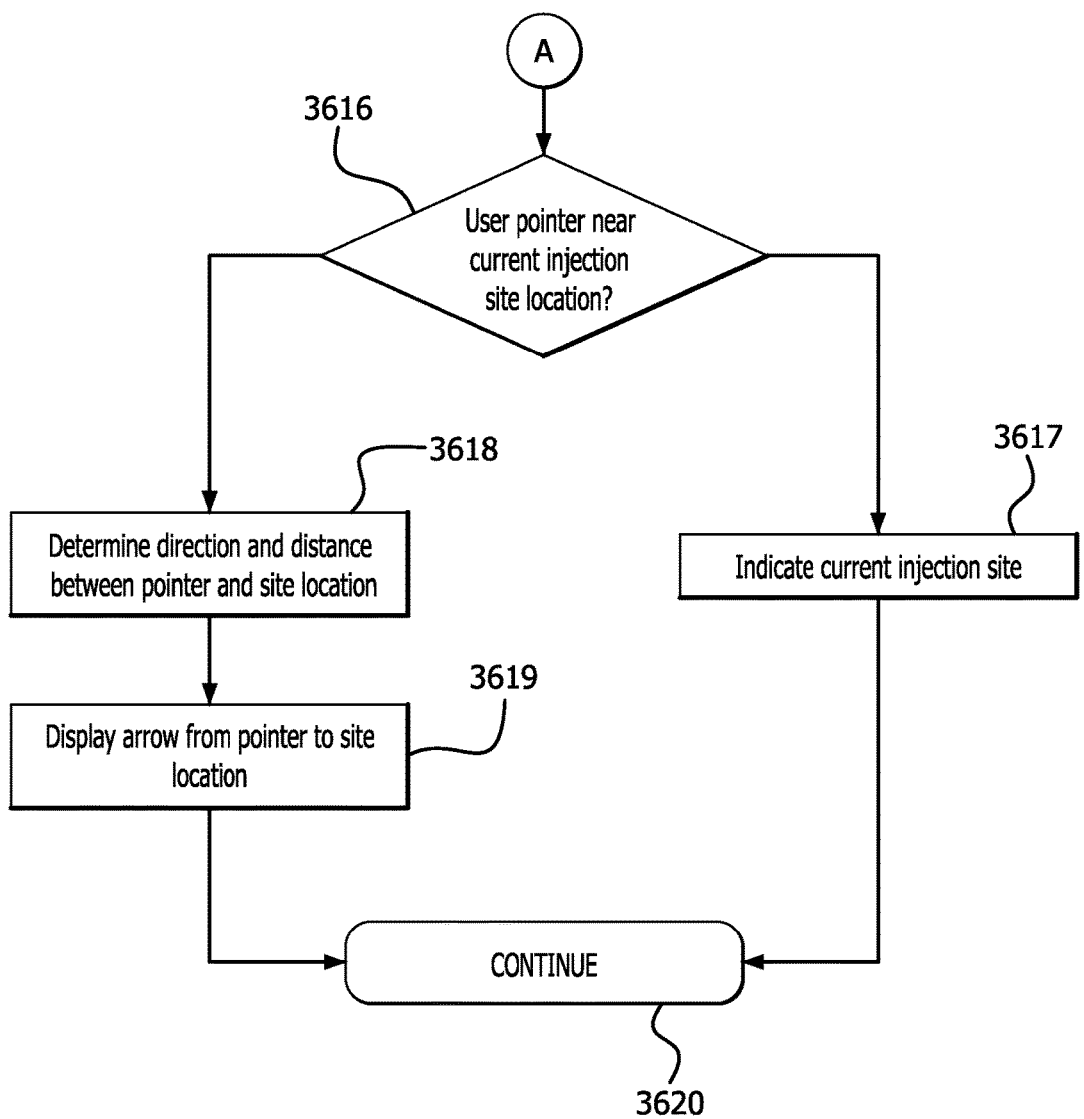

An illustrative method of using a mobile phone 3300 to assist a user in determining a current injection site location according to an illustrative embodiment of the invention will now be described in connection with FIG. 36. At step 3602, the device determines if the user has activated the image sensor. If the user has not yet activated the image sensor, then the method continues until the user does activate the image sensor. If the user has activated the image sensor, then the method continues at step 3603. At step 3603, the method determines if the user's body areas are already recorded in memory. If the body areas are not recorded in memory, then the method continues at step 3604. In step 3604, body area registration is begun. At step 3605, the user selects the body area that they want to register. At step 3606, the device obtains and stores an image of the body area for later comparison. At step 3607, the image of body area received by the body sensor is stored in memory 3302 and analyzed by the processor. The processor 3301 preferably determines key orientation points for future reference against subsequent images obtained by the image sensor 3303 of same body area. At step 3608, the method determines if another body area needs to be registered. If another body area needs to registered, the method returns to step 3604. If no further body areas need to be registered then the method returns to the start 3601.

On the other hand, if at step 3603 the body areas are already stored in memory, then the method continues at step 3609. At step 3609, the image sensor 3303 is activated and the user preferably aims the image sensor at the body area they wish to inject into. Alternatively, the device can analyze the user's injection shot regimen and determines which body area should be utilized and advises the user to point the image sensor at that body area. Once the image sensor 3303 obtains an image of the desired body area, the image is compared with the registered body images at step 3610. At step 3611, the processor 3301 compares newly obtained body area images to the body areas images previously registered and determines if the body area currently being viewed is recognized. If the body area is not recognized then the method returns to step 3610. If the body area is recognized then the method continues at step 3612.

At step 3612, the processor 3301 determines the body area image orientation. At step 3613, an image overlay is generated. The image overlay preferably shows injection sites and in particular highlights the current injection site. At step 3614, the device displays the image overlay with the image sensor view so that the user can see the injection sites together with the body area and, in particular, the user can see which of the injection sites is the current injection site. The user can then point her finger or any other suitable device or object at her own body area in order to pin point the current injection site. The device, according to an illustrative embodiment of the invention, continues to analyze views of the body area obtained by the image sensor and to process those images.

At step 3615, the processor 3301 determines if a user pointer is recognized in the image sensor data. If a user pointer is not recognized then the method returns to step 3610. If a user pointer is recognized, then the processor determines if the user pointer is near the current injection site at step 3616. If the processor determines that user is pointing at the current injection site then the method continues at step 3617. At step 3617, the image overlay is updated to highlight that the user pointer is pointing to the current injection site to indicate to the user that they have located the current injection site and may administer the current injection at that injection site. If the processor 3301 recognizes the user pointer in the image data but determines that the user is not pointing to the current injection site location, then processor determines the direction and distance between the user pointer and the current site location at step 3618. At step 3619, the image overlay is updated to include an arrow which points from the user pointer to the current site location in order to provide feedback to the user of which way she should move her user pointer object (i.e., her finger) in order to locate the current injection site. The method continues in this manner at step 3620 until the user provides herself with an injection, at which point they may record the injection in the device. Feedback can also be generated as audible tones that change frequency, volume, tone or provide pre-recorded verbal feedback as the user approaches and becomes more distant from the target injection site.

Lipohypertrophy Education Tools

Figure 39A:
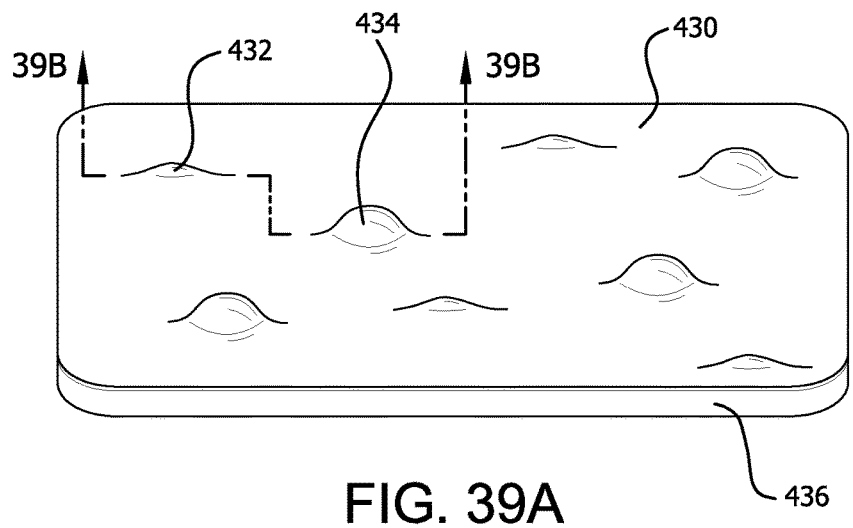
Figure 39B:
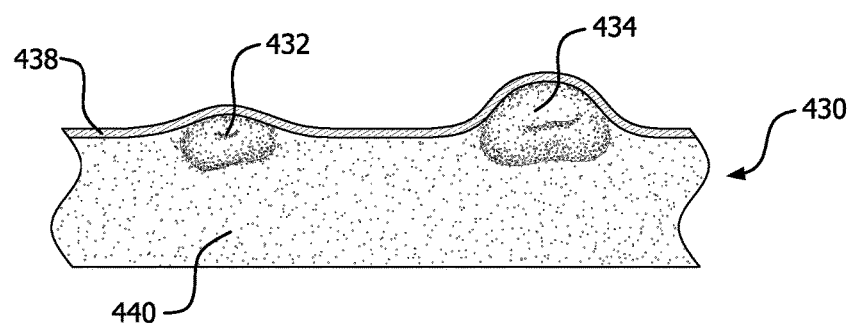

With reference to FIGS. 39A and 39B, a tactile education tool 430 is provided that comprises a substrate or base and is formed at least on one side thereof with a material or combination of materials (e.g., a type of foam, rubber, plastic or other suitable synthetic material) having different sizes of mounds 432, 434 that are dimensioned and textured to simulate lipos occurring in a patient's tissue. FIG. 39B is a cross-section of a section of FIG. 39A showing at least two different sizes of mounds or simulated lipos 432 and 434 disposed in a tissue layer (e.g., subcutaneous fat) 440 under a skin layer. It is to be understood that different synthetic materials can be used to simulate the tactile characteristics of the skin layer 438 and the tissue layer (e.g., subcutaneous fat) 440, and that the simulated lipos can be created using multiple layers or a unitary layer of material having areas of different texture or density. Thus, a user can palpate the tool 430 to develop a reference sensation for what a lipo typically feels like such that the user is better able to palpate his own injection areas or those of a patient to discern if a lipo is developing in that body area from insufficient injection site rotation.

The tool 430 can be provided on a substrate 436 sized to be included in a package as illustrated in FIGS. 25-28 or other packaging used for different injector supplies besides disposable supplies such as a pen injector package. The tool 430 can be sized to have a credit card shape for ease of portability and use by a patient or care giver, or provided with a magnetic on the back of the substrate for hanging on a metallic surface. Alternatively, the tool 430 can be dimensioned to be as large as and therefore to simulate a body area on a typical patient. For example, the tool 430 can be configured as a three-dimensional model of a body area subject to injection, or as a mannequin (e.g., full body, torso or other partial dummy or lay figure form) having the tool 430 integrated into or otherwise affixed to conform to a target body area on the mannequin for injections (e.g., an area on one or both of the thighs 34, arms 38, or buttocks 36 or an area around the umbilicus 42 of the abdomen 32 of the mannequin). The size of the target body area and/or distribution of lipos within that area can be selected and varied among target body areas or among mannequins or modules configured to represent different patient types (e.g., patient types classified according to one or more of size, age, sex, severity of lipo progression, injection regimen, and so on) to reasonably simulate on the mannequin the location of lipos that typically occur in the designated body for most lipo sufferers or for lipo sufferers of a designated patient type.

Figure 40A:
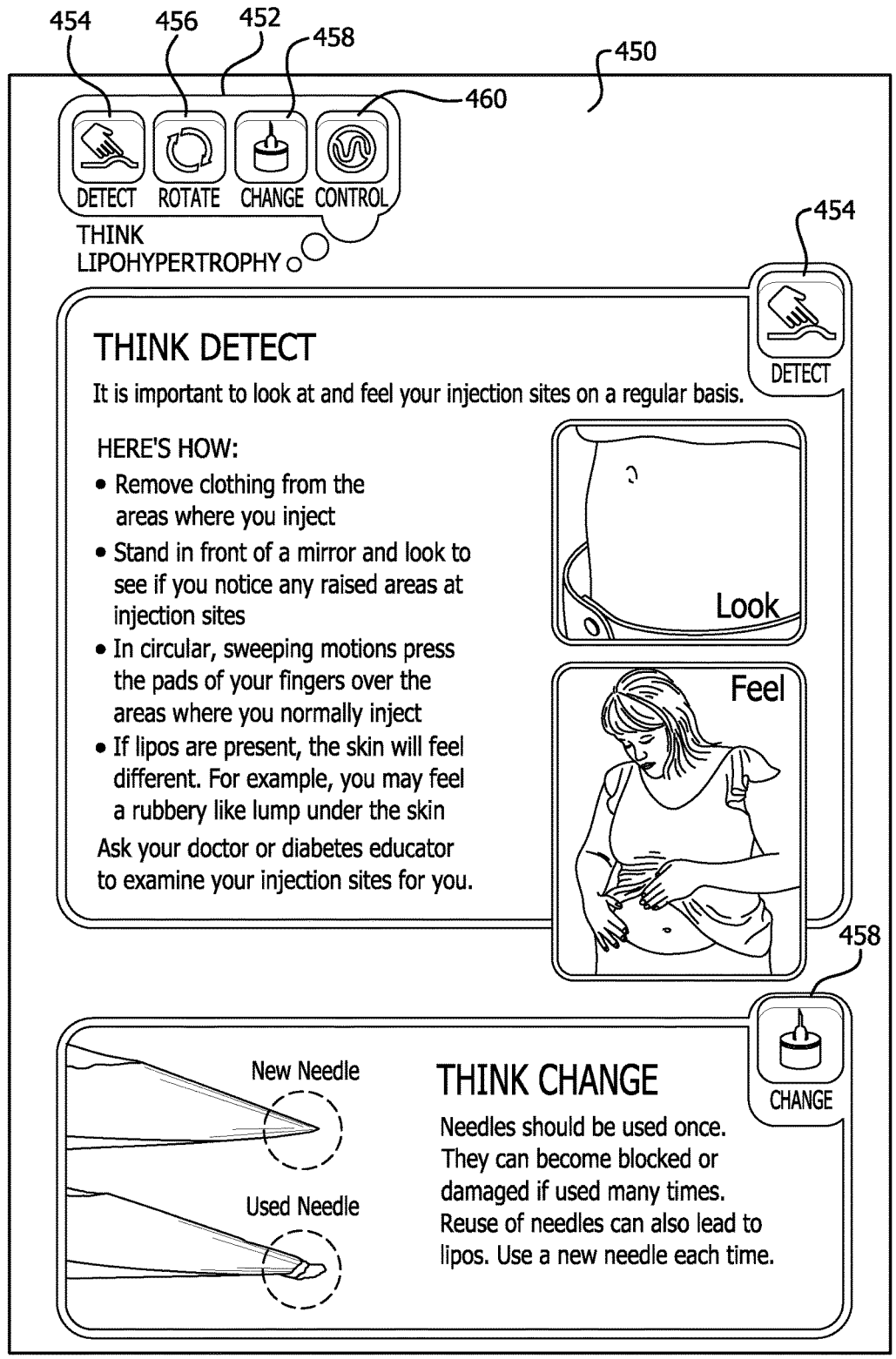

With reference to FIGS. 40A through 40F, another education tool 450 is provided that comprises print media (e.g., on a display screen 3304 or on paper, packaging or other printable material) indicating actions 452 necessary for preventing or at least reducing lipohypertrophy incidents such as Detect 454, Rotate 456, Change 458 and Control 460. For example, the tool 450 can provide information on how to detect any occurrences of lipos 454, as well as a reminder to change needles 458, as shown in FIG. 40A.

Figure 40B:
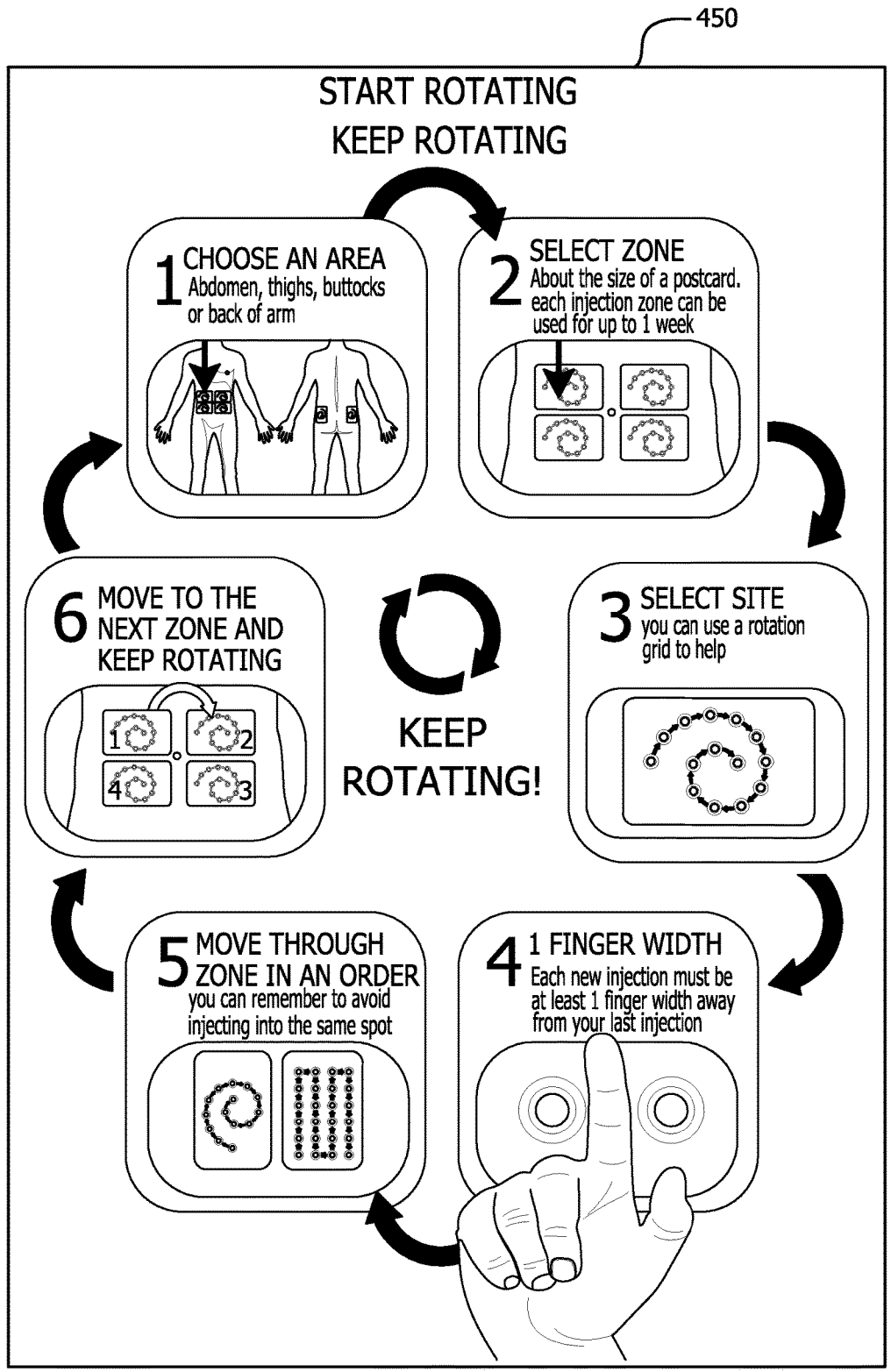
Figure 40C:
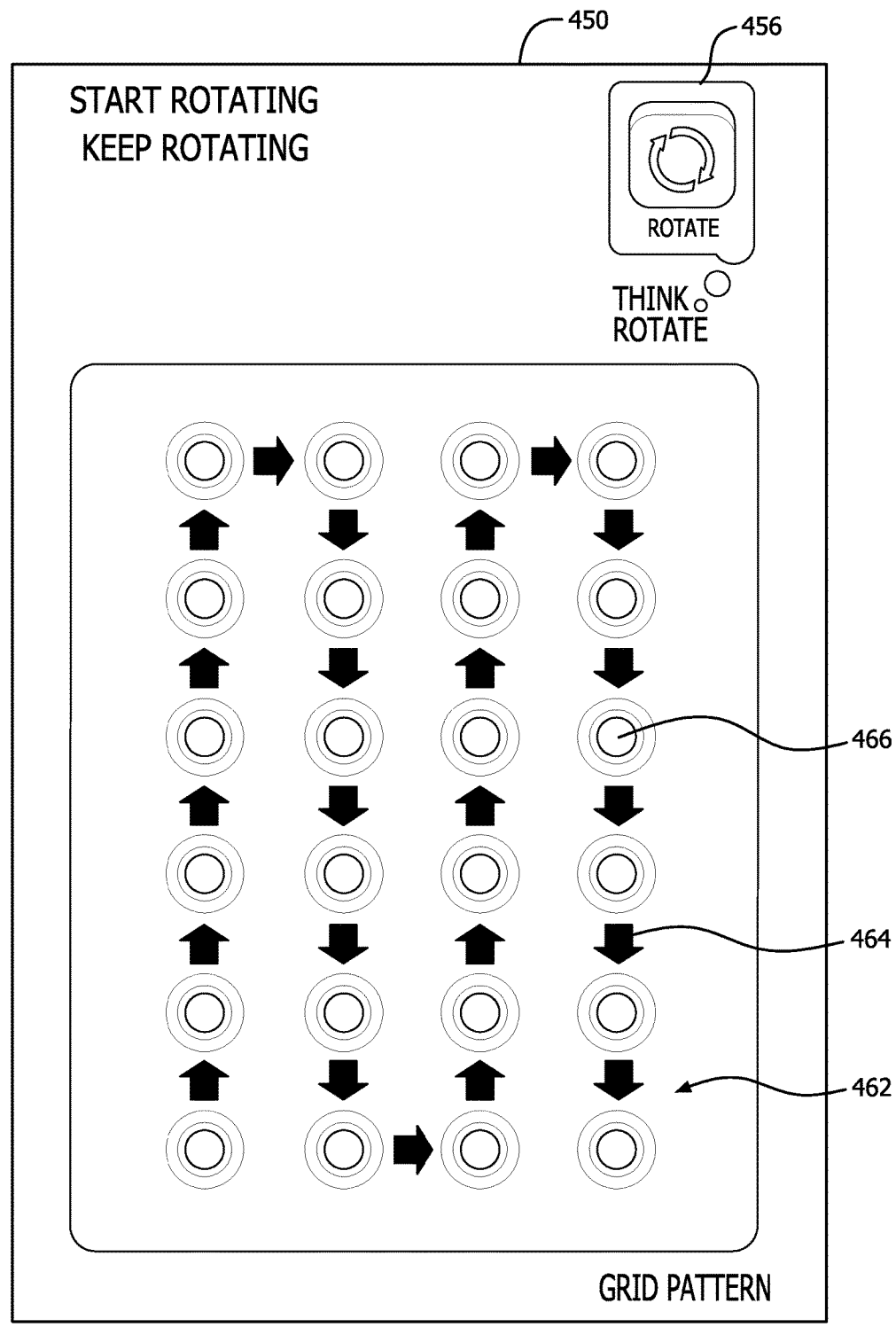
Figure 40D:
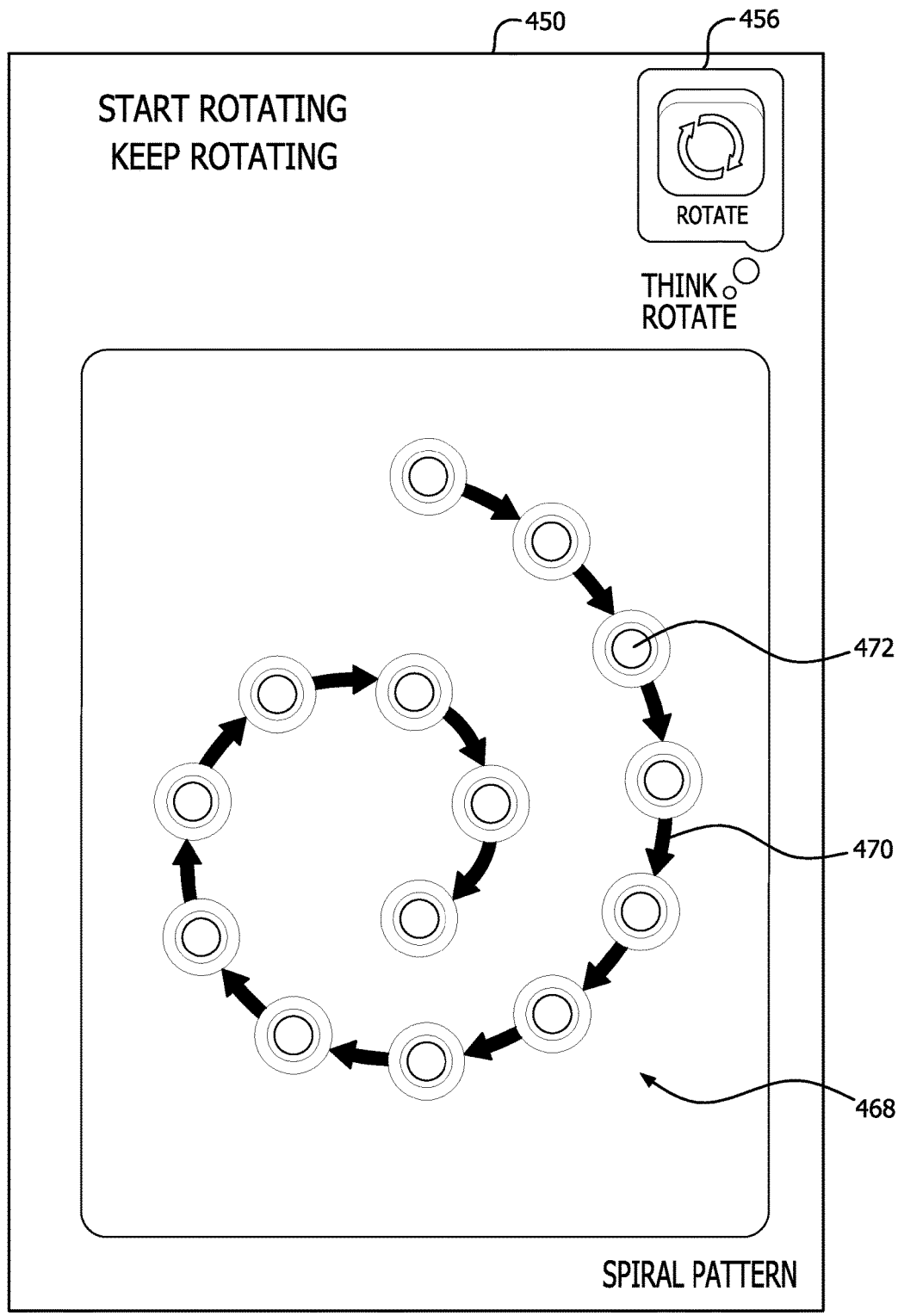

Also, one or more guidelines for rotating can 456 be provided as indicated in FIGS. 40B, 40C and 40D. For example, FIG. 40C illustrates a grid pattern 462 comprising a matrix of target injection sites 466 and arrows 464 for guiding a patient or user to inject at target sites in a designated order and spatial pattern. Another example pattern for injecting using site rotation is provided in FIG. 40D and comprises a spiral pattern 468, that is, a plurality of target injection sites 472 distributed along a curved line with arrows 470 indicating an order for injecting among the target injection locations 472.

Figure 40E:
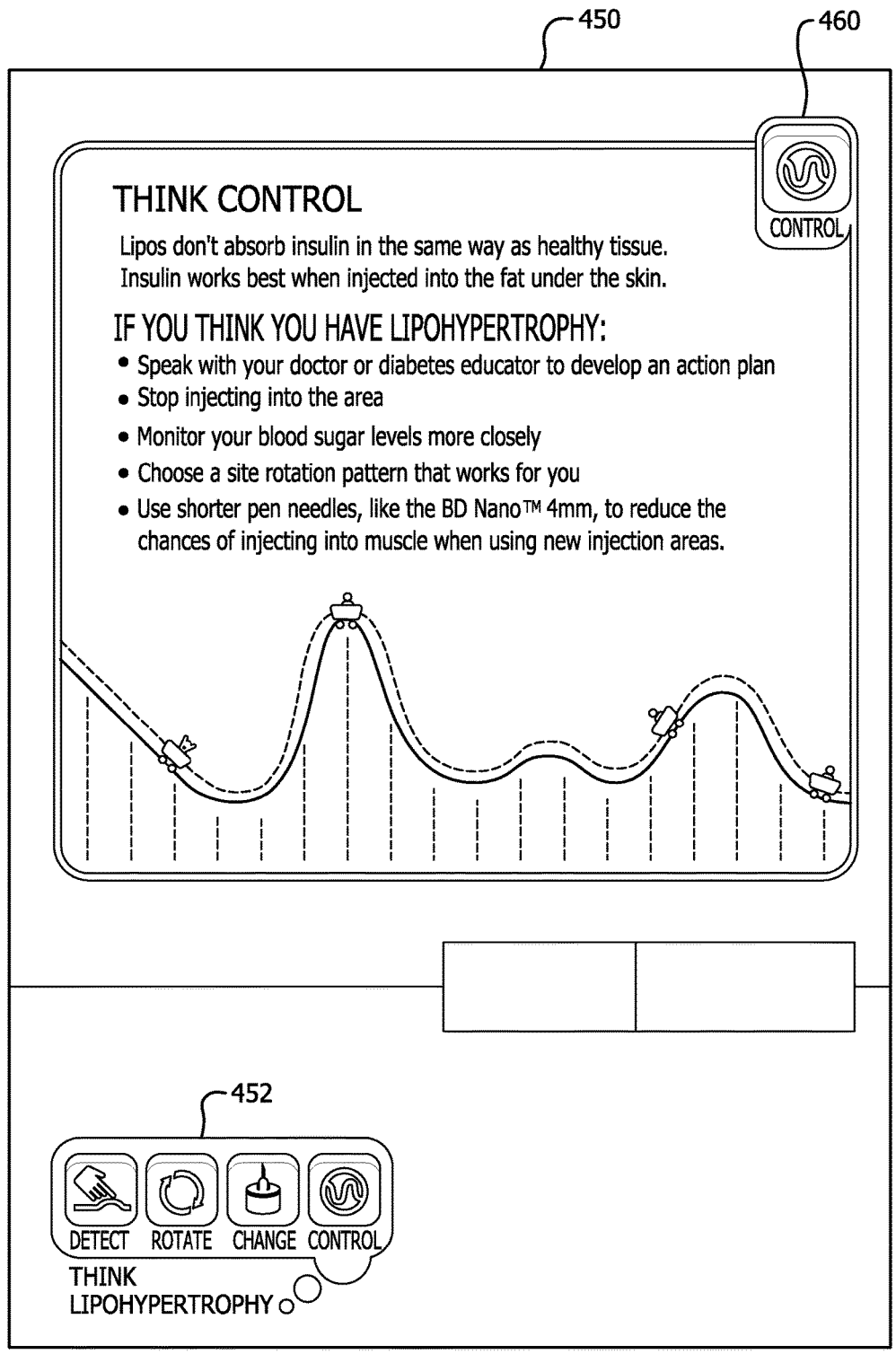

FIG. 40E provides guidelines 460 for controlling blood sugar and insulin or other blood characteristics and/or for injecting medicine when lipos are detected. FIG. 40F provides additional information on lipohypertrophy. The education tool 450 can, for example, employ recommendations for reducing lipohypertrophy from the Forum for Injection Technique (FIT) and available at www.fit4diabetes.com. The print media provided in FIGS. 40A through 40F can be provided together in a brochure or as a poster or other type of wall or other surface display, or on packaging. Alternatively, portions of the print media can be provided on a brochure or in a poster or other type of wall or other surface display, or on packaging.

Figure 41:
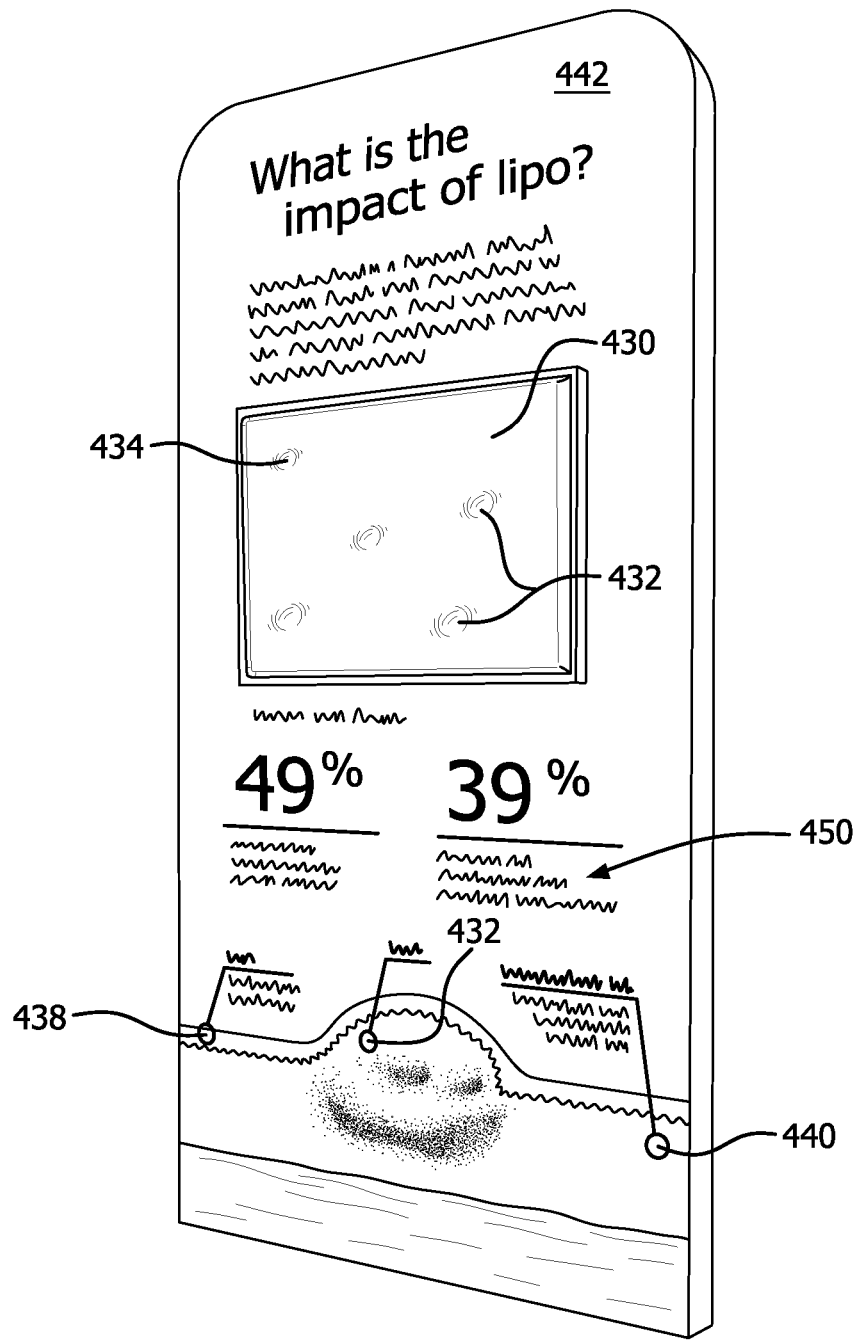

FIG. 41 illustrates a standing display or wall display 442 having a tactile lipo education tool 430 integrated in or affixed to a surface thereof. The standing display can be, for example, affixed to a floor or otherwise balanced via a base or stand to allow a person to view information 450 on at least one side thereof. For example, the display 442 can be dimensioned to be between 4 and 7 feet in height and between 2 and 4 feet wide. A tool 430 can be dimensioned, for example, to extend across a selected area of the display as shown in FIG. 41 to allow a user to conveniently reach and touch the tool 30 and achieve a reference sensation from the simulated lipos 432 and 434 to facilitate detecting a lipo in a patient's body. Alternatively, a plurality of tools 430 having smaller dimensions can be provided and distributed on the display 442 to allow multiple users to access respective tools 430 at the same time. Also, the density or texture and/or the distribution of the simulated lipos 432 and 434 can be varied among a tool or tools 430 on a display to demonstrate different sizes or patterns of lipos that may typically occur given a particular body area and/or patient profile and/or injection regimen or habitual injection pattern. The information 450 can comprise, for example, a definition for "lipo" or "lipohypertrophy" (e.g., Lipohypertrophy is a thickened 'rubbery' lesion that appears in the subcutaneous fat (SC) tissue of injecting sites in many patients who inject insulin. In some patients, the lesions can be hard or scar like.). Statistics regarding the impact of lipos or lipohypertrophy can also be provided by the information 450 on the display 442 (e.g., 49% of patients with lipohypertrophy have glycemic variability; 39% of patients with lipohypertrophy have unexplained hypoglycemia.)

Figure 42:
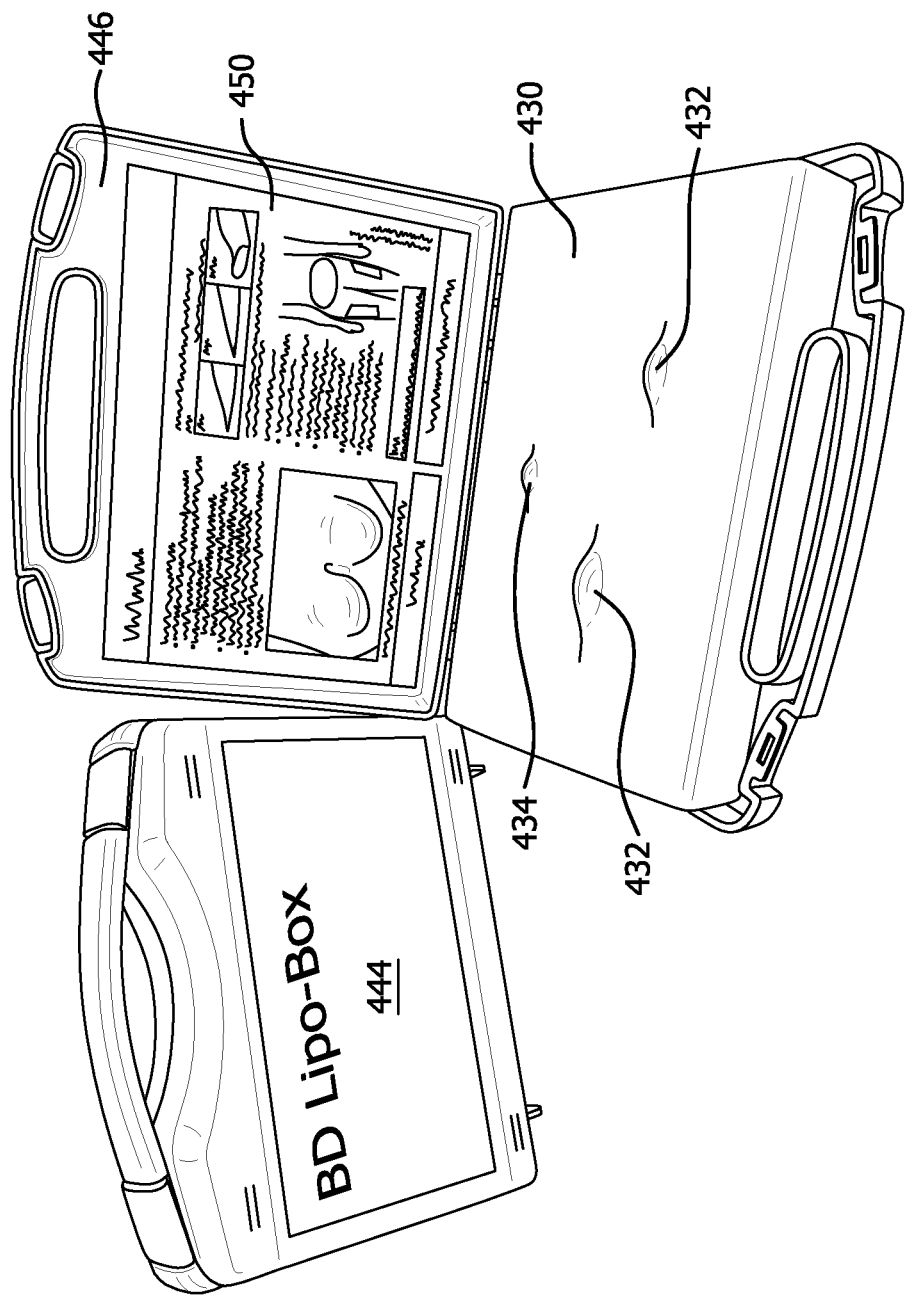

FIG. 42 illustrates a lipo tactile education tool 430 disposed in a portable display case 444 having a lid 446 to enclose the tool 430 and any related surfaces or components providing information 450. As stated above, the tool 430 is configured from synthetic material(s), for example, to simulate lipos 432 and 434 (e.g., a texture or density similar to that of a typical lipo) when palpated or otherwise touched by a user. The tool 430 can be affixed within the case 444 or detachably placed inside the case 444 for removal from the case 444 by a user for more convenient access to the tool for palpation. The information 450 can comprise, for example, recommendations 452 for site rotation as illustrated in FIGS. 39A-39B and/or 40A-40F Additional Embodiments and Implementations Although illustrative embodiments of the present invention have been described with respect to minimizing the occurrence of, and in some embodiments detecting, lipohypertrophy, they can also be used for other types of lipodystrophy such as lipoatrophy which presents as areas where subcutaneous fat is wasting or degenerating and in which absorption of insulin may therefore be more rapid and unpredictable in comparison to normal skin areas since insulin or medicament molecules may have a shorter distance to travel to reach a capillary.

Illustrative embodiments of the present invention have been described with reference to operations at a programmable device such as a computerized insulin delivery or monitoring apparatus (e.g., pen needle, CGM, infusion pump), handheld device, mobile phone, or other user devices. It is to be understood, however, that the present invention can also be embodied as computer-readable codes on a computer-readable recording medium. The computer-readable recording medium is any data storage device that can store data which can thereafter be read by a computer system. Examples of the computer-readable recording medium include, but are not limited to, read-only memory (ROM), random-access memory (RAM), CD-ROMs, DVDs, magnetic tapes, floppy disks, optical data storage devices. It is envisioned that aspects of the present invention can be embodied as carrier waves (such as data transmission through the Internet via wired or wireless transmission paths). The computer-readable recording medium can also be distributed over network-coupled computer systems so that the computer-readable code is stored and executed in a distributed fashion.

The components of the illustrative devices, systems and methods employed in accordance with the illustrated embodiments of the present invention can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the invention can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

What is claimed is:

1. A reminder system for varying the locations of an injection site, comprising:
    a user-operable device including an indicator, the indicator comprising
    a rotatable lost-tooth device with at least one gear tooth and having indicia thereon related to respective days of the week; and
    a rotatable indicator device disposed adjacent to the lost-tooth device, the indicator device comprising gear teeth and indicia comprising an indicium for each of a plurality of body areas for injection sites, the body areas comprising buttocks, thighs and abdomen;
    wherein the at least one gear tooth is configured on the lost-tooth device to engage the gear teeth of the indicator device during part of a rotation of the lost-tooth device to advance the indicia by one indicium corresponding to a respective body area during one full rotation of the lost-tooth device.

2. The system according to claim 1, wherein the lost-tooth device is configured as a lost-tooth sleeve, which is rotatably secured to one of a medication device selected from the group consisting of an injection pen body, an injection pen cap, and a medicament vial.

3. The system according to claim 2, wherein the indicator device is configured as an indicator sleeve and further comprising
    a mechanism linking the lost-tooth sleeve and the indicator sleeve so that advancing the lost-tooth sleeve by seven indicia advances the indicator sleeve by a single indicia, the mechanism comprising
    a biasing device disposed between the lost-tooth sleeve and the indicator sleeve and configured to bias the lost-tooth sleeve distally toward the end of the medication device,
    a cam track and a follower disposed on respective ones of the lost-tooth sleeve and the medication device such that, when the lost-tooth sleeve is rotated relative to the medication device, the follower is guided in the cam track,
    the cam track having a first portion that guides the follower in a substantially planar manner and the biasing device prevents the lost-tooth sleeve from contacting the indicator sleeve,
    the cam track having a second portion configured to permit the follower and the lost-tooth sleeve to overcome the bias of the biasing device, displacing the lost-tooth sleeve toward the indicator sleeve and allowing contact between the at least one gear tooth of the lost-tooth sleeve with the gear teeth of the indicator sleeve.

4. The system according to claim 3, wherein the lost-tooth sleeve and the indicator sleeve are disposed inside the medication device, and the medication device comprises at least one window through which indicia on the lost-tooth sleeve and the indicator sleeve are visible.

5. The system according to claim 3, wherein the lost-tooth sleeve and the indicator sleeve are disposed inside the medication device, the medication device comprises a plurality of windows, at least one of the plurality of windows being configured to allow one of the indicium on the lost-tooth sleeve to be visible, and a subset of the plurality of windows corresponds to respective ones of the body areas, the indicium of the indicator sleeve being configured to fill in a respective one of the subset of windows depending on the rotation of the indicator sleeve by the lost-tooth sleeve.

6. The system according to claim 5, wherein the exterior of the medication device is provided with a graphical human form, and the subset of the plurality of windows are arranged within the graphical human form in accordance with the respective body areas to which they correspond.

7. The system according to claim 1, wherein the lost-tooth device and the indicator device are each configured as a disc.

8. A reminder system for varying the location of an injection site, comprising:
- an indicator having indicia thereon and comprising an indicator sleeve, which is movably disposed inside an injection pen having an injector button, and has a plurality of radial protrusions disposed on the indicator sleeve, each of the plurality of radial protrusions corresponding to a single one of the indicia, the indicia being visible one at a time through a window disposed on the injection pen; and
- a rotating mechanism comprising a primary advancing protrusion disposed on the injection pen;
- wherein upon distal displacement of the injector button to complete an injection, the injector button displaces the indicator sleeve distally, and the interaction between the primary advancing protrusion and a proximal one of the radial protrusions during the distal displacement of the indicator sleeve causes rotation of the indicator sleeve.

9. The system according to claim 8, further comprising:
- a biasing member biasing the indicator sleeve proximally relative to the injection pen; and
- a secondary advancing protrusion disposed on the injection pen, the secondary advancing protrusion being circumferentially and axially offset from the primary advancing protrusion;
- wherein upon proximal displacement of the indicator sleeve due to the biasing member, the interaction between the secondary advancing protrusion and one of the radial protrusions during the proximal displacement of the indicator sleeve causes additional rotation of the indicator sleeve.

10. The system according to claim 8, wherein the indicia on the indicator sleeve correspond to respective body areas for injection sites.

11. The system according to claim 10, wherein the indicia are repeated a given number of times on the indicator sleeve and advanced by one indicia upon distal displacement of the injector button to complete an injection for viewing through the window for a given number of injections.

* * * * *